(12) United States Patent
Yu et al.

(10) Patent No.: US 6,919,331 B2
(45) Date of Patent: *Jul. 19, 2005

(54) SUBSTITUTED 2-METHYL-BENZIMIDAZOLE RESPIRATORY SYNCYTIAL VIRUS ANTIVIRAL AGENTS

(75) Inventors: Kuo-Long Yu, Zionsville, IN (US); Xiangdong Wang, Guilford, CT (US); Yaxiong Sun, Thousand Oaks, CA (US); Christopher Cianci, Madison, CT (US); Jan Willem Thuring, Antwerp (BE); Keith Combrink, Burleson, TX (US); Nicholas Meanwell, East Hampton, CT (US); Yi Zhang, San Diego, CA (US); Rita L. Civiello, Killingworth, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 26 days.

This patent is subject to a terminal disclaimer.

(21) Appl. No.: 10/309,505

(22) Filed: Dec. 4, 2002

(65) Prior Publication Data

US 2003/0207868 A1 Nov. 6, 2003

(Under 37 CFR 1.47)

Related U.S. Application Data

(60) Provisional application No. 60/339,025, filed on Dec. 10, 2001.

(51) Int. Cl.[7] .................. C07D 235/26; C07D 401/06; C07D 403/06; C07D 413/14; C07D 471/04
(52) U.S. Cl. .............. 514/223.2; 514/266.23; 514/303; 514/312; 514/364; 514/387; 514/397; 514/400; 544/12; 544/284; 546/118; 546/157; 548/144; 548/305.1; 548/305.7; 548/310.1
(58) Field of Search ................ 514/223.2, 266.23, 514/303, 312, 364, 387, 397, 400, 359, 394, 300, 248; 544/12, 284, 236; 546/118, 157, 155, 119, 113; 548/144, 305.1, 305.7, 310.1, 256, 132, 131

(56) References Cited

U.S. PATENT DOCUMENTS

| 3,394,141 A | 7/1968 | Sparatore .................. 260/294.7 |
| 4,324,794 A | 4/1982 | Tidwell et al. .............. 424/273 |
| 5,256,668 A | 10/1993 | Hsu et al. .................... 514/269 |

FOREIGN PATENT DOCUMENTS

| AU | A-14704 | | 12/1998 |
| EP | 058146 A1 | | 8/1982 |
| WO | WO 00/04900 | * | 2/2000 |
| WO | WO 00/38508 | | 7/2000 |
| WO | WO 01/00611 | | 1/2001 |
| WO | WO 01/00612 | | 1/2001 |
| WO | WO 01/00615 | | 1/2001 |
| WO | WO 01/36395 | | 5/2001 |

OTHER PUBLICATIONS

F. Pagani, et al, Boll. Chim. Farm., 104, pp. 427–431, 1965.

G. Paglietti, et al, Il. Farmaco–Ed. Sc., 30, pp. 505–511, 1975.

S. Shigeta, et al, Antiviral Chemistry & Chemotherapy, 3(3), pp. 171–177, 1992.

S. N. Kolodyazhnaya, et al, "Nitrogen–containing bisheterocyclic systems. II. Nature of the influence of the 2–benzimidazolyl radical," Chemical Abstracts, 72(21), p. 395, col. 1, Abstract No. 111365d, 1970 (Khimiya Geterotsiklicheskikh Soedinenii, pp. 238–244, (2), 1970 (Russ.).

* cited by examiner

*Primary Examiner*—Bruck Kifle
(74) *Attorney, Agent, or Firm*—James Epperson; Samuel J. DuBoff

(57) ABSTRACT

The present invention concerns antiviral compounds, their methods of preparation and their compositions, and use in the treatment of viral infections. More particularly, the invention provides heterocyclic substituted 2-methylbenzimidazole derivatives for the treatment of respiratory syncytial virus infection.

6 Claims, No Drawings

SUBSTITUTED 2-METHYL-BENZIMIDAZOLE RESPIRATORY SYNCYTIAL VIRUS ANTIVIRAL AGENTS

REFERENCE TO RELATED APPLICATIONS

This application claims the benefit of U.S. Provisional Application Ser. No. 60/339,025 filed Dec. 10, 2001.

BACKGROUND OF THE INVENTION

1. Field of the Invention

The present invention concerns antiviral compounds, their methods of preparation and their compositions, and use in the treatment of viral infections. More particularly, the invention provides substituted 2-methylbenzimidazole derivatives for the treatment of respiratory syncytial virus infection.

2. Background Art

Respiratory syncytial virus (RSV) is the leading cause of serious lower respiratory tract infection in infants, children, elderly and immunocompromised persons. A severe viral infection may require hospitalization for bronchiolitis or pneumonia and in some cases the viral infection is fatal. (*JAMA*, 1997, 277, 12). Currently only Ribavirin is approved for the treatment of this viral infection. Ribavirin is a nucleoside analogue which is administered intranasally as an aerosol. The agent is quite toxic, and its efficacy has remained controversial. RespiGam, approved for prophylaxis in high risk pediatric patients, is an intravenous immunoglobulin which effectively neutralizes the virus. Recently, Synagis, a monoclonal antibody administered through intramuscular injection has also been approved for use in high risk pediatric patients. However, both drugs are very expensive. Accordingly, inexpensive, safe and effective antiviral agents against respiratory syncytial virus will be beneficial for patients.

Many agents are known to inhibit respiratory syncytial virus (De Clercq, *Int. J. Antiviral Agents*, 1996, 7, 193). Y. Tao et al. (EP 0 058 146 A1, 1998) disclosed that Ceterizine, a known antihistamine, exhibited anti-RSV activity. Tidwell et al.,*J. Med. Chem.* 1983, 26, 294 (U.S. Pat. No. 4,324,794, 1982), and Dubovi et al., *Antimicrobial Agents and Chemotherapy*, 1981, 19, 649, reported a series of amidino compounds with the formula shown below as inhibitors of RSV.

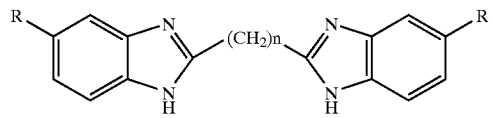

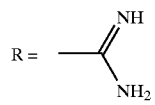

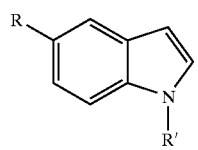

R' = Me

Hsu et al., U.S. Pat. No. 5,256,668 (1993) also disclosed a series of 6-aminopyrimidones that possess anti-viral activity against RSV.

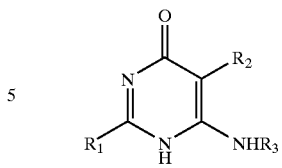

Y. Gluzman, et al., (AU Patent, Au-A-14,704, 1997) and P. R. Wyde et al. (*Antiviral Res.* 1998, 38, 31) disclosed a series of triazine containing compounds that were useful for the treatment and/or prevention of RSV infection.

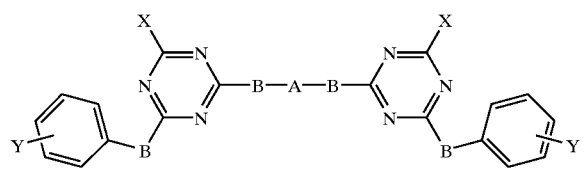

In addition, T. Nitz, et al., (WO Patent, WO 00/38508, 1999) disclosed a series of triaryl containing compounds that were useful for the treatment and/or prevention of RSV and related pneumoviral infections.

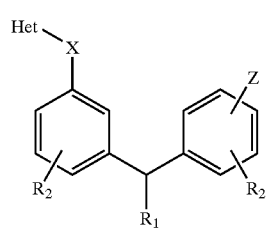

Moreover, Yu et al. (WO 020004900) also disclosed a series of substituted benzimidazoles that is useful for the treatment and prevention of RSV infection.

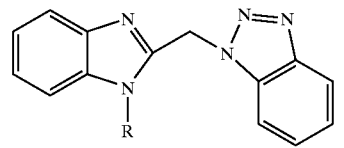

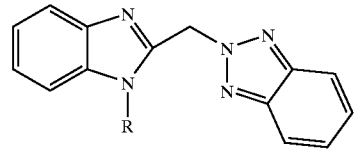

A related series of compounds were first disclosed by F. Pagani and F. Sparatore in *Boll Chim Farm.* 1965, 104, 427 and by G. Paglietti, et al. in *Il Farmaco, Ed. Sci.* 1975, 30, 505, and found to possess analgesic and anti-arrhythmic activity. The structural formula for these compounds are depicted in Formula Ia and Ib.

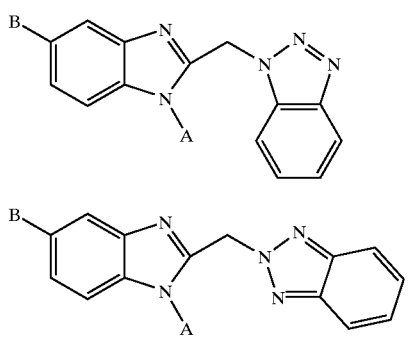

Formula 1a

Formula 1b

In Formula Ia and Ib, A is —(CH$_2$)n—N(R)$_2$, n=2 or 3, R=Me or Et, or A is

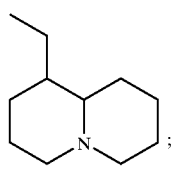

B=H, Cl, CF$_3$, CH$_3$CO, NO$_2$.

Another series of closely related compounds that Sparatore had disclosed were in *Il Farmaco Ed. Sci.* 1967, 23, 344 (U.S. Pat. No. 3,394,141, 1968). Some of the compounds were reported to have analgesic, anti-inflammatory or antipyretic activities. The structure of these compounds is depicted in Formula Ic. In Formula Ic, C=H, CF$_3$, or NO$_2$. D is —(CH$_2$)n—NR$_2$, n=2 or 3, R=Me or Et, or D=

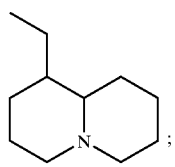

E is H, Cl or OEt.

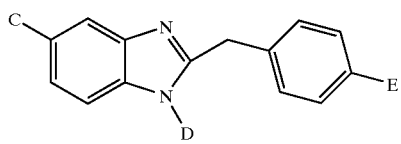

Formula Ic

Another series of compounds structurally related to this invention are pyrido[1,2-a]benzoazoles and pyrimidio[1,2-a]benzimidazoles disclosed by S. Shigeta et al in *Antiviral Chem. & Chemother.* 1992, 3, 171. These compounds have demonstrated inhibition of orthomyxovirus and paramyxovirus replication in HeLa cells. The structures of these compounds are shown in Formulas Id and Ie, in which F=NH, S, or O; Q=—NHCOPh, —COOH, COOEt, or CN; T=COMe, CN, or COOEt; G=O or NH.

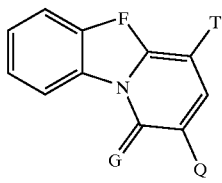

Formula Id

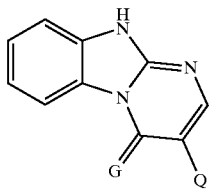

Formula Ie

A bis-benzimidazole with an ethylenediol linker shown below has also been reported as a potent inhibitor of rhinoviruses (Roderick, et al. *J. Med. Chem.* 1972, 15, 655).

A series of 2-aminobenzimidazoles have been reported by E. Janssens, et al. as inhibitors of RSV in a series of recent publications and representative examples (Formula 1f–1h) are shown below from PCT WO 01/00611 A1; PCT WO 01/00612 and PCT WO 01/00615, respectively all published on Jan. 4, 2001.

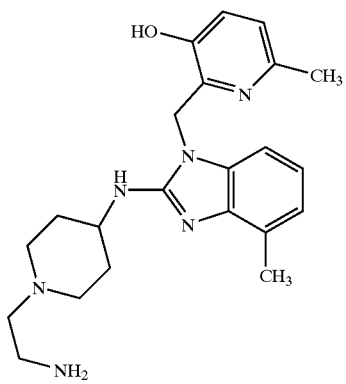

Formula If

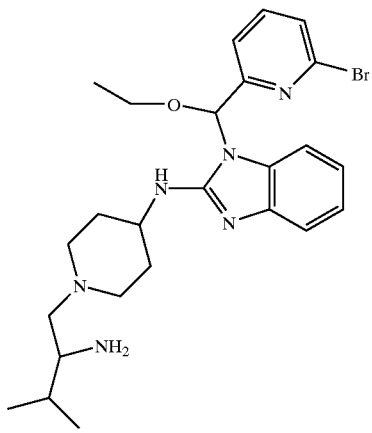

Formula Ig

Formula Ih

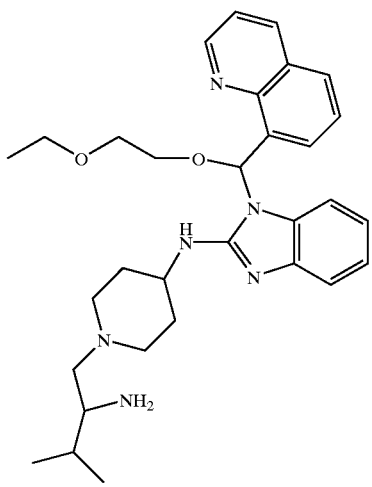

A series of triazole containing compounds have been reported by Janssen as inhibitors of RSV in PCT WO 01/36395 (May 25, 2001) and a representative example (Formula Ii) is shown below.

Formula Ii

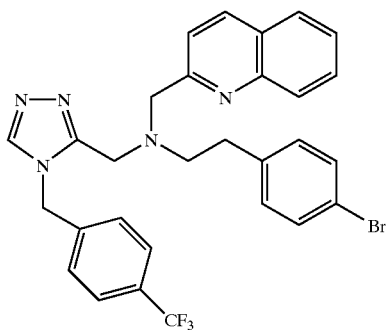

A bis-benzimidazole with an ethylenediol linker shown below has also been reported as a potent inhibitor of rhinoviruses (Roderick, et al. *J. Med. Chem.* 1972, 15, 655.

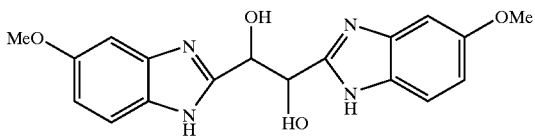

Other structurally related compounds are bis-benzimidazoles which possess antifungal activity (B. Cakir, et al. *Eczacilik Fak. Derg.* 1988, 5, 71).

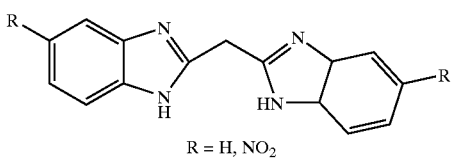

Also, H. R. Howard et al. reported a series of benzimidazolone-1-acetic acids that possessed aldolase reductase inhibitory activity (*Eur. J. Med. Chem.* 1992, 27, 779–789).

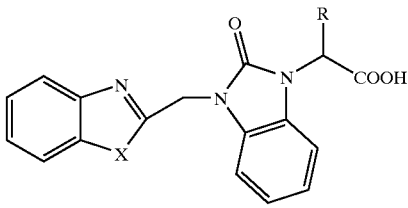

X = O, S

Other prior art related to the chemical structure of the present invention:
(1) F. Sparatore, et al, "Derivati Benzotriazolici Attivi Sull'accrescimento Delle Piante," *Il Farmaco Ed. Sci.* 1978, 33, 901.
(2) Katritzky, A. R. et al, "Synthesis and Transformations Of Substituted Benzazolyl- and Tetrazolyl(benzotriazol-1-yl) methanes," *J. Heterocyclic Chem.* 1996, 33, 1107.
(3) Terri A. Fairley, et al. "Structure, DNA Minor Groove Binding, And Base Pair Specificity of Alkyl and Aryl-Linked Bis(amidinobenzimidazoles) and Bis (amidinoindoles), *J. Med. Chem.* 1993, 36, 1746.
(4) R. K. Upadhyay et al, "New Synthesis and Biological Evaluation," *Indian J. Heterocyclic Chem.* 1994, 4, 121.
(5) A. R. Katritzky, et al, "A New Route to N-substituted Heterocycles," *Tetrahedron,* 1993, 49, 2829.
(6) K. Yu et al. in Substituted Benzimidazole Anti-viral Agents, PCT WO00/04900 published Feb. 3, 2000.

SUMMARY OF THE INVENTION

This invention relates to novel substituted 2-methylbenzimidazoles and the antiviral activity against RSV. The structural formula for these compounds are depicted in Formula I, and includes pharmaceutically acceptable salts thereof, Formula I

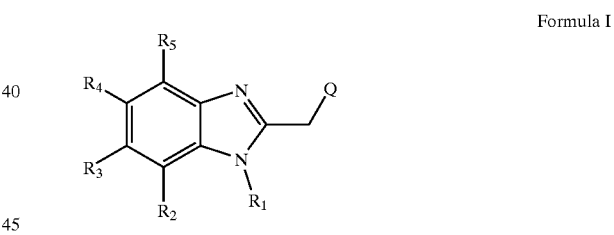

wherein:
$R_1$ is —$(CR^aR^b)_n$—X;
$R^a$ and $R^b$ are each independently selected from the group consisting of H and $C_{1-6}$ alkyl; said $C_{1-6}$ alkyl being optionally substituted with one to six same or different halogen;
X is H or $C_{1-6}$ alkyl; said $C_{1-6}$ alkyl being optionally substituted with halogen, $OR^c$ or $S(O)_mR^d$;
$R^c$ is H or $COR^d$;
$R^d$ is $C_{1-6}$ alkyl;
n is 1–6;
m is 0–2;
$R_2$ is H;
$R_3$ is $CONR^hR^i$, $CO_2R^d$ or $C_{1-6}$ alkyl; said $C_{1-6}$ alkyl can be optionally substituted with $OR^e$ or $NR^fR^g$;
$R^e$ is H or $C_{1-6}$ alkyl;
$R^f$ and $R^g$ are each independently H, $C_{1-6}$ alkyl, $SO_2R^d$, $CO_2R^d$ or $COR^d$;
$R^h$ and $R^i$ are each independently H or $C_{1-6}$ alkyl;
$R_4$ is selected from the group consisting of $NH_2$, $CONR^hR^i$, heteroaryl, $C_{2-6}$ alkenyl, $CO_2R^d$, N=$CPh_2$, C(=NOH)

$NH_2$, $C(=NH)NH_2$ and $C_{1-6}$ alkyl; said $C_{1-6}$ alkyl optionally substituted with a member selected from the group consisting of halogen, CN, $NR^lR^m$, $OSO_2R^d$ and $OR^e$;

$R^l$ and $R^m$ are each independently selected from the group consisting of H, $C_{1-6}$ alkyl, $C_{3-6}$ cycloalkyl, $CO_2R^d$, $COR^d$ and $SO_2R^d$;

$R_5$ is selected from the group consisting of (1) $CO_2R^j$; (2) $C_{1-6}$ alkyl optionally substituted with CN, $OR^e$ or $NR^fR^g$; and (3) $C_{2-6}$ alkenyl substituted with CN;

$R^j$ is H or $C_{1-6}$ alkyl;

Q is a member selected from the group consisting of

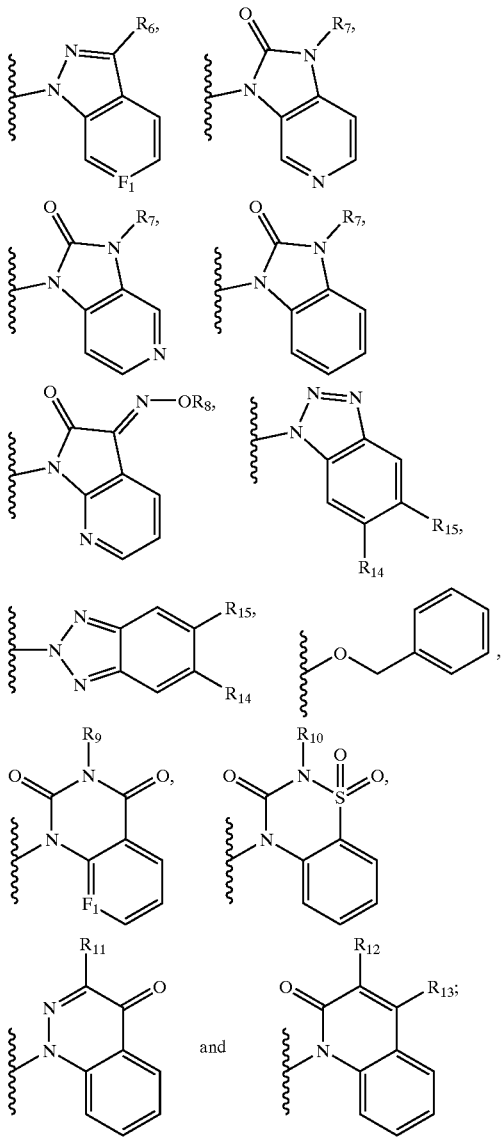

$F_1$ is CH or N;

$R_6$ is H, halogen, $C_{1-6}$ alkyl or $C_{2-6}$ alkenyl;

$R_7$ is H, $C_{1-6}$ alkyl, $C_{2-6}$ alkenyl, $CO_2R^d$ or $C_{3-6}$ cycloalkyl;

$R_8$ is H or $C_{1-6}$ alkyl; said $C_{1-6}$ alkyl optionally substituted with one to three halogen;

$R_9$ is $C_{1-6}$ alkyl or $C_{3-6}$ cycloalkyl; said $C_{1-6}$ alkyl optionally substituted with one to three halogen;

$R_{10}$ is $C_{1-6}$ alkyl or $C_{3-6}$ cycloalkyl; said $C_{1-6}$ alkyl optionally substituted with one to three halogen;

$R_{11}$ is H or $C_{1-2}$ alkyl;

$R_{12}$ is H;

$R_{13}$ is H or $OR^j$;

$R_{14}$ and $R_{15}$ are independently H, CN, $C(=NH)NH_2$ or $C(=NOH)NH_2$; and heteroaryl is a 5- or 6-membered aromatic ring containing at least one and up to four non-carbon atoms selected from the group consisting of O, N and S.

In a preferred embodiment, $R^a$ and $R^b$ are hydrogen.

In another preferred embodiment $R_1$ is 3-methyl-butyl or —$(CH_2)_n$—X; wherein n is 2–6; and X is a member selected from the group consisting of F, $SO_2R^d$ and $OR^c$.

In another preferred embodiment, heteroaryl is selected from the group consisting of 1,2,3-oxadiazolyl, 1,2,4-oxadiazolyl and 1,2,4-oxadiazol-5-one.

Another preferred embodiment includes a method for treating mammals infected with RSV, and in need thereof, which comprises administering to said mammal a therapeutically effective amount of one or more of the aforementioned compounds of Formula I.

Another preferred embodiment includes a pharmaceutical composition which comprises a therapeutically effective amount of one or more of the aforementioned compounds of Formula I.

The term pharmaceutically acceptable salt includes solvates, hydrates, acid addition salts and quarternary salts. The acid addition salts are formed from a compound of Formula I and a pharmceutically acceptable inorganic acid including but not limited to hydrochloric, hydrobromic, sulfuric, phosphoric, methanesulfonic, acetic, citric, malonic, fumaric, maleic, sulfamic, or tartaric acids. Quaternary salts include chloride, bromide, iodide, sulfate, phosphate, methansulfonate, citrate, acetate, malonate, fumarate, sulfamate, and tartrate.

Halogen means bromine, chlorine, iodine and fluorine.

DETAILED DESCRIPTION OF THE INVENTION

Compounds of Formula I may be prepared using the procedures outlined in Schemes I–XIV.

3-Chloro-4-nitrobenzonitrile I is treated with an amine to give II. The nitro group is reduced with catalytic hydrogenation to give diamine III (Scheme I). The benzimidazole VI is formed in a two step process by coupling the diamine III to a substituted acetic acid derivative IV to give an intermediate acetamide V. The amide bond can be formed using standard amide coupling reagents such as EDC, EEDQ or the acid can be converted to an acid chloride and then coupled to the diamine III (Scheme II). The acetamide V is heated briefly in warm acetic acid to give the desired benzimidazole VI (Scheme II). If acetoxyacetyl chloride (VIIa, R=Ac) or benzyloxyacetyl chloride (VIIb, R=Bn) are used VIIIa or VIIIb are obtained. Removal of the benzyloxy or acetoxy group gives 2-hydroxybenzimidazole IXa (Scheme III). Compound IXa is converted to IXb with thionyl chloride and used to alkylate a number of nitrogen containing heterocycles (Scheme IV). The heterocycle is N-alkylated with the 2-chloromethylbenzimidazole derivatives IXb using a variety of bases such as NaH, BTPP, $K_2CO_3$ or $Cs_2CO_3$ (Scheme IV).

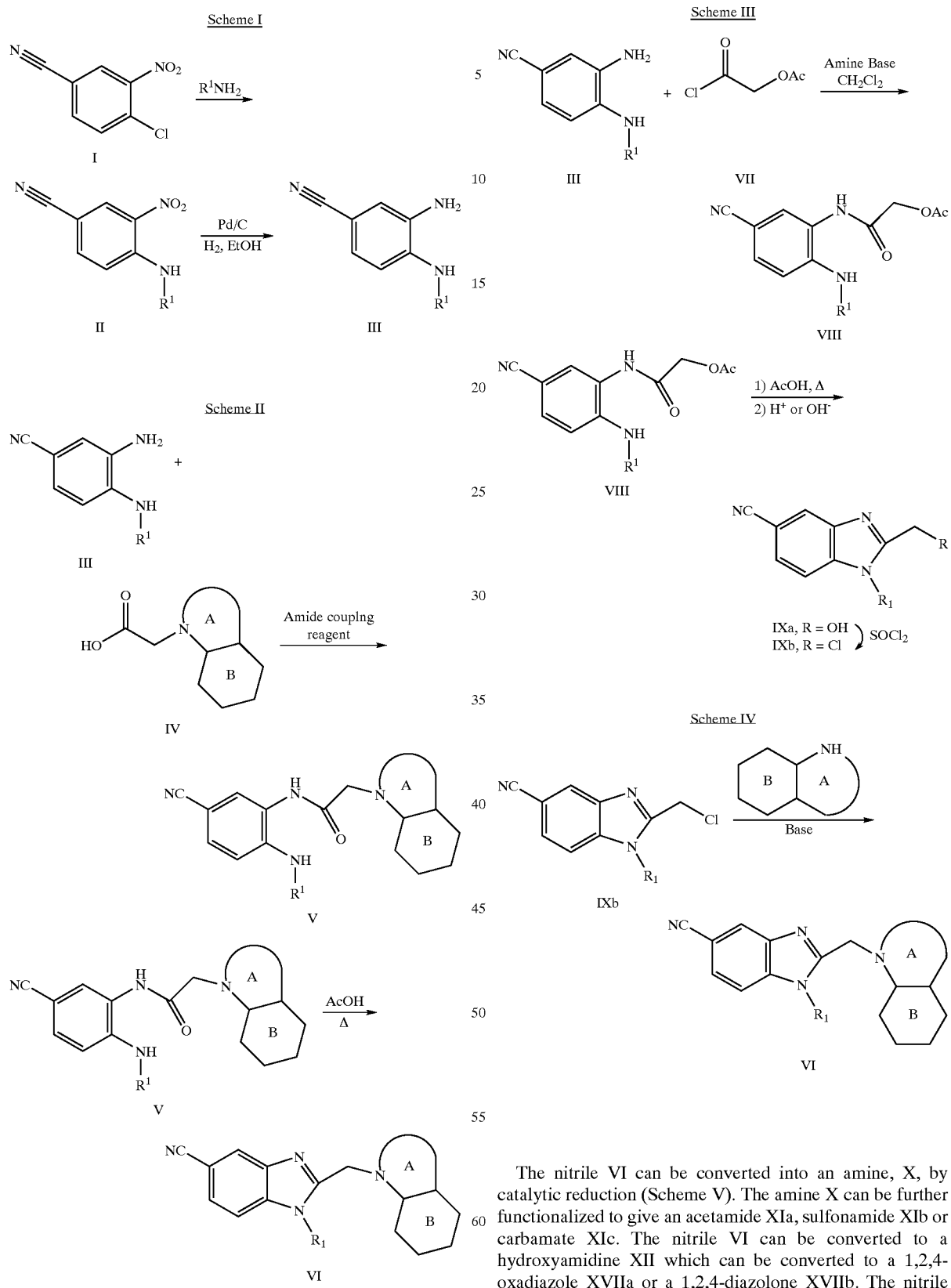

The nitrile VI can be converted into an amine, X, by catalytic reduction (Scheme V). The amine X can be further functionalized to give an acetamide XIa, sulfonamide XIb or carbamate XIc. The nitrile VI can be converted to a hydroxyamidine XII which can be converted to a 1,2,4-oxadiazole XVIIa or a 1,2,4-diazolone XVIIb. The nitrile can be hydrolyzed to an acid XV which can be further converted to an amide XVI or an ester XIII.

Scheme V

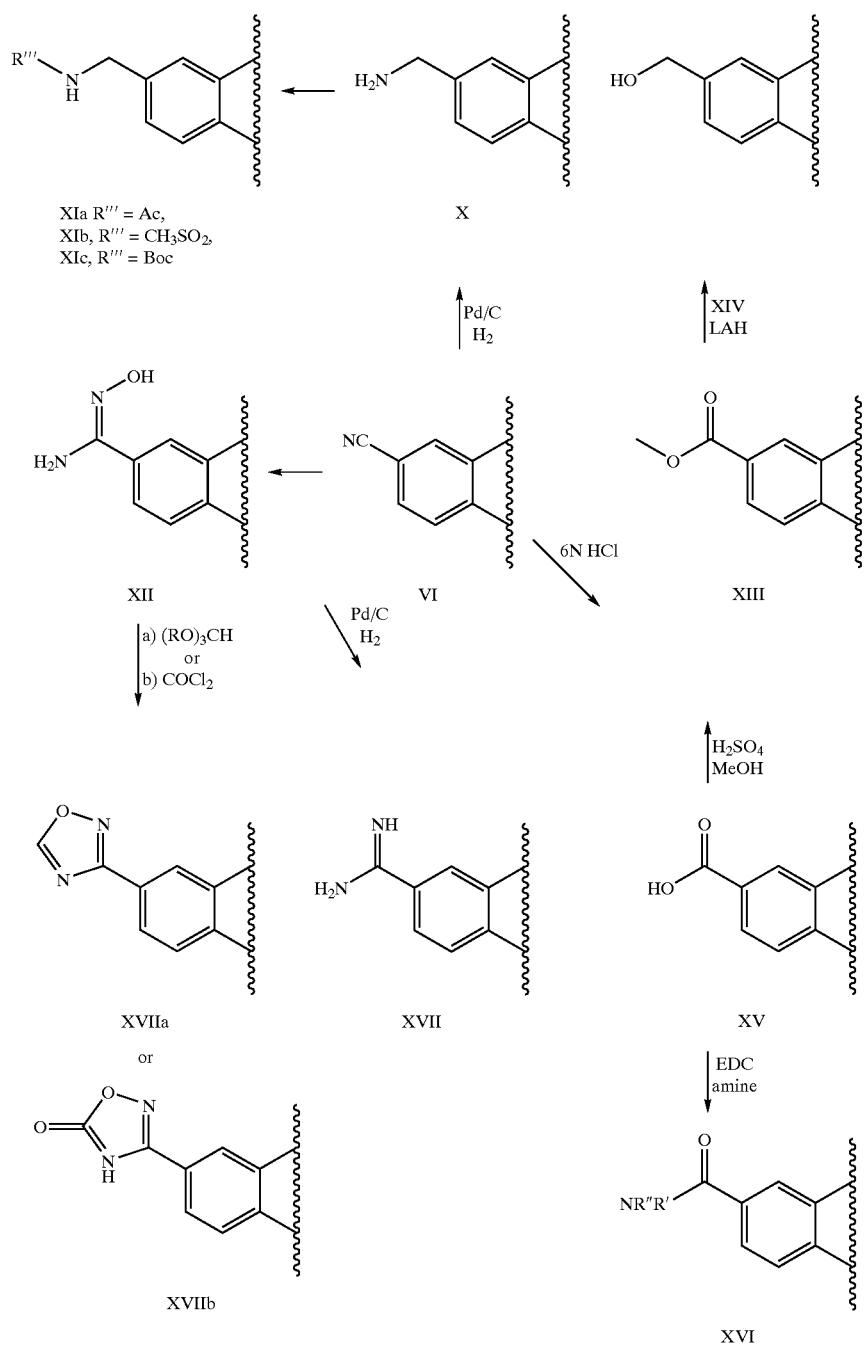

The ester XIII can be reduced to an alcohol XIV and converted to a fluoride XVIIIa, or mesylate XVIIIb. Alternatively, compound XIII can be converted to XIV by reduction of the mixed anhydride of XIII with NaBH₄ if other portions of the molecule are sensitive to LAH. Compound XVIIIb can be used to prepare secondary and tertiary amines XIX as well as an alkylnitrile XX. The alkylnitrile XX can in turn be reduced to give a homologated amine deriviative XXI (Scheme VI). The nitrile can also be treated with an organo-cerium reagent to give XXII (Scheme VII).

Scheme VI
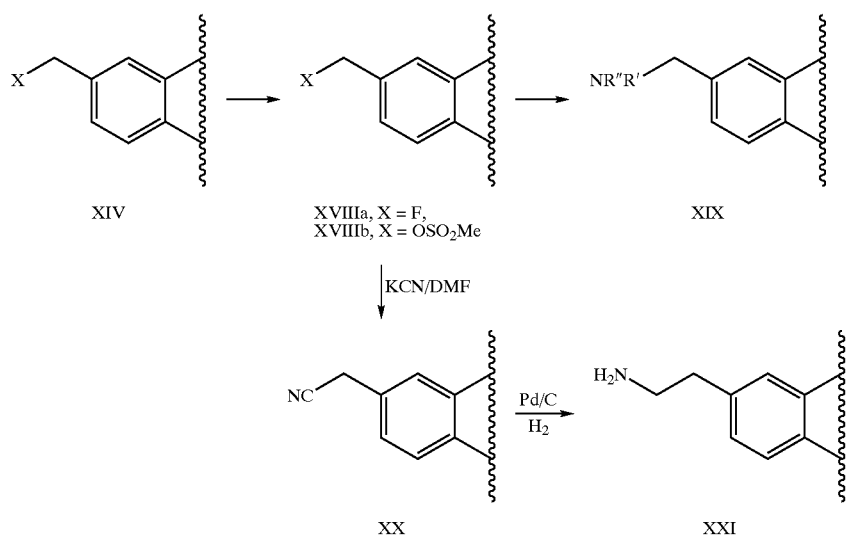
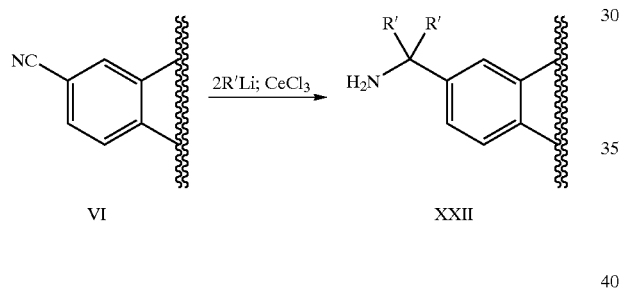
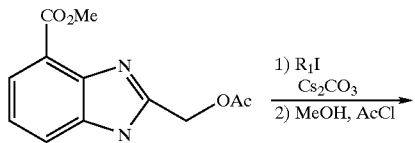
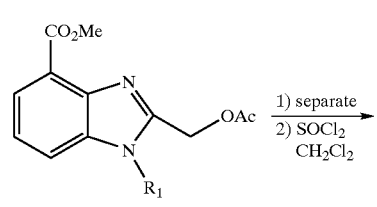
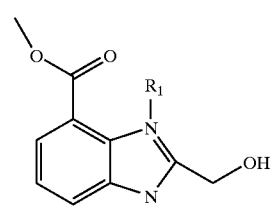
4-Substituted benzimidazoles are prepared from 2-amino-3-nitro-benzoic acid methyl ester as shown in Scheme VIII. N-Alkylation of XXV with an alkylhalide gives a 6:1 mixture of the desired benzimidazole XXVIa and XXVIb respectively. The synthesis of XXVIII was completed as described before.
Scheme VIII
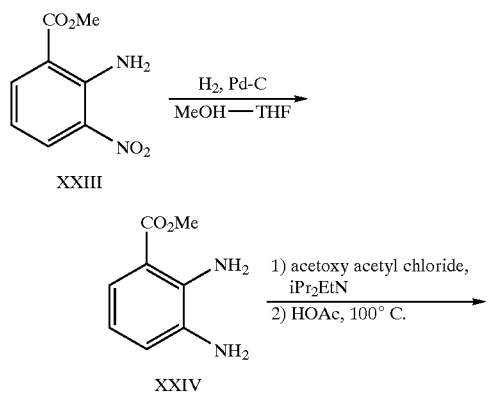
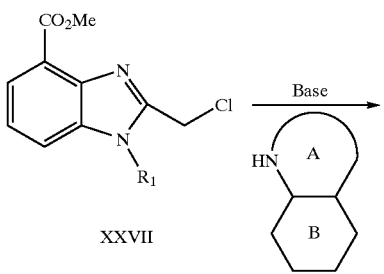

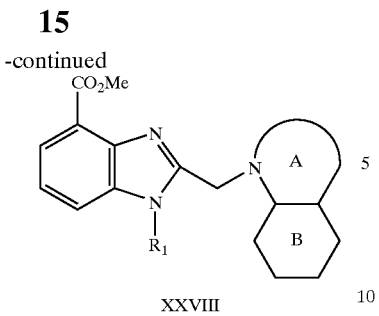

XXVIII

The ester XXVIII can be converted to a number of functional groups using transformations described for compound XIII above. In addition, the alcohol XXVIIIa can be oxidized to an aldehyde XVIIIb and condensed with acetonitrile to give a vinyl nitrile XXVIIIc which can be reduced to give a propylamine derivative XXVIIId (Scheme VIIIa).

Scheme VIIIa

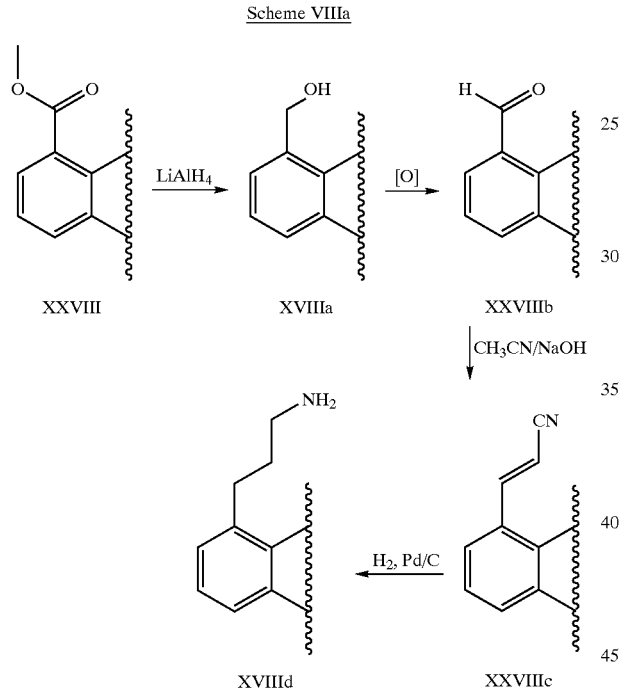

5-bromo-2-hydroxymethylbenzimidazole XXIX can be N-alkylated to give a 1:1 mixture of 5- and 6-substituted benzimidazole regioisomers XXX and XXXI which can be readily separated by various chromatographic methods. The 6-bromobenzimidazole XXXI can be converted to a nitrile XXXIII using Pd(PPh$_3$)$_4$ and Zn(CN)$_2$. Compound XXX can be converted to a 2-methylchloro derivative XXXb with SOCl$_2$ then XXXb used to alkylate various nitrogen containing heterocycles (Scheme IX).

Scheme IX

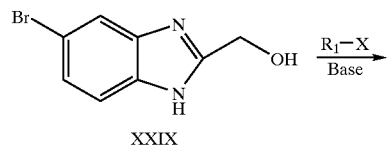

XXIX

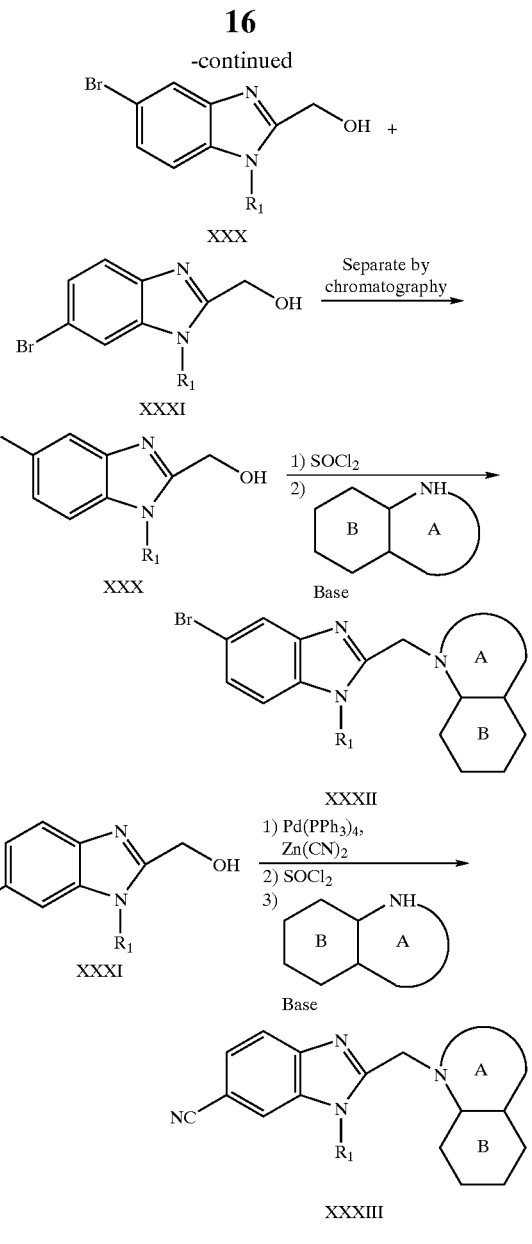

The 5-bromo-2-hydroxymethylbenzimidazole XXXV was prepared from 2-fluoro-5-bromonitrobenzene, XXXIV, using ammonium hydroxide (Scheme X).

Scheme X

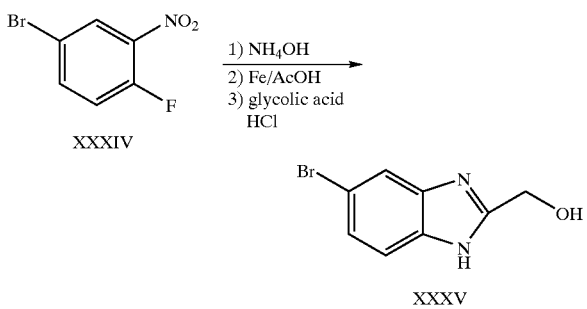

Compound XXXII can be further functionalized using palladium catalyzed reactions (Scheme XI). An aniline derivative XXXVIa (R=NH$_2$) can be prepared by palladium catalyzed addition of benzophenone imine to XXXII followed by hydroylsis of the benzophenone imine XXXVIb (R=N=Ph$_2$) to give XXXVIc. A Stille coupling can be used to produce a wide variety of carbon substituted derivatives such as the vinyl derivative XXXVIa (Scheme XI).

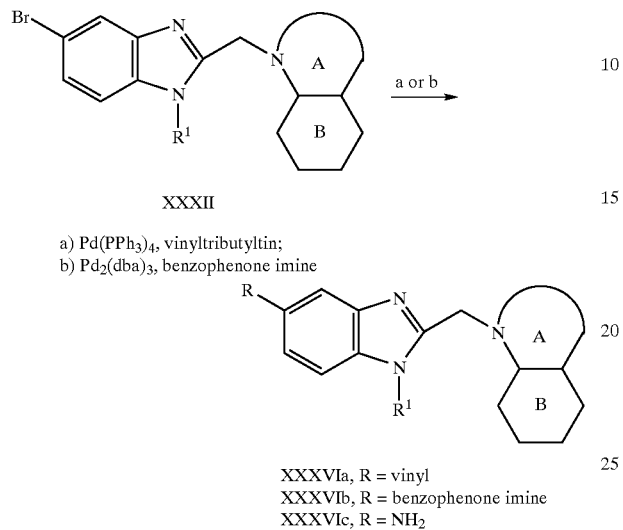

Scheme XI

XXXII a) Pd(PPh$_3$)$_4$, vinyltributyltin;
b) Pd$_2$(dba)$_3$, benzophenone imine XXXVIa, R = vinyl
XXXVIb, R = benzophenone imine
XXXVIc, R = NH$_2$ N-alkylation of 4-amino-3-nitrobenzonitrile provides an additional method for the preparation of 5-substituted benzimidazoles, XXXIX (Scheme XII). The 2-alkylamino-1-nitrobenzene XXXVIII is converted to benzimidazole XXXIX as before (see Scheme III).

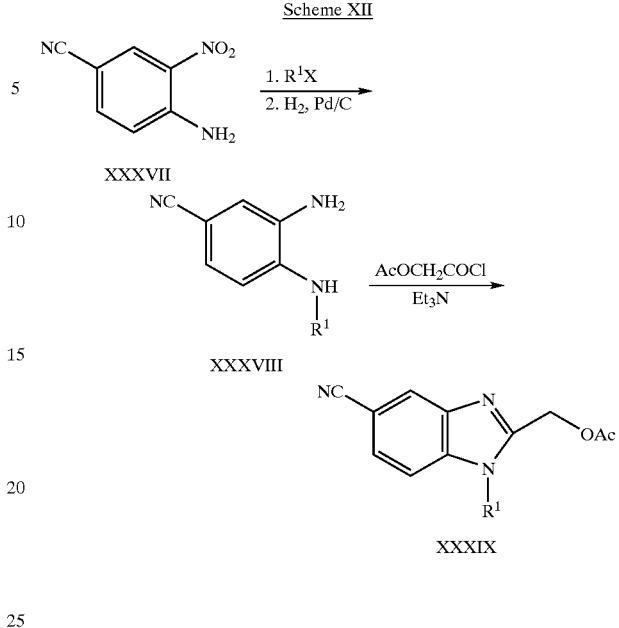

Scheme XII

XXXVII

XXXVIII

XXXIX

Nitrile XL can be reduced and the resulting amino alcohol XLI then protected as a t-butylcarbamate XLII. Compound XLII can also be converted to the chloride XLIII with SOCl$_2$ and used to N-alkylate a number of heterocycles to give XLIV. Monoalkyl amines XLVI are prepared from XLIV by treating the carbamate XLIV with a base such as sodium hydride followed by the addition of an alkylating agent (Scheme XIII).

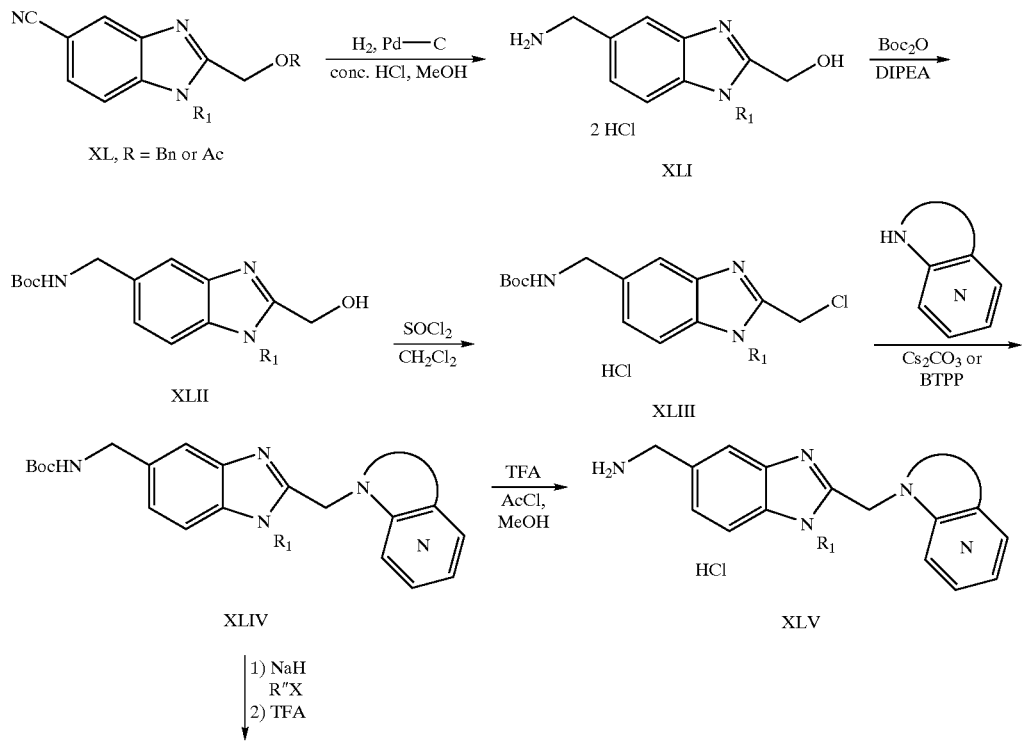

When R$_1$ contains a terminal alcohol group a sequence of protecting groups are used to simplify the synthesis of compounds of Formula I (Scheme XIV). The alcohol XLVII is converted to a pivalate ester XLVIII and benzyloxyacetyl chloride is used to prepare the benzimidazole XLVIII. The benzyl ether of XLVIII is removed during the reduction of the nitrile group. After protection of the primary amine with t-butylpyrocarbonate the 2-hydroxymethyl group (XLIX) is converted to the 2-chloromethyl group (L) with SOCl$_2$. The pivalate group of LIa is removed by hydrolysis with aqueous NaOH. The alcohol LIb can be converted to an alkyl fluoride LII using DAST.

Abbreviations Used in Schemes I–XIV and Experimental Section:

Ac: acetyl
AcOH: glacial acetic acid
BEMP: 2-tert-butylimino-2-diethylamino-1,3-dimethyl-perhydro-1,3,2-diazaphosphorine
BINAP: 2,2'-bis(diphenylphosphino)-1,1'-binaphthyl
Bn: benzyl
BOC: tert-butoxycarbonyl
Boc$_2$O: di-tert-butyl dicarbonate
BTPP: tert-butylimino-tri(pyrrolidino)phosphorane
CDI: 1,1'-carbonyldiimidazole
DAST: (diethylamino)sulfur trifluoride
DCM: dichloromethane
DIEA: N,N-diisopropylethylamine
DIPEA: N,N-diisopropylethylamine
DMAP: 4-(dimethylamino)pyridine
DMF: dimethylformamide
DMSO: dimethyl sulfoxide
EDC: 1-[3-(dimethylamino)propyl]-3-ethylcarbodiimide hydrochloride
EEDQ: 2-ethoxy-1-ethoxycarbonyl-1,2-dihydro-quinoline
EtOH: ethyl alcohol
EtOAc: ethyl acetate
Et$_2$O: diethyl ether
HOBT: 1-hydroxybenzotriazole hydrate
LAH: lithium aluminum hydride
MeCN: acetonitrile
MeOH: methyl alcohol
Pd$_2$(dba)$_3$: tris(dibenzylideneacetone)dipalladium(0)
Ph: phenyl
Piv: pivaloyl
PPh$_3$: triphenylphosphine
Prep HPLC: preparative high performance liquid chromatography
Satd.: saturated
TEA: triethylamine
TFA: trifluoroacetic acid
THF: tetrahydrofuran.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

Treatment is preferably commenced before or at the time of infection and continued until virus is no longer present in the respiratory tract. However, the treatment can also be commenced when given post-infection, for example after the appearance of established symptoms.

Suitable treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form, for example, containing 10 to 1500 mg, conveniently 20 to 1000 mg, most conveniently 50 to 700 mg of active ingredient per unit dosage form.

While it is possible that, for use in therapy, a compound of the invention may be administered as the raw chemical, it is preferable to present the active ingredient as a pharmaceutical formulation.

The invention thus further provides a pharmaceutical formulation comprising a compound of the Formula I, but not subject to the proviso thereto, or a pharmaceutically acceptable salt or derivative thereof together with a pharmaceutically acceptable carrier thereof.

The carrier must be "acceptable" in the sense of being compatible with the other ingredients of the formulation and not deleterious to the recipient thereof.

The pharmaceutical formulations may be in the form of conventional formulations for the intended mode of administration.

For intranasal administration according to the method of the invention the compounds of the invention may be administered by any of the methods and formulations employed in the art for intranasal administration.

Thus in general the compounds may be administered in the form of a solution or a suspension or as a dry powder.

Solutions and suspensions will generally be aqueous, for example prepared from water alone (for example sterile or pyrogen-free water), or water and a physiologically acceptable co-solvent (for example ethanol, propylene glycol, and polyethylene glycols such as PEG 400).

Such solutions or suspensions may additionally contain other excipients, for example, preservatives (such as benzalkonium chloride), solubilizing agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

Intranasal administration may also be achieved by means of an aerosol formulation in which the compound is provided in a pressurized pack with a suitable propellant such as a chlorofluorocarbon (CFC), for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Experimental Section

Proton nuclear magnetic resonance ($^1H$ NMR) spectra were recorded on a Bruker Avance 500, AC-300, Bruker DPX-300 or a Varian Gemini 300 spectrometer. All spectra were determined in $CDCl_3$, $CD_3OD$, d-acetone or DMSO-$d_6$ and chemical shifts are reported in δ units relative to tetramethylsilane (TMS). Splitting patterns are designated as follows: s, singlet; d, doublet; t, triplet; m, multiplet; b, broad peak; dd, doublet of doublets; dt, doublet of triplets; q, quartet; hept, heptet. Mass spectroscopy was performed on a Finnigan SSQ 7000 quadrupole mass spectrometer in both positive and negative electrospray ionization (ESI) modes or on a LC-MS using Shimadzu LC-10AS with micromass platform LC single quadrupole mass spectrometer in positive electrospray ionization. High resolution mass spectroscopy was recorded using Finnigan MAT 900. Infrared (IR) spectra were recorded on a Perkin-Elmer system 2000 FT-IR. Elemental analysis was performed with Perkin-Elmer series II, model 2400 CHN/O/S analyzer. Column chromatography was performed on silica gel from VWR Scientific. Alternatively the FLASH 12i™, FLASH 40i™ and FlashElute 65 modular systems from Biotage were used. Preparative HPLC was performed using a Shimadzu LC-8A on a C18 column eluted with a gradient of solvents A and B, where A is defined as 10% MeOH—90% water containing 0.1% trifluoroacetic acid, and B is defined as 90% MeOH—10% water containing 0.1% trifluoroacetic acid.

Preparation of Compounds of Formula I:

4-(3-Methyl-butylamino)-3-nitro-benzonitrile

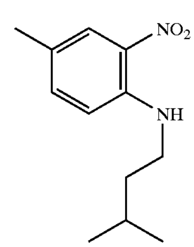

1

A solution of 4-chloro-3-nitrobenzonitrile (18.3 g, 0.10 mol) and isoamylamine (19.2 g, 0.22 mol) in DMF (250 mL) was heated to 90° C. for 4 h under nitrogen then cooled and the solvent evaporated. The residue is triturated with EtOAc (300 mL) and solids removed by filtration. The filtrate was washed with water and brine. The organic layer was dried over $MgSO_4$ and evaporated. The residue was recrystallized from MeOH to give 21.0 g (90%) of 4-(3-methyl-butylamino)-3-nitro-benzonitrile as a yellow crystalline solid.

$^1H$ NMR ($CDCl_3$) δ 0.99 (d, J=6.6 Hz, 6H), 1.63–1.68 (m, 2H), 1.76–1.78 (m, 1H), 3.34–3.38 (m, 2H), 6.91 (d, J=9.0 Hz, 1H), 7.59–7.61 (m, 1H), 8.36 (b, 1H), 8.51 (d, J=2.0 Hz, 1H);

MS m/e 234 ($MH^+$).

Acetic Acid 5-cyano-1-(3-methyl-butyl)-1H-benzoimidazol-2-ylmethyl Ester

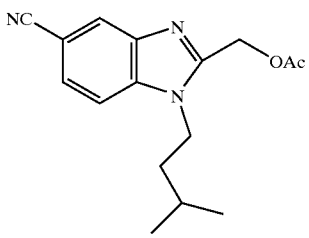

2

A mixture of 4-(3-methyl-butylamino)-3-nitro-benzonitrile (20.0 g, 85.7 mmol) and 10% palladium on carbon (1.0 g) in MeOH (100 mL) was placed in a Parr shaker under hydrogen (40 psi) for 2 h. The reaction mixture was filtered through celite, evaporated to dryness and the residue was used without further purification.

To a solution of this crude product (17.4 g, 85.7 mmol) and TEA (17.3 g, 171 mmol) in DCM (200 mL) was added acetoxyacetyl chloride (12.2 g, 90.0 mmol) drop-wise at 0° C. After stirring at ambient temperature for 2 h, the final solution was washed with water and brine. The organic layer was dried over MgSO$_4$ and evaporated. The residue was used without further purification.

A solution of this crude product in HOAc (50 mL) was heated to reflux for 30 min then the solvent removed. The residue was dissolved in EtOAc (200 mL) and washed with NaHCO$_3$ and brine. The organic layer was dried over MgSO$_4$ and evaporated. The residue was purified by flash chromatography (gradient, hexanes:EtOAc 2:1 to 1:1) to give 14.2 g (58% over three steps) of acetic acid 5-cyano-1-(3-methyl-butyl)-1H-benzoimidazol-2-ylmethyl ester as a white solid.

$^1$H NMR (CDCl$_3$) δ 1.02 (d, J=6.6 Hz, 6 H), 1.70–1.72 (m, 3 H), 2.16 (s, 3 H), 4.22 (t, J=7.7 Hz, 2 H), 5.38 (s, 2 H), 7.43 (d, J=8.4 Hz, 1 H), 7.57 (d, J=8.4 Hz, 1 H), 8.10 (s, 1 H);

MS m/e 286 (MH$^+$).

2-Chloromethyl-1-(3-methyl-butyl)-1H-benzoimidazole-5-carbonitrile

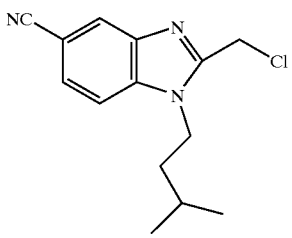

3

A mixture of acetic acid 5-cyano-1-(3-methyl-butyl)-1H-benzoimidazol-2 ylmethyl ester (7.0 g, 24.5 mmol) and K$_2$CO$_3$ (14 g, 101 mmol) in MeOH (100 mL) was stirred at ambient temperature for 2 h. The reaction mixture was diluted with EtOAc (100 mL) and filtered. The filtrate was evaporated and the residue dissolved in EtOAc (300 mL) and washed with water and brine. The organic layer was dried over MgSO$_4$ and evaporated. The residue was used without further purification.

To a solution of the crude product in DCM (100 mL) was added SOCl$_2$ (5.83 g, 49 mmol) at 0° C. and stirred for 30 min. The solvent was evaporated and the residue triturated with EtOAc, filtered and the solid washed with EtOAc to afford 6.6 g of 2-chloromethyl-1-(3-methyl-butyl)-1H-benzoimidazole-5-carbonitrile (90% over two steps) as a white solid.

$^1$H NMR (CD$_3$OD) δ 1.06 (d, J=6.0 Hz, 6H), 1.82–1.85 (m, 3H), 4.55 (t, J=7.9 Hz, 2H), 5.24 (s, 2H), 7.91 (d, J=8.6 Hz, 1H), 8.03 (d, J=8.6 Hz, 1H), 8.26 (s, 1H);

MS m/e 262 (MH$^+$).

1-Isopropyl-1,3-dihydro-benzoimidazol-2-one

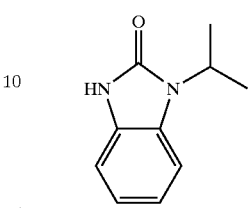

4

A mixture of 1-isopropenyl-1,3-dihydro-benzoimidazol-2-one (J. Davoll, J. Chem. Soc. 1960, 308) (6.90 g, 39.6 mmol) and 10% palladium on carbon (1.0 g) in MeOH (50 mL) was placed in a Parr shaker under hydrogen (40 psi) for 2 h. The reaction mixture was filtered through celite and evaporated to give 6.97 g (100%) of 1-isopropyl-1,3-dihydro-benzoimidazol-2-one as a white solid.

$^1$H NMR (CDCl$_3$) δ 1.57 (d, J=7.1 Hz, 6H), 4.70–4.81 (m, 1H), 7.02–7.10 (m, 2H), 7.10–7.20 (m, 2H);

MS m/e 177 (MH$^+$);

Anal. Calcd for C$_{10}$H$_{12}$N$_2$O: C, 68.16; H, 6.86; N, 15.90; Found: C, 68.05; H, 6.63; N, 15.77.

2-(3-Isopropyl-2-oxo-2,3-dihydro-benzoimidazol-1-ylmethyl)-1-(3-methyl-butyl)-1H-benzoimidazole-5-carbonitrile

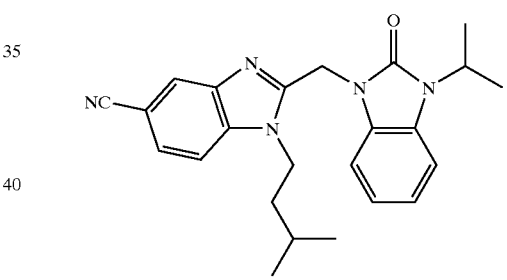

5

A suspension of 1-isopropyl-1,3-dihydro-benzoimidazol-2-one (0.79 g, 4.5 mmol) and Cs$_2$CO$_3$ (4.40 g, 13.5 mmol) in DMF (50 mL) was stirred for 30 minutes then 2-chloromethyl-1-(3-methyl-butyl)-1H-benzoimidazole-5-carbonitrile (1.34 g, 4.5 mmol) was added and the mixture stirred for 5 h at ambient temperature. The reaction mixture was diluted with EtOAc (50 mL) and filtered. The filtrate was evaporated to dryness and the residue taken up in EtOAc (100 mL), washed with water and brine. The organic layer was dried over MgSO$_4$ and evaporated. The residue was purified by flash chromatography (gradient, hexanes:EtOAc 3:1 to 1:1) to give 1.71 g (95%) of 2-(3-isopropyl-2-oxo-2,3-dihydro-benzoimidazol-1-ylmethyl)-1-(3-methyl-butyl)-1H-benzoimidazole-5-carbonitrile as a white solid.

$^1$H NMR (CDCl$_3$) δ: 0.96 (d, J=6.6 Hz, 6H), 1.42–1.47 (m, 2 H), 1.55 (d, J=7.0 Hz, 6H), 1.68–1.72 (m, 1H), 4.36 (t, J=8.1 Hz, 2H), 4.73–4.78 (m, 1H), 5.38 (s, 2H), 7.03–7.09 (m, 2H), 7.13–7.14 (m, 1H), 7.36–7.42 (m, 2H), 7.52–7.54 (m, 1H), 8.12 (s, 1H);

MS m/e 402 (MH$^+$).

1-[5-Aminomethyl-1-(3-methyl-butyl)-1H-benzoimidazol-2-ylmethyl]-3-isopropyl-1,3-dihydro-benzoimidazol-2-one

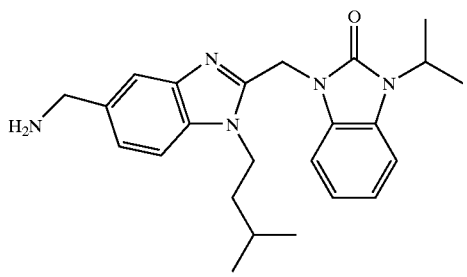

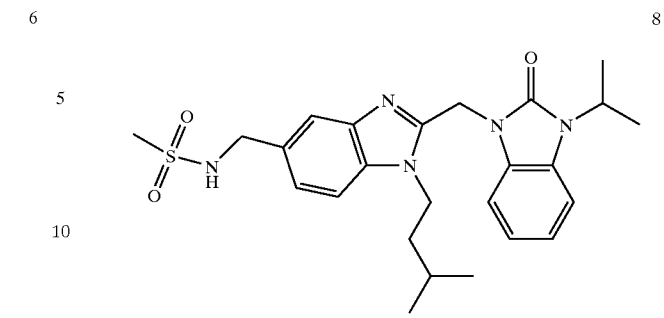

A mixture of 2-(3-isopropyl-2-oxo-2,3-dihydro-benzoimidazol-1-ylmethyl)-1-(3-methyl-butyl)-1H-benzoimidazole-5-carbonitrile (230 mg, 0.57 mmol) and 10% palladium on carbon (50 mg) in 5% HCl-MeOH (10 mL) was placed in a Parr shaker under hydrogen (40 psi) for 6 h. The reaction mixture was filtered through celite and the solvent evaporated. The residue was purified by prep-HPLC (gradient 10% –100% B) to give 148 mg (64%) of 1-[5-aminomethyl-1-(3-methyl-butyl)-1H-benzoimidazol-2-ylmethyl]-3-isopropyl-1,3-dihydro-benzoimidazol-2-one as a hygroscopic white solid.

$^1$H NMR (CD$_3$OD) δ 0.94 (d, J=6.5 Hz, 6H), 1.53–1.58 (m, 8H), 1.66–1.70 (m, 1H), 4.28 (s, 2 H), 4.47 (t, J=8.2 Hz, 2H), 4.71–4.75 (m, 1H), 5.58 (s, 2H), 7.09 (t, J=7.8 Hz, 1H), 7.16 (t, J=7.8 Hz, 1 H), 7.22 (d, J=7.8 Hz, 1 H), 7.37 (d, J=7.9 Hz, 1H), 7.59 (d, J=8.4 Hz, 1H), 7.78 (d, J=8.5 Hz, 1H), 7.84 (s, 1H);

MS m/e 406 (MH$^+$).

N-[2-(3-Isopropyl-2-oxo-2,3-dihydro-benzoimidazol-1-ylmethyl)-1-(3-methyl-butyl)-1H-benzoimidazol-5-ylmethyl]-acetamide

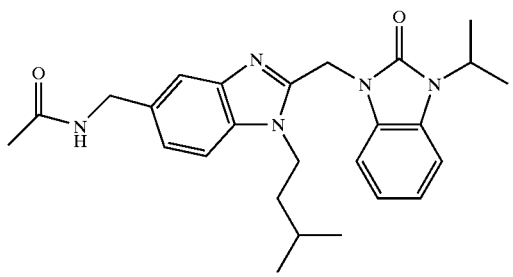

To a solution of 1-[5-aminomethyl-1-(3-methyl-butyl)-1H-benzoimidazol-2-ylmethyl]-3-isopropyl-1,3-dihydro-benzoimidazol-2-one (20 mg, 0.05 mmol) and TEA (10 mg, 0.10 mmol) in THF (2 ml) was added acetyl chloride (5 mg, 0.06 mmol) at room temperature and the reaction mixture was stirred for 12 h. After evaporation, the residue was purified by prep-HPLC (gradient 10%–100% B) to afford 18 mg (80%) of N-[2-(3-isopropyl-2-oxo-2,3-dihydro-benzoimidazol-1-ylmethyl)-1-(3-methyl-butyl)-1H-benzoimidazol-5-ylmethyl]-acetamide as a colorless gum.

$^1$H NMR (CD$_3$OD) δ 0.94 (d, J=6.5 Hz, 6H), 1.56–1.64 (m, 8H), 1.68–1.71 (m, 1H), 1.99–2.01 (m, 3H), 4.48–4.51 (m, 4H), 4.70–4.75 (m, 1H), 5.65 (s, 2H), 7.12–7.26 (m, 3H), 7.39–7.41 (m, 1H), 7.55–7.57 (m, 1H), 7.65 (s, 1H), 7.78–7.80 (m, 1H);

MS m/e 448 (MH$^+$).

N-[2-(3-Isopropyl-2-oxo-2,3-dihydro-benzoimidazol-1-ylmethyl)-1-(3-methyl-butyl)-1H-benzoimidazol-5-ylmethyl]-methanesulfonamide N-[2-(3-Isopropyl-2-oxo-2,3-dihydro-benzoimidazol-1-ylmethyl)-1-(3-methyl-butyl)-1H-benzoimidazol-5-ylmethyl]-methanesulfonamide was prepared by the same procedure as N-[2-(3-isopropyl-2-oxo-2,3-dihydro-benzoimidazol-1-ylmethyl)-1-(3-methyl-butyl)-1H-benzoimidazol-5-ylmethyl]-acetamide, except using methanesulfonyl chloride.

$^1$H NMR (CD$_3$OD) δ 0.95 (d, J=6.5 Hz, 6H), 1.57 (d, J=7.0 Hz, 6H), 1.61–1.72 (m, 3H), 2.92 (d, J=4.1 Hz, 3H), 4.43 (s, 2H), 4.52 (t, J=8.4 Hz, 2H), 4.71–4.74 (m, 1H), 5.67 (s, 2 H), 7.13–7.22 (m, 2 H), 7.26 (d, J=7.8 Hz, 1H), 7.40 (d, J=7.7 Hz, 1H), 7.64–7.66 (m, 1H), 7.77 (s, 1 H), 7.83 (d, J=8.6 Hz, 1H);

MS m/e 484 (MH$^+$).

2-(3-Isopropyl-2-oxo-2,3-dihydro-benzoimidazol-1-ylmethyl)-1-(3-methyl-butyl)-1H-benzoimidazole-5-carboxylic Acid

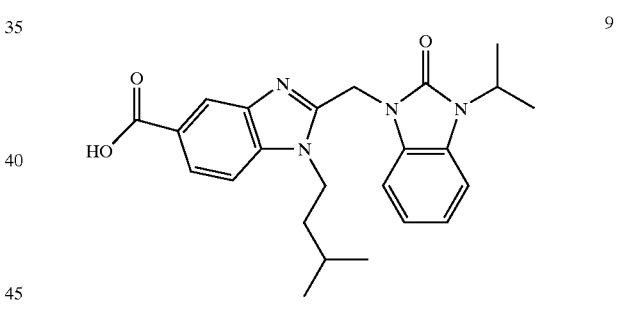

A mixture of 2-(3-isopropyl-2-oxo-2,3-dihydro-benzoimidazol-1-ylmethyl)-1-(3-methyl-butyl)-1H-benzoimidazole-5-carbonitrile (2.00 g, 5.0 mmol) and 6M HCl (50 mL) was heated to reflux for 12 h. After cooling, the final solution was neutralized by ammonium hydroxide and 1M NaOH to pH 6. The precipitate was collected by filtration and the solid washed with water thoroughly and dried in a vacuum oven to yield 1.74 g (83%) of 2-(3-isopropyl-2-oxo-2,3-dihydro-benzoimidazol-1-ylmethyl)-1-(3-methyl-butyl)-1H-benzoimidazole-5 carboxylic acid as a white solid.

$^1$H NMR (DMSO-d$_6$) δ: 0.89 (d, J=6.6 Hz, 6H), 1.35–1.40 (m, 2H), 1.48 (d, J=7.0 Hz, 6H), 1.60–1.70 (m, 1 H), 4.30 (t, J=7.9 Hz, 2H), 4.65–4.70 (m, 1H), 5.36 (s, 2H), 6.98–7.05 (m, 2H), 7.24 (d, J=7.6 Hz, 1 H), 7.34 (d, J=7.6 Hz, 1H), 7.48 (d, J=8.5 Hz, 1H), 7.86 (d, J=8.5 Hz, 1H), 8.14 (s, 1H);

MS m/e 421 (MH$^+$).

1-[5-Hydroxymethyl-1-(3-methyl-butyl)-1H-benzoimidazol-2-ylmethyl]-3-isopropyl-1,3-dihydro-benzoimidazol-2-one

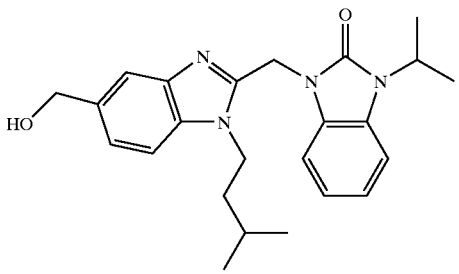

10

To a mixture of 2-(3-isopropyl-2-oxo-2,3-dihydro-benzoimidazol-1-ylmethyl)-1-(3-methyl-butyl)-1H-benzoimidazole-5 carboxylic acid (570 mg, 1.36 mmol) and MeOH (5 mL) was added conc. $H_2SO_4$ (160 mg, 1.63 mmol). The final solution was heated to reflux for 12 h. After cooling, the solution was diluted with EtOAc and washed with sat. $NaHCO_3$ and 1M NaOH, and brine. The organic layer was dried over $MgSO_4$ and evaporated to give 470 mg (80%) of the ester as a white solid. The product was used without further purification.

To a solution of the ester mentioned above (430 mg, 1.0 mmol) in THF (10 mL) was added LAH (1M in THF, 1.2 mL) at 0° C. After stirring for 10 min, the reaction solution was quenched with EtOAc and was washed with aqueous Rochelle's salt and aqueous brine. The organic layer was dried over $MgSO_4$ and evaporated. The residue was purified by flash chromatography (hexanes:acetone 1:1) to give 310 mg (76%) of 1-[5-hydroxymethyl-1-(3-methyl-butyl)-1H-benzoimidazol-2-ylmethyl]-3-isopropyl-1,3-dihydro-benzoimidazol-2-one as a white solid.

$^1$H NMR ($CD_3OD$) δ 0.92 (d, J=6.5 Hz, 6 H), 1.40–1.44 (m, 2 H), 1.58 (d, J=7.0 Hz, 6 H), 1.63–1.69 (m, 1 H), 4.32 (t, J=8.0 Hz, 2 H), 4.69 (s, 2 H), 4.70–4.78 (m, 1 H), 5.40 (s, 2 H), 7.00–7.02 (m, 1 H), 7.07–7.11 (m, 1 H), 7.15 (d, J=7.6 Hz, 1 H), 7.30–7.34 (m, 2 H), 7.44 (d, J=8.4 Hz, 1 H), 7.65 (s, 1 H);

MS m/e 407 (MH$^+$).

2-(3-Isopropyl-2-oxo-2,3-dihydro-benzoimidazol-1-ylmethyl)-1-(3-methyl-butyl)-1H-benzoimidazole-5-carboxylic Acid Dimethylamide

11

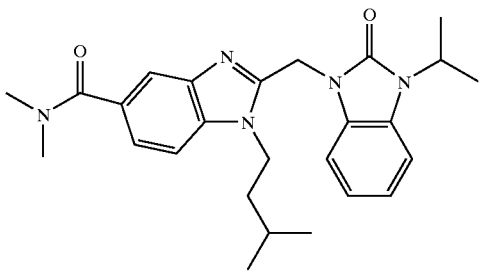

A mixture of 2-(3-isopropyl-2-oxo-2,3-dihydro-benzoimidazol-1-ylmethyl)-1-(3-methyl-butyl)-1H-benzoimidazole-5 carboxylic acid (42 mg, 0.1 mmol), EDC (23 mg, 0.12 mmol), DMAP (14 mg, 0.12 mmol) and dimethylamine (1M in THF, 0.12 mL) was stirred for 12 h at ambient temperature. The solvent was evaporated and the residue purified by prep-HPLC (gradient 10%–100% B) to give 22 mg (49%) of 2-(3-isopropyl-2-oxo-2,3-dihydro-benzoimidazol-1-ylmethyl)-1-(3-methyl-butyl)-1H-benzoimidazole-5-carboxylic acid dimethylamide as a white solid.

$^1$H NMR ($CD_3OD$) δ: 0.96 (d, J=6.6 Hz, 6 H), 1.57 (d, J=6.9 Hz, 6 H), 1.60–1.65 (m, 2 H), 1.66–1.74 (m, 1 H), 3.00 (s, 3 H), 3.13 (s, 3 H), 4.51 (t, J=8.3 Hz, 2 H), 4.70–4.76 (m, 1 H), 5.63 (s, 2 H), 7.10–7.13 (m, 1 H), 7.16–7.19 (m, 1 H), 7.25 (d, J=7.8 Hz, 1 H), 7.38 (d, J=7.9 Hz, 1 H), 7.59 (d, J=8.6 Hz, 1 H), 7.65 (s, 1 H), 7.83 (d, J=8.5 Hz, 1 H);

MS m/e 448 (MH$^+$).

2-(3-Isopropyl-2-oxo-2,3-dihydro-benzoimidazol-1-ylmethyl)-1-(3-methyl-butyl)-1H-benzoimidazole-5-carboxylic Acid Amide

12

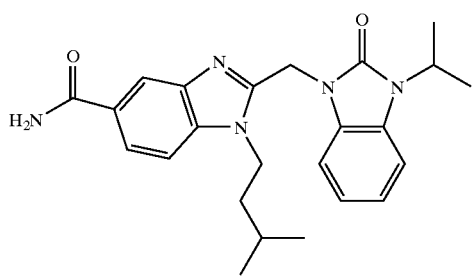

2-(3-Isopropyl-2-oxo-2,3-dihydro-benzoimidazol-1-ylmethyl)-1-(3-methyl-butyl)-1H-benzoimidazole-5-carboxylic acid amide was prepared by the same procedure as 2-(3-isopropyl-2-oxo-2,3-dihydro-benzoimidazol-1-ylmethyl)-1-(3-methyl-butyl)-1H-benzoimidazole-5-carboxylic acid dimethylamide, except using ammonium hydroxide.

$^1$H NMR ($CD_3OD$) δ 0.95 (d, J=6.6 Hz, 6 H), 1.57 (d, J=6.9 Hz, 6 H), 1.59–1.63 (m, 2 H), 1.66–1.73 (m, 1 H), 4.49 (t, J=8.3 Hz, 2 H), 4.70–4.75 (m, 1 H), 5.63 (s, 2 H), 7.10–7.13 (m, 1 H), 7.15–7.19 (m, 1 H), 7.25 (d, J=7.8 Hz, 1 H), 7.37 (d, J=7.9 Hz, 1 H), 7.81 (d, J=8.7 Hz, 1 H), 8.04–8.06 (m, 1 H), 8.23 (s, 1 H);

MS m/e 420 (MH$^+$).

Methanesulfonic Acid 2-(3-isopropyl-2-oxo-2,3-dihydro-benzoimidazol-1-ylmethyl)-1-(3-methyl-butyl)-1H-benzoimidazol-5-ylmethyl Ester

13

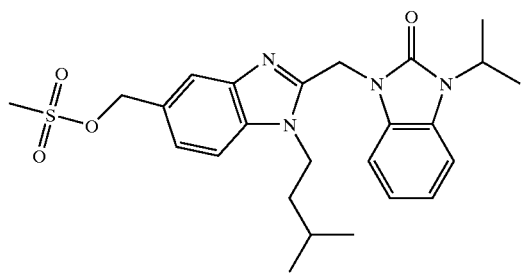

To a solution of 1-[5-hydroxymethyl-1-(3-methyl-butyl)-1H-benzoimidazol-2-ylmethyl]-3-isopropyl-1,3-dihydro-benzoimidazol-2-one (155 mg, 0.38 mmol) and TEA (130 mg, 1.14 mmol) in DCM (5 mL) was added methanesulfonyl chloride (87 mg, 0.76 mmol) at 0° C. The final solution was stirred at ambient temperature for 12 h then washed with sat. $NaHCO_3$ and brine. The organic layer was dried with $MgSO_4$ and evaporated. The residue was purified by flash chromatography (hexanes:EtOAc 2:1 to 1:1) to give 62 mg (33%) of methanesulfonic acid 2-(3-isopropyl-2-oxo-2,3-dihydro-benzoimidazol-1-ylmethyl)-1-(3-methyl-butyl)-1H-benzoimidazol-5-ylmethyl ester as a white solid.

$^1$H NMR ($CD_3OD$) δ 0.95 (d, J=6.6 Hz, 6 H), 1.49–1.55 (m, 2 H), 1.58 (d, J=6.9 Hz, 6 H), 1.63–1.69 (m, 1 H), 3.14

(s, 3 H), 4.33 (t, J=8.0 Hz, 2 H), 4.74 (s, 2 H), 4.75–4.78 (m, 1 H), 5.37 (s, 2 H), 6.98–7.02 (m, 2 H), 7.09–7.12 (d, J=7.6 Hz, 1 H), 7.28–7.32 (m, 2 H), 7.42 (d, J=8.2 Hz, 1 H), 7.79 (s, 1 H);

1-Isopropyl-3-[5-methylaminomethyl-1-(3-methyl-butyl)-1H-benzoimidazol-2-ylmethyl]-1,3-dihydro-benzoimidazol-2-one

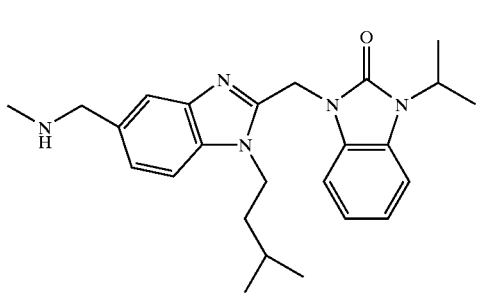

14

A mixture of methanesulfonic acid 2-(3-isopropyl-2-oxo-2,3-dihydro-benzoimidazol-1-ylmethyl)-1-(3-methyl-butyl)-1H-benzoimidazol-5-ylmethyl ester (10 mg, 0.02 mmol) and methylamine (1M in THF, 0.5 mL) was stirred at ambient temperature for 12 h then the solvent evaporated. The residue was purified by prep-HPLC (gradient 10%–100% B) to give 8.1 mg (94%) of 1-[5-methylaminomethyl-1-(3-methyl-butyl)-1H-benzoimidazol-2-ylmethyl]-3-isopropyl-1,3-dihydro-benzoimidazol-2-one as a colorless gum.

$^1$H NMR (CD$_3$OD) δ 0.94 (d, J=6.6 Hz, 6 H), 1.49–1.54 (m, 2 H), 1.58 (d, J=7.0 Hz, 6 H), 1.66–1.70 (m, 1 H), 2.72 (s, 3 H), 4.32 (s, 2 H), 4.43 (t, J=7.0 Hz, 2 H), 4.72–4.75 (m, 1 H), 5.51 (s, 2 H), 7.05–7.07 (m, 1 H), 7.12–7.15 (m, 1 H), 7.19 (d, J=7.8 Hz, 1 H), 7.35 (d, J=7.9 Hz, 1 H), 7.50–7.51 (m, 1 H), 7.69 (d, J=8.4 Hz, 1 H), 7.81 (s, 1 H);

MS m/e 420 (MH$^+$).

1-[5-Cyclopropylaminomethyl-1-(3-methyl-butyl)-1H-benzoimidazol-2-ylmethyl]-3-isopropyl-1,3-dihydro-benzoimidazol-2-one

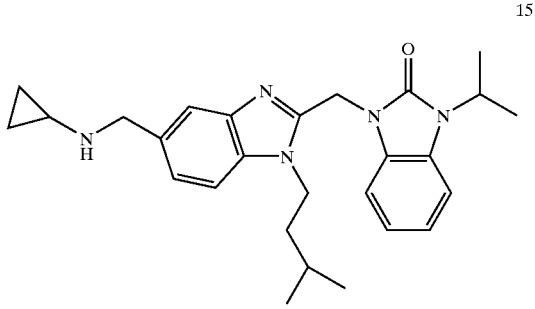

15

1-[5-Cyclopropylaminomethyl-1-(3-methyl-butyl)-1H-benzoimidazol-2-ylmethyl]-3-isopropyl-1,3-dihydro-benzoimidazol-2-one was prepared by the same procedure as 1-[5-methylaminomethyl-1-(3-methyl-butyl)-1H-benzoimidazol-2-ylmethyl]-3-isopropyl-1,3-dihydro-benzoimidazol-2-one, except using cyclopropylamine.

$^1$H NMR (CD$_3$OD) δ 0.85–0.89 (m, 2 H), 0.90–0.92 (m, 2 H), 0.94 (d, J=6.6 Hz, 6 H), 1.46–1.50 (m, 2 H), 1.58 (d, J=7.0 Hz, 6 H), 1.65–1.69 (m, 1 H), 2.76–2.79 (m, 1 H), 4.39 (t, J=7.0 Hz, 2 H), 4.42 (s, 2 H), 4.73–4.77 (m, 1 H), 5.45 (s, 2 H), 7.00–7.03 (m, 1 H), 7.10–7.13 (m, 1 H), 7.16 (d, J=7.8 Hz, 1 H), 7.33 (d, J=7.9 Hz, 1 H), 7.44–7.46 (m, 1 H), 7.61 (d, J=8.4 Hz, 1 H), 7.79 (s, 1 H);

MS m/e 446 (MH$^+$).

[2-(3-Isopropyl-2-oxo-2,3-dihydro-benzoimidazol-1-ylmethyl)-1-(3-methyl-butyl)-1H-benzoimidazol-5-yl]-acetonitrile

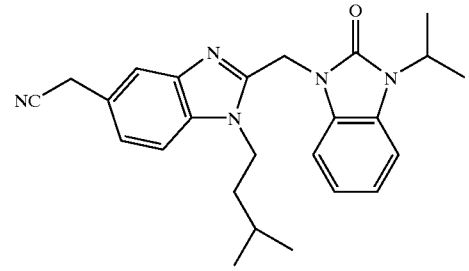

16

A mixture of methanesulfonic acid 2-(3-isopropyl-2-oxo-2,3-dihydro-benzoimidazol-1-ylmethyl)-1-(3-methyl-butyl)-1H-benzoimidazol-5-ylmethyl ester (16 mg, 0.033 mmol) and KCN (21 mg, 0.33 mmol) in DMF was stirred for 24 h at ambient temperature. The solvent was evaporated and the residue was purified by prep-HPLC (gradient 10%–100% B) to give 12 mg (88%) of [2-(3-isopropyl-2-oxo-2,3-dihydro-benzoimidazol-1-ylmethyl)-1-(3-methyl-butyl)-1H-benzoimidazol-5-yl]-acetonitrile as a colorless gum.

$^1$H NMR (CD$_3$OD) δ 0.95 (d, J=6.6 Hz, 6 H), 1.56 (d, J=7.0 Hz, 6 H), 1.59–1.63 (m, 2 H), 1.67–1.71 (m, 1 H), 4.10 (s, 2 H), 4.49 (t, J=7.0 Hz, 2 H), 4.71–4.74 (m, 1 H), 5.63 (s, 2 H), 7.11–7.14 (m, 1 H), 7.17–7.20 (m, 1 H), 7.25 (d, J=7.6 Hz, 1 H), 7.38 (d, J=7.9 Hz, 1 H), 7.57 (d, J=8.0 Hz, 1 H), 7.75 (s, 1 H), 7.81 (d, J=8.6 Hz, 1 H);

MS m/e 416 (MH$^+$).

1-[5-(2-Amino-ethyl)-1-(3-methyl-butyl)-1H-benzoimidazol-2-ylmethyl]-3-isopropyl-1,3-dihydro-benzoimidazol-2-one

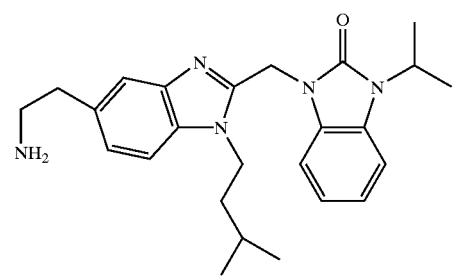

17

1-[5-(2-Amino-ethyl)-1-(3-methyl-butyl)-1H-benzoimidazol-2-ylmethyl]-3-isopropyl-1,3-dihydro-benzoimidazol-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one, except using [2-(3-isopropyl-2-oxo-2,3-dihydro-benzoimidazol-1-ylmethyl)-1-(3-methyl-butyl)-1H-benzoimidazol-5-yl]-acetonitrile.

$^1$H NMR (CD$_3$OD) δ 0.93 (d, J=6.6 Hz, 6 H), 1.53–1.59 (m, 8 H), 1.65–1.69 (m, 1 H), 3.13 (t, J=7.6 Hz, 2 H), 3.24 (t, J=7.5 Hz, 2 H), 4.47 (t, J=8.3 Hz, 2 H), 4.70–4.73 (m, 1 H), 5.62 (s, 2 H), 7.10–7.13 (m, 1 H), 7.16–7.18 (m, 1 H), 7.24 (d, J=7.8 Hz, 1 H), 7.38 (d, J=7.8 Hz, 1 H), 7.48–7.50 (m, 1 H), 7.66 (s, 1 H), 7.75 (d, J=8.6 Hz, 1 H);

MS m/e 420 (MH$^+$).

1-[5-Fluoromethyl-1-(3-methyl-butyl)-1H-benzoimidazol-2-ylmethyl]-3-isopropyl-1,3-dihydro-benzoimidazol-2-one

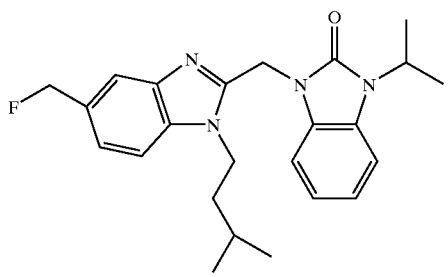

18

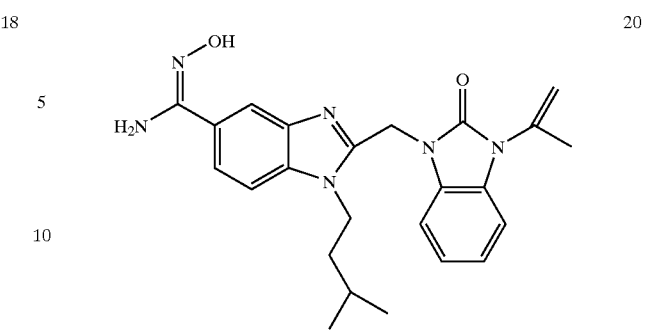

20

To a solution of 1-[5-hydroxymethyl-1-(3-methyl-butyl)-1H-benzoimidazol-2-ylmethyl]-3-isopropyl-1,3-dihydro-benzoimidazol-2-one (41 mg, 0.10 mmol) in DCM (1 mL) was added DAST (32 mg, 0.20 mmol) at 0° C. The final solution was stirred at ambient temperature for 12 h then washed with sat. NaHCO$_3$ and brine. The organic layer was dried over MgSO$_4$ and evaporated. The residue was purified by slash chromatography (hexanes:EtOAc 2:1 to 1:1) to give 32 mg (78%) of 1-[5-fluoromethyl-1-(3-methyl-butyl)-1H-benzoimidazol-2-ylmethyl]-3-isopropyl-1,3-dihydro-benzoimidazol-2-one as a white solid.

$^1$H NMR (CDCl$_3$) δ 0.94 (d, J=6.6 Hz, 6 H), 1.37–1.42 (m, 2 H), 1.55 (d, J=7.0 Hz, 6 H), 1.64–1.70 (m, 1 H), 4.30 (t, J=8.1 Hz, 2 H), 4.73–4.79 (m, 1 H), 5.38 (s, 2 H), 5.48 (d, J=48 Hz, 2 H), 6.97–6.07 (m, 2 H), 7.10–7.13 (m, 1 H), 7.32 (s, 2 H), 7.40–7.43 (m, 1 H), 7.81 (s, 1 H);

MS m/e 409 (MH$^+$).

2-(3-Isopropenyl-2-oxo-2,3-dihydro-benzoimidazol-1-ylmethyl)-1-(3-methyl-butyl)-1H-benzoimidazole-5-carbonitrile

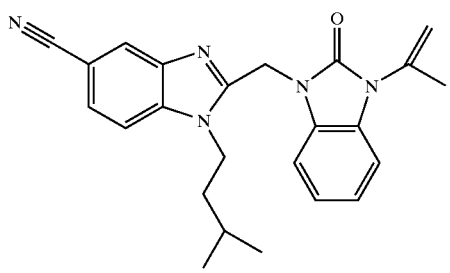

19

2-(3-Isopropenyl-2-oxo-2,3-dihydro-benzoimidazol-1-ylmethyl)-1-(3-methyl-butyl)-1H-benzoimidazole-5-carbonitrile was prepared as described for 2-(3-Isopropyl-2-oxo-2,3-dihydro-benzoimidazol-1-ylmethyl)-1-(3-methyl-butyl)-1H-benzoimidazole-5-carbonitrile using 2-chloromethyl-1-(3-methyl-butyl)-1H-benzoimidazole-5-carbonitrile and 1-Isopropenyl-1,3-dihydro-benzoimidazol-2-one with NaH as base.

$^1$H NMR (CDCl$_3$) δ: 0.98 (d, J=6.6 Hz, 6H), 1.30–1.48 (m, 2H), 1.68–1.81 (m, 1H), 2.26 (s, 3H), 4.33–4.42 (m, 2H), 5.23 (s, 1H), 5.41–5.42 (m, 3H), 7.08–7.12 (m, 3H), 7.40 (d, J=8.3 Hz, 1H), 7.43–7.46 (m, 2H), 7.55 (d, J=7.0 Hz, 1H), 8.14 (s, 1H);

MS m/e 399 (MH$^+$).

N-Hydroxy-2-(3-isopropenyl-2-oxo-2,3-dihydro-benzoimidazol-1-ylmethyl)-1-(3-methyl-butyl)-1H-benzoimidazole-5-carboxamidine 2-(3-Isopropenyl-2-oxo-2,3-dihydro-benzoimidazol-1-ylmethyl)-1-(3-methyl-butyl)-1H-benzoimidazole-5-carbonitrile (110 mg, 0.275 mmol) was treated with hydroxylaminehydrochloride (57 mg, 0.275 mmol), K$_2$CO$_3$ (55.3 mg, 0.4 mmol) and heated to reflux in EtOH(10 ml) for 6 h. The solvent was removed and the residue dissolved in CH$_2$Cl$_2$ and washed with H$_2$O. The solvent was removed to give 31 mg (26%) of N-hydroxy-2-(3-isopropenyl-2-oxo-2,3-dihydro-benzoimidazol-1-ylmethyl)-1-(3-methyl-butyl)-1H-benzoimidazole-5-carboxamidine as a white solid.

$^1$H NMR (CD$_3$OD) δ: 0.96 (d, J=6.6 Hz, 6H), 1.45–1.52 (m, 2H), 1.66–1.75 (m, 1H), 2.26 (s, 3H), 4.37–4.43 (m, 2H), 5.27 (s, 1H), 5.47–5.49 (m, 3H), 7.06–7.22 (m, 4H), 7.53 (d, J=8.1 Hz, 1H), 7.64 (dd, J=1.6, 8.5 Hz, 1H), 7.95 (s, 1H);

MS m/e 432 (MH$^+$).

2-(3-Isopropenyl-2-oxo-2,3-dihydro-benzoimidazol-1-ylmethyl)-1-(3-methyl-butyl)-1H-benzoimidazole-5-carboxamidine

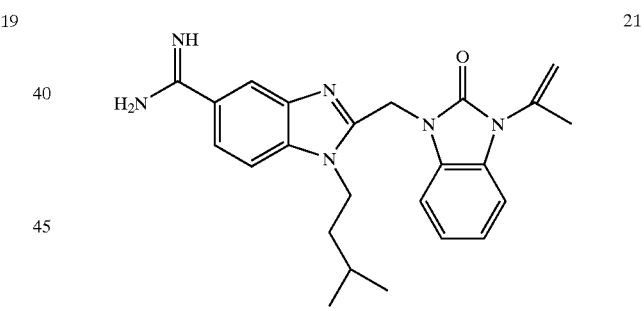

21

A solution of N-hydroxy-2-(3-isopropenyl-2-oxo-2,3-dihydro-benzoimidazol-1-ylmethyl)-1-(3-methyl-butyl)-1H-benzoimidazole-5-carboxamidine (110 mg, 0.754 mmol) was dissolved in AcOH (10 ml) and 10% Pd/C added. The mixture was shaken on a Parr hydrogenator at 50 psi for 4 h. The catalyst was removed by filtration and the solid washed with AcOH. The acetic acid was removed and the solid triturated with ether to give the product 90 mg (86%) as a white solid.

$^1$H NMR (DMSO-d6) δ: 0.91 (d, J=6.6 Hz, 6H), 1.42–1.50 (m, 2H), 1.60–1.68 (m, 1H), 1.80 (s, 3H), 2.19 (s, 3H), 4.34–4.40 (m, 2H), 5.20 (s, 1H), 5.44–5.45 (m, 3H), 7.07–7.18 (m, 2H), 7.19–7.21 (m, 2H), 7.71–7.77 (m, 3H), 8.14 (s, 1H);

MS m/e 416 (MH$^+$).

1-(3-Methyl-butyl)-2-(2-oxo-2,3-dihydro-benzoimidazol-1-ylmethyl)-1H-benzoimidazole-5-carboxamidine

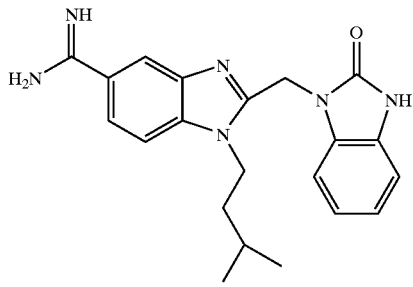

22

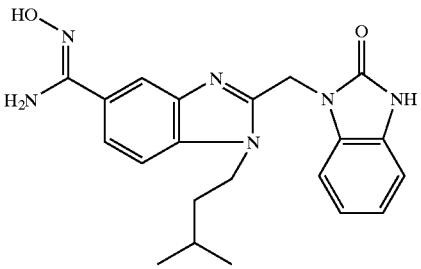

24

2-(3-Isopropenyl-2-oxo-2,3-dihydro-benzoimidazol-1-ylmethyl)-1-(3-methyl-butyl)-1H-benzoimidazole-5-carboxamidine (20 mg, 0.05 mmol) was dissolved in 30% TFA/CH$_2$Cl$_2$ and stirred at reflux for 1 h. The solvent was removed and the residues triturated with ether to give 18 mg (99%) of 1-(3-methyl-butyl)-2-(2-oxo-2,3-dihydro-benzoimidazol-1-ylmethyl)-1H-benzoimidazole-5-carboxamidine as a white solid as the TFA salt.

$^1$H NMR (CD$_3$OD) δ: 0.98 (d, J=6.6 Hz, 6H), 1.46–1.51 (m, 2H), 1.61–1.77 (m, 1H), 4.41–4.49 (m, 2H), 4.80–4.96 (m, 2H), 5.53 (s, 2H), 6.99–7.35 (m, 4H), 7.77–7.80 (m,2H), 8.18 (s, 1H);

MS m/e 376 (MH$^+$).

1-(3-Methyl-butyl)-2-(2-oxo-2,3-dihydro-benzoimidazol-1-ylmethyl)-1H-benzoimidazole-5-carbonitrile

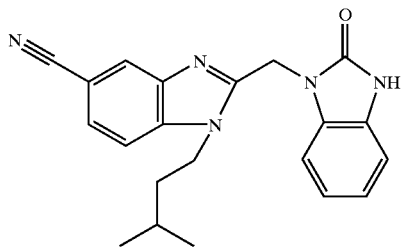

23

The isopropenyl group of 1-(3-methyl-butyl)-2-(2-oxo-2,3-dihydro-benzoimidazol-1-ylmethyl)-1H-benzoimidazole-5-carbonitrile was removed as described for 1-(3-methyl-butyl)-2-(2-oxo-2,3-dihydro-benzoimidazol-1-ylmethyl)-1H-benzoimidazole-5-carboxamidine.

$^1$H NMR (DMSO-d6) d: 0.94 (d, J=6.6 Hz, 6H), 1.34–1.42 (m, 2H), 1.68–1.73 (m, 1H), 4.35–4.41 (m, 2H), 5.44 (s, 2H), 6.99–7.13 (m, 4H), 7.59–7.67 (m, 2H0, 8.03 (s, 1H);

MS m/e 359 (MH$^+$).

N-Hydroxy-1-(3-methyl-butyl)-2-(2-oxo-2,3-dihydro-benzoimidazol-1-ylmethyl)-1H-benzoimidazole-5-carboxamidine N-Hydroxy-1-(3-methyl-butyl)-2-(2-oxo-2,3-dihydro-benzoimidazol-1-ylmethyl)-1H-benzoimidazole-5-carboxamidine was prepared from 1-(3-Methyl-butyl)-2-(2-oxo-2,3-dihydro-benzoimidazol-1-ylmethyl)-1H-benzoimidazole-5-carbonitrile as described for N-hydroxy-2-(3-isopropenyl-2-oxo-2,3-dihydro-benzoimidazol-1-ylmethyl)-1-(3-methyl-butyl)-1H-benzoimidazole-5-carboxamidine.

$^1$H NMR (DMSO-d6) d: 0.90 (d, J=6.6 Hz, 6H), 1.33–1.40 (m, 2H), 1.63–1.67 (m, 2H), 4.27–4.33 (m, 2H), 5.33 (s, 2H), 5.81 (br s 1H), 6.9–7.03 (m, 2H), 7.13 (d, J=6.9 Hz, 1H), 7.47 (d, J=8.4 Hz, 1H), 7.62 (d, J=8.4 Hz, 1H), 7.92 (s, 1H), 9.53 (s, 1H), 11.09 (s, 1H);

MS m/e 392 (MH$^+$).

1-[1-(3-Methyl-butyl)-5-(5-oxo-4,5-dihydro-[1,2,4]oxadiazol-3-yl)-1H-benzoimidazol-2-ylmethyl]-1,3-dihydro-benzoimidazol-2-one

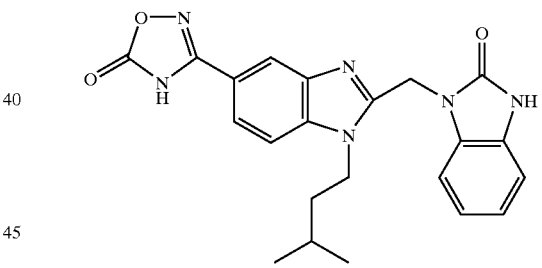

25

N-Hydroxy-1-(3-methyl-butyl)-2-(2-oxo-2,3-dihydro-benzoimidazol-1-ylmethyl)-1H-benzoimidazole-5-carboxamidine (75 mg, 0.191 mmol) was treated with phosgene (1 ml, 1.91 mmol, 1.92 M in toluene) and heated to reflux for 2.5 h. The mixture was cooled and stirred for 48 h. A white precipitate was isolated by filtration to give 21 mg (26%) of 1-[1-(3-Methyl-butyl)-5-(5-oxo-4,5-dihydro-[1,2,4]oxadiazol-3-yl)-1H-benzoimidazol-2-ylmethyl]-1,3-dihydro-benzoimidazol-2-one.

$^1$H NMR (DMSO-d6) δ: 0.91 (d, J=6.6 Hz, 6H), 1.15–1.20 (m, 2H), 1.35–1.43 (m, 1H), 4.32–4.37 (m, 2H), 5.35 (s, 2H), 6.92–7.04 (m, 4H), 7.08 (d, J=8.5 Hz, 1H), 7.71 (s, 3H), 8.05 (s, 1H), 11.11 (s, 1H);

MS m/e 418 (MH$^+$).

(2-Oxo-2,3-dihydro-benzoimidazol-1-yl)-acetic Acid tert-butyl Ester

26

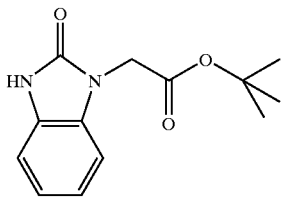

A solution of 2-oxo-2,3-dihydro-benzoimidazole-1-carboxylic acid ethyl ester (3 g, 14.78 mmol) (N. Meanwell et al, *J. Org. Chem*, 1995, 60(6), 1565–82) in THF (100 ml) was treated with BTPP(5.4 ml, 17.74 mmol) followed by t-butylbromoacetate (2.4 ml, 16.3 mmol) and the mixture was stirred for 30 minutes. The solution was diluted with ether and washed with water, dired over MgSO$_4$ and concentrated. The residue was dissolved in MeOH (30 ml) and treated with NaOH (10 N, 3 ml, 30 mmol) and stirred for 1 h at 23° C. The solvent was removed and the residue diluted with ether and washed with 1N HCl, saturated NaCl dried over MgSO$_4$ and concentrated. The residue was purified by flash chromatography to give 1.84 g (50%) (2-oxo-2,3-dihydro-benzoimidazol-1-yl)-acetic acid tert-butyl ester as a white solid.

$^1$H NMR (DMSO-d6) δ: 1.41 (s, 9H), 4.53 (s, 2H), 6.94–7.06 (m, 4H), 10.92 (s, 1H, exchanges with D$_2$O);
MS m/e 248 (MH$^+$).

{3-[5-Cyano-1-(3-methyl-butyl)-1H-benzoimidazol-2-ylmethyl]-2-oxo-2,3-dihydro-benzoimidazol-1-yl}-acetic acid tert-butyl ester

27

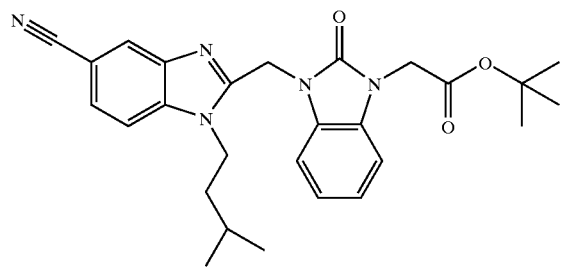

(2-Oxo-2,3-dihydro-benzoimidazol-1-yl)-acetic acid tert-butyl Ester (399 mg, 1.61 mmol) in CH$_2$Cl$_2$ (15 ml) was trreated with BTPP and then treated with 2-chloromethyl-1-(3-methyl-butyl)-1H-benzoimidazole-5-carbonitrile (400 mg, 1.53 mmol). The reaction was stirred for 25 min then the mixture was diluted with ether and washed with water. The organic layer was dried over MgSO$_4$, concentrated and the residue purified by column chromatography with gradient elution using first 1:1 EtOAc in hexanes then 2:1 EtOAc in hexanes to give 1.52 g (99%) of {3-[5-Cyano-1-(3-methyl-butyl)-1H-benzoimidazol-2-ylmethyl]-2-oxo-2,3-dihydro-benzoimidazol-1-yl}-acetic acid tert-butyl ester as a white solid.

$^1$H NMR (CDCl$_3$) d: 0.97 (d, J=6.6 Hz, 6H), 1.45–1.57 (m, 2H), 1.48 (s, 9H), 1.68–1.77 (m, 1H), 4.34 (t, J=8.3 Hz, 2H), 4.56 (s, 2H), 5.43 (s, 2H), 6.86–6.89 (m, 1H), 7.04–7.12 (m, 2H), 7.36–7.39 (m, 2H), 7.54 (dd, J=1.2, 8.4 Hz, 1H), 8.13 (s, 1H);
MS m/e 473 (MH$^+$).

{3-[5-(N-Hydroxycarbamimidoyl)-1-(3-methyl-butyl)-1H-benzoimidazol-2-ylmethyl]-2-oxo-2,3-dihydro-benzoimidazol-1-yl}-acetic Acid tert-butyl Ester

28

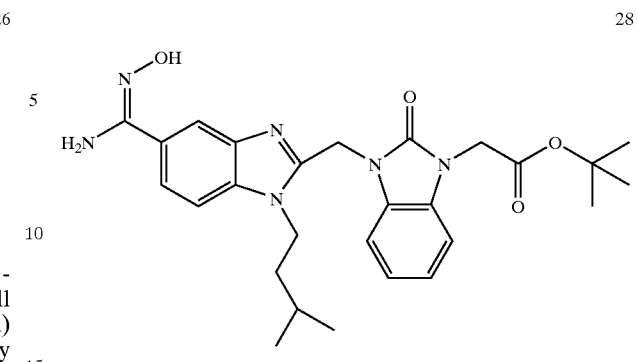

{3-[5-Cyano-1-(3-methyl-butyl)-1H-benzoimidazol-2-ylmethyl]-2-oxo-2,3-dihydro-benzoimidazol-1-yl}-acetic acid tert-butyl ester (1.5 g, 3.17 mmol), hydroxylamine hydrochloride (660 mg, 9.5 mmol) and K$_2$CO$_3$ (657 mg, 4.75 mmol) are dissolved in EtOH (40 ml) and heated to reflux for 12 h. The reaction mixture was cooled and the product was isolated by filtration to give 870 mg (54%) of {3-[5-(N-Hydroxycarbamimidoyl)-1-(3-methyl-butyl)-1H-benzoimidazol-2-ylmethyl]-2-oxo-2,3-dihydro-benzoimidazol-1-yl}-acetic acid tert-butyl ester as a white solid.

$^1$H NMR (CDCl$_3$) δ: 0.95 (d, J=6.6 Hz, 6H), 1.47–1.51 (m, 2H), 1.48 (s, 9H), 1.67–1.72 (m, 1H), 4.28 (t, J=8.3 Hz, 2H), 4.56 (s, 2H), 5.19 (br s, 1H), 5.42 (s, 2H), 6.85–6.88 (m, 1H), 7.03–7.07 (m, 2H), 7.31 (d, J=8.6 Hz, 1H), 7.38 (d, J=6.9 Hz, 1H), 7.64 (d, J=8.6 Hz, 1H), 8.09 (s, 1H);
MS m/e 506 (MH+).
Calcd for C$_{27}$H$_{33}$N$_6$O$_4$: %C, 64.14; %H, 6.58; %N, 16.62; Found: %C, 63.85; %H, 6.63; %N, 16.33.

{3-[5-Carbamimidoyl-1-(3-methyl-butyl)-1H-benzoimidazol-2-ylmethyl]-2-oxo-2,3-dihydro-benzoimidazol-1-yl}-acetic Acid tert-butyl Ester

29

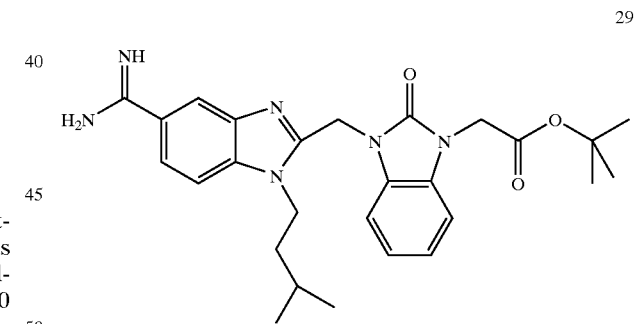

A solution of {3-[5-(N-hydroxycarbamimidoyl)-1-(3-methyl-butyl)-1H-benzoimidazol-2-ylmethyl]-2-oxo-2,3-dihydro-benzoimidazol-1-yl}-acetic acid tert-butyl ester (1.4 g, 2.76 mmol) in AcOH (50 ml) was added to 10% Pd/C (166 mg) and hydrogenated at 50 psi for 4 h then the mixture was filtered and washed with MeOH. The solvent was removed and the residue triturated with EtOAc to give 1 g (74%) of {3-[5-carbamimidoyl-1-(3-methyl-butyl)-1H-benzoimidazol-2-ylmethyl]-2-oxo-2,3-dihydro-benzoimidazol-1-yl}-acetic acid tert-butyl ester as a white solid.

$^1$H NMR (DMSO) δ: 0.94 (d, J=6.6 Hz, 6H), 1.43 (s, 9H), 1.43–1.58 (m, 2H), 1.68–1.78 (m, 1H), 4.28–4.43 (m, 2H), 4.67 (s, 2H), 5.46 (s, 2H), 7.06–7.07 (m, 2H), 7.17–7.25 (m, 3H), 7.68 (d, J=8.4 Hz, 1H), 7.75 (d, J=8.4 Hz, 1H), 8.13 (s, 1H);

MS m/e 434 (MH+).

{3-[5-Carbamimidoyl-1-(3-methyl-butyl)-1H-benzoimidazol-2-ylmethyl]-2-oxo-2,3-dihydro-benzoimidazol-1-yl}-acetic Acid

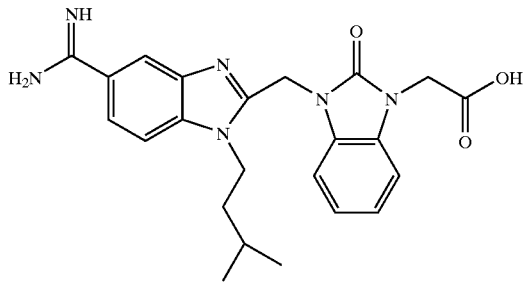

{3-[5-Carbamimidoyl-1-(3-methyl-butyl)-1H-benzoimidazol-2-ylmethyl]-2-oxo-2,3-dihydro-benzoimidazol-1-yl}-acetic acid tert-butyl ester (1.0 g, 2.0 mmol) was dissolved in CH₂Cl₂ (50 ml) treated with TFA (3 ml) and stirred for 48 h. The solvent was removed and the residue triturated with EtOAc to give 850 mg (98%) of {3-[5-Carbamimidoyl-1-(3-methyl-butyl)-1H-benzoimidazol-2-ylmethyl]-2-oxo-2,3-dihydro-benzoimidazol-1-yl}-acetic acid as a with solid.

$^1$H NMR (DMSO-d6) δ: 0.94 (d, J=6.6 Hz, 6H), 1.43–1.53 (m, 2H), 1.53–1.69 (m, 1H), 4.38–4.43 (m, 2H), 4.68 (s, 2H), 5.48 (s, 2H), 7.03–7.08 (d, J=8.7 Hz, 1H), 7.18–7.26 (m, 2H), 7.70 (dd, J=1.5, 8.4 Hz, 1H), 7.80 (d, J=8.7 Hz, 1H), 8.16 (d, J=1.2 Hz, 1H), 8.89 (br s, 2H), 9.21 (br s, 2H);

MS m/e 490 (MH+).

(3-Isopropenyl-2-oxo-2,3-dihydro-benzoimidazol-1-yl)-acetic Acid Methyl Ester

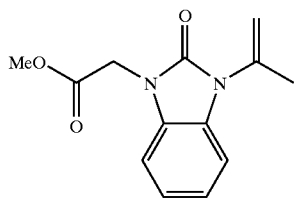

N-isopropenyl-2-benzimidazolone (15.0 g, 86.10 mmol), methyl bromoacetate (13.2 g, 86.1 mmol) and potassium carbonate (14.25 g, 103.26 mmol) were stirred in acetonitrile (300 ml) at room temperature overnight. The next day the reaction mixture was filtered and concentrated to give 21.0 g (99% yield) of (3-isopropenyl-2-oxo-2,3-dihydro-benzoimidazol-1-yl)-acetic acid methyl ester as a clear oil:

$^1$H NMR (DMSO-d6) δ 2.13 (s, 3H), 3.69 (s, 3H), 4.74 (s, 2H), 5.17 (s, 1H), 5.38 (s, 1H), 7.05–7.23 (m, 4H);

IR (KBr, cm$^{-1}$) 2955, 1755, 1714, 1493, 757;

MS m/e 247 (MH+).

(3-Isopropenyl-2-oxo-2,3-dihydro-benzoimidazol-1-yl)-acetic Acid

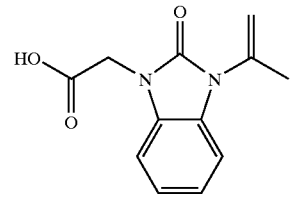

The solution of (3-isopropenyl-2-oxo-2,3-dihydro-benzoimidazol-1-yl)-acetic acid (3.33 g, 17.79 mmol) in methanol (20 mL) was stirred with 1N NaOH (19.19 ml, 19.18 mmol) at room temperature overnight. The solvent was evaporated and the residue dissolved in water and acidified with 1N HCl. The precipitate was filtered off, washed with water and dried under vacuum to give 2.7 g (91% yield) of (3-isopropenyl-2-oxo-2,3-dihydro-benzoimidazol-1-yl)-acetic acid as a white solid:

$^1$H NMR (DMSO-d6) δ 2.15 (s, 3H), 4.62 (s, 2H), 5.18 (s, 1H), 5.4 (s, 1H), 7.07–7.21 (m, 4H);

IR (KBr, cm$^{-1}$) 2967, 1751 1675, 1206, 752;

MS m/e 233 (MH+);

Anal. Calcd for C₁₂H₁₂N₂O₃: C, 62.06; H, 5.21; N, 12.06. Found: C, 61.69; H, 5.33; N, 11.98.

4-(3-Hydroxy-propylamino)-3-nitro-benzonitrile

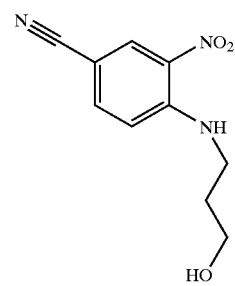

4-(3-Hydroxy-propylamino)-3-nitro-benzonitrile was prepared as described for 4-(3-methyl-butylamino)-3-nitro-benzonitrile using 3-amino-propan-1-ol.

$^1$H NMR (CDCl₃) δ: 1.97 (m, 2H), 3.47–3.56 (m, 2H), 3.87 (t, J=5.4 Hz, 2H), 6.97 (d, J=9.0 Hz, 1H), 7.60 (dd, J=1.5, 8.7 Hz, 1H), 8.50 (d, J=1.5 Hz, 1H);

MS m/e 221 (MH+).

N-[5-Cyano-2-(3-hydroxy-propylamino)-phenyl]-2-(3-isopropenyl-2-oxo-2,3-dihydro-benzoimidazol-1-yl)-acetamide

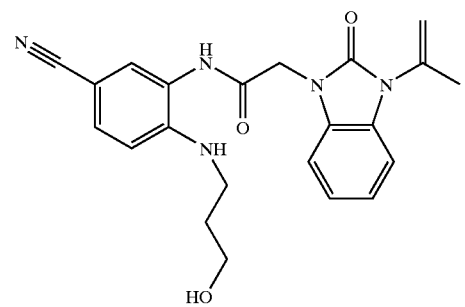

3-Amino-4-(3-hydroxy-propylamino)-benzonitrile was prepared by catalytic reduction of 4-(3-hydroxy-propylamino)-3-nitro-benzonitrile as described for acetic acid 5-cyano-1-(3-methyl-butyl)-1H-benzoimidazol-2-yl methyl ester.

A solution of 3-amino-4-(3-hydroxy-propylamino)-benzonitrile (484 mg, 2.53 mmol) and (3-isopropenyl-2-oxo-2,3-dihydro-benzoimidazol-1-yl)-acetic acid (646 mg, 2.78 mmol) in THF (50 ml) was treated with EEDQ (625 mg, 2.53 mmol) and stirred for 48 h at 23° C. A grey precipitate was filtered off to give 526 mg (47%) of N-[5-Cyano-2-(3-hydroxy-propylamino)-phenyl]-2-(3-isopropenyl-2-oxo-2,3-dihydro-benzoimidazol-1-yl)-acetamide.

$^1$H-NMR (CDCl$_3$) δ: 1.69–1.78 (m, 2H), 2.17 (s, 3H), 3.17–3.26 (m, 2H), 3.50–3.55 (m, 2H), 4.76 (s, 2H), 5.19 (s, 1H), 6.10–6.18 (s, 1H), 6.73 (d, J=8.4 Hz, 1H), 7.07–7.24 (m, 4H), 7.44–7.47 (m, 2H), 9.64 (s, 1H);

MS m/e 405 (MH$^+$).

1-(3-Hydroxy-propyl)-2-(2-oxo-2,3-dihydro-benzoimidazol-1-ylmethyl)-1H-benzoimidazole-5-carbonitrile

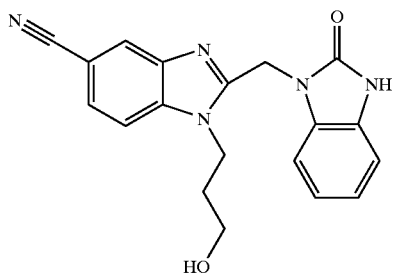

1-(3-Hydroxy-propyl)-2-(2-oxo-2,3-dihydro-benzoimidazol-1-ylmethyl)-1H-benzoimidazole-5-carbonitrile was prepared as described for acetic acid 5-cyano-1-(3-methyl-butyl)-1H-benzoimidazol-2-ylmethyl ester using TFA. The isopropenyl group was also removed during this operation.

$^1$H-NMR (CDCl$_3$) δ: 2.01–2.19 (m, 2H), 4.42 (t, J=6.0 Hz, 2H), 4.54 (t, J=7.7 Hz, 2H), 5.40 (s, 2H), 7.06–7.12 (m, 3H), 7.40 (d, J=8.5 Hz, 1H), 7.40–7.47 (m, 1H), 7.58 (d, J=8.1 Hz, 1H), 8.18 (s, 1H), 8.25 (s, 1H);

MS m/e 387 (MH$^+$).

1H-Benzotriazole-5-carbonitrile

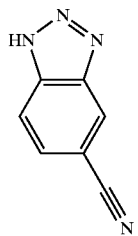

1H-Benzotriazole-5-carboxylic acid (1.0 g, 6.13 mmol), urea (0.552 g, 9.2 mmol) and sulfamic acid (1.19 g, 12.3 mmol) were heated to 240° C. for 1 h. The solid was triturated with water and the solid refluxed with CH$_2$Cl$_2$ for 1 h and the remaining solid removed by filtration. The solvent was removed to give 1H-benzotriazole-5-carbonitrile 100 mg (14%) as a white solid.

$^1$H-NMR (CD$_3$OD) δ: 7.77 (dd, J=1.2, 8.5 Hz, 1H), 8.02 (dd, J=1.2 Hz, 8.5 Hz, 1H), 8.48 (s, 1H);

MS m/e 144 (MH$^+$).

1-[5-Cyano-1-(3-methyl-butyl)-1H-benzoimidazol-2-ylmethyl]-1H-benzotriazole-5-carbonitrile, 3-[5-Cyano-1-(3-methyl-butyl)-1H-benzoimidazol-2-ylmethyl]-3H-benzotriazole-5-carbonitrile and 2-[5-Cyano-1-(3-methyl-butyl)-1H-benzoimidazol-2-ylmethyl]-2H-benzotriazole-5-carbonitrile

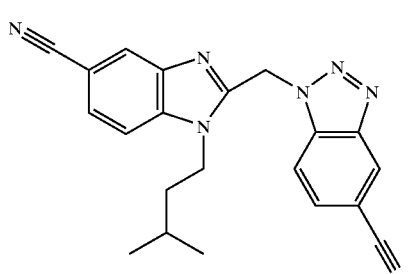

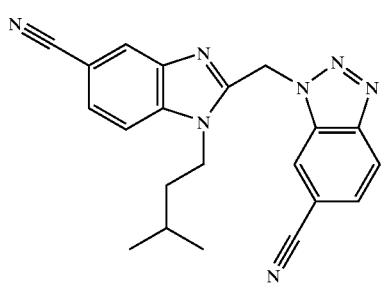

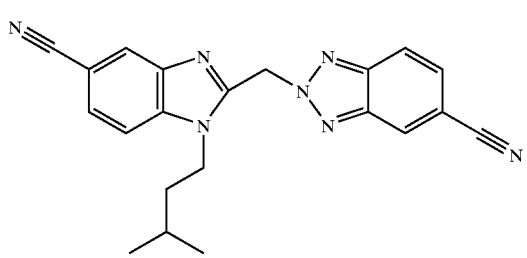

1-[5-Cyano-1-(3-methyl-butyl)-1H-benzoimidazol-2-ylmethyl]-1H-benzotriazole-5-carbonitrile and 3-[5-Cyano-1-(3-methyl-butyl)-1H-benzoimidazol-2-ylmethyl]-3H-benzotriazole-5-carbonitrile were prepared as described for 2-(3-isopropyl-2-oxo-2,3-dihydro-benzoimidazol-1-ylmethyl)-1-(3-methyl-butyl)-1H-benzoimidazole-5-carbonitrile using 2-chloromethyl-1-(3-methyl-butyl)-1H-benzoimidazole-5-carbonitrile and 1H-benzotriazole-5-carbonitrilewith NaH as base. The compounds were separated by column chromatography to give the three products in the order listed above in 13%, 15% and 12% yield respectively.

1-[5-Cyano-1-(3-methyl-butyl)-1H-benzoimidazol-2-ylmethyl]-1H-benzotriazole-5-carbonitrile (High R$_f$):

$^1$H-NMR (DMSO-d6) δ: 0.99 (d, J=6.6 Hz, 6H), 1.36–1.41 (m, 2H), 1.64–1.78 (m, 1H), 4.29–4.35 (m, 2H), 6.22 (s, 2H), 7.40 (d, J=8.4 Hz, 1H), 7.56 (dd, J=1.5, 9 Hz, 1H), 7.70 (d, J=8.4 Hz, 1H), 7.98 (d, J=9.0 Hz, 1H), 8.12 (s, 1H), 8.43 (s, 1H);

MS m/e 369 (MH$^+$).

3-[5-Cyano-1-(3-methyl-butyl)-1H-benzoimidazol-2-ylmethyl]-3H-benzotriazole-5-carbonitrile (High R$_f$):

$^1$H-NMR (DMSO-d6) δ: 0.94 (d, J=6.6 Hz, 6H), 1.54–1.59 (m, 2H), 1.60–1.74 (m, 1H), 4.42–4.47 (m, 2H), 6.56 (s, 2H), 7.68 (dd, J=1.2, 8.4 Hz, 1H), 7.81–7.5 (m, 2H), 8.12 (s, 1H), 8.35 (d, J=8.7 Hz, 1H), 8.67 (s, 1H);

MS m/e 369 (MH$^+$).

2-[5-Cyano-1-(3-methyl-butyl)-1H-benzoimidazol-2-ylmethyl]-2H-benzotriazole-5-carbonitrile (Low R$_f$)

¹H-NMR (DMSO-d6) δ: 0.81 (d, J=6.6 Hz, 6H), 1.25–1.31 (m, 2H), 1.53–1.56 (m, 1H), 4.34–4.39 (m, 2H), 6.59 (s, 2H), 7.69–7.83 (m, 4H), 8.18 (d, J=9 Hz, 1H);
MS m/e 369 (MH⁺).

N-Hydroxy-1-[5-(N-hydroxycarbamimidoyl)-1-(3-methyl-butyl)-1H-benzoimidazol-2-ylmethyl]-1H-benzotriazole-5-carboxamidine

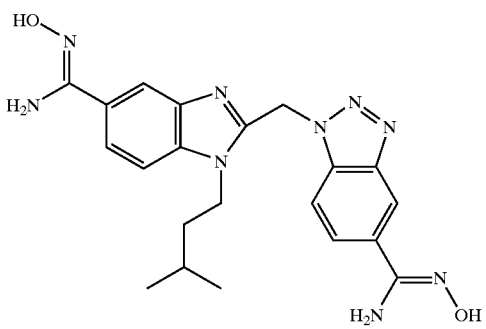

N-Hydroxy-1-[5-(N-hydroxycarbamimidoyl)-1-(3-methyl-butyl)-1H-benzoimidazol-2-ylmethyl]-1H-benzotriazole-5-carboxamidine was prepared as described for {3-[5-(N-hydroxycarbamimidoyl)-1-(3-methyl-butyl)-1H-benzoimidazol-2-ylmethyl]-2-oxo-2,3-dihydro-benzoimidazol-1-yl}-acetic acid tert-butyl ester using 1-[5-cyano-1-(3-methyl-butyl)-1H-benzoimidazol-2-ylmethyl]-1H-benzotriazole-5-carbonitrile.

¹H-NMR (DMSO-d6) δ: 0.84 (d, J=6.6 Hz, 6H), 1.21–1.36 (m, 2H), 1.47–1.61 (m, 1H), 4.22–4.34 (m, 2H), 5.73–5.87 (s, 2H), 5.90–6.00 (s, 2H), 6.37 (s, 2H), 7.48 (d, J=8.7 Hz, 1H), 7.61 (d, J=8.4 Hz, 1H), 7.65–7.67 (m, 1H), 7.75 (d, J=8.7 Hz, 1H), 7.86–7.92 (m, 1H), 8.32 (s, 1H), 9.53 (s, 1H), 9.75 (s, 1H);
MS m/e 435 (MH⁺).

N-Hydroxy-3-[5-(N-hydroxycarbamimidoyl)-1-(3-methyl-butyl)-1H-benzoimidazol-2-ylmethyl]-3H-benzotriazole-5-carboxamidine

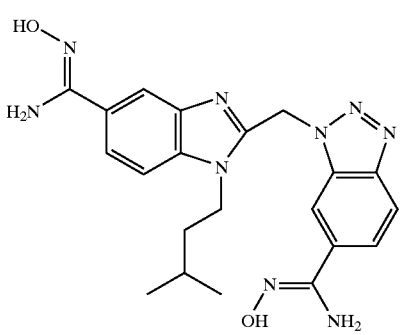

N-Hydroxy-3-[5-(N-hydroxycarbamimidoyl)-1-(3-methyl-butyl)-1H-benzoimidazol-2-ylmethyl]-3H-benzotriazole-5-carboxamidine was prepared as described for {3-[5-(N-hydroxycarbamimidoyl)-1-(3-methyl-butyl)-1H-benzoimidazol-2-ylmethyl]-2-oxo-2,3-dihydro-benzoimidazol-1-yl}-acetic acid tert-butyl ester using 3-[5-cyano-1-(3-methyl-butyl)-1H-benzoimidazol-2-ylmethyl]-3H-benzotriazole-5-carbonitrile.

¹H-NMR (DMSO-d6) δ: 0.88 (d, J=6.6 Hz, 6H), 1.43–1.62 (m, 1H), 4.31–4.37 (m, 2H), 5.79 (s, 2H), 5.95 (s, 2H), 6.37 (s, 2H), 7.52 (d, J=8.7 Hz, 1H), 7.64 (d, J=8.7 Hz, 1H), 7.76 (d, J=8.7 Hz, 1H), 7.88 (d, J=8.7 Hz, 1H), 8.06 (d, J=8.7 Hz, 1H), 8.19 (s, 1H), 9.53 (s, 1H), 9.87 (s, 2H);

MS m/e 435 (MH⁺).

N-Hydroxy-2-[5-(N-hydroxycarbamimidoyl)-1-(3-methyl-butyl)-1H-benzoimidazol-2-ylmethyl]-2H-benzotriazole-5-carboxamidine

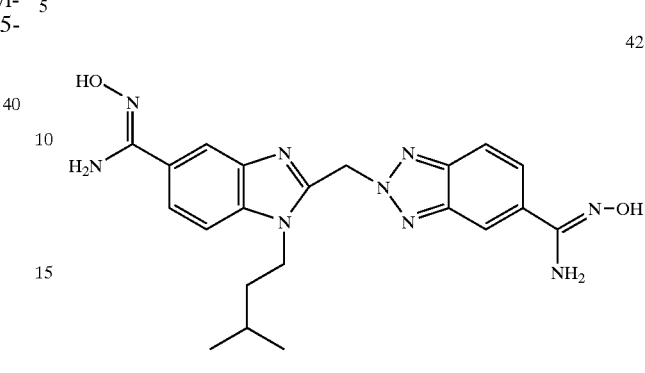

N-Hydroxy-2-[5-(N-hydroxycarbamimidoyl)-1-(3-methyl-butyl)-1H-benzoimidazol-2-ylmethyl]-2H-benzotriazole-5-carboxamidine was prepared as described for {3-[5-(N-hydroxycarbamimidoyl)-1-(3-methyl-butyl)-1H-benzoimidazol-2-ylmethyl]-2-oxo-2,3-dihydro-benzoimidazol-1-yl}-acetic acid using 2-[5-Cyano-1-(3-methyl-butyl)-1H-benzoimidazol-2-ylmethyl]-2H-benzotriazole-5-carbonitrile.

¹H-NMR (DMSO-d6) δ: 0.79 (d. J=6.6 Hz, 6H), 1.15–1.24 (m, 2H), 1.46–1.60 (m, 1H), 4.21–4.31 (m, 2H), 5.83 (s, 1H), 5.99 (s, 1H), 6.40 (s, 2H), 7.53 (d, J=8.4 Hz, 1H), 7.67 (d, J=7.8 Hz, 1H), 7.87 (s, 1H), 7.94 (s, 1H), 8.21 (s, 1H), 9.56 (s, 1H), 9.89 (s, 1H).

1-[5-Carbamimidoyl-1-(3-methyl-butyl)-1H-benzoimidazol-2-ylmethyl]-1H-benzotriazole-5-carboxamidine

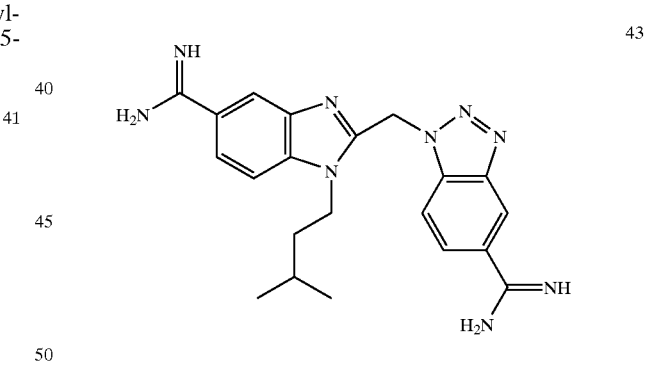

1-[5-Carbamimidoyl-1-(3-methyl-butyl)-1H-benzoimidazol-2-ylmethyl]-1H-benzotriazole-5-carboxamidine was prepared as described for {3-[5-carbamimidoyl-1-(3-methyl-butyl)-1H-benzoimidazol-2-ylmethyl]-2-oxo-2,3-dihydro-benzoimidazol-1-yl}-acetic acid tert-butyl ester using N-hydroxy-1-[5-(N-hydroxycarbamimidoyl)-1-(3-methyl-butyl)-1H-benzoimidazol-2-ylmethyl]-1H-benzotriazole-5-carboxamidine.

¹H NMR (DMSO-d6) δ: 0.93 (d, J=6.6 Hz, 6H), 1.44–1.49 (m, 2H), 1.64–1.68 (m, 1H), 1.75 (s, 3H, AcOH), 4.41–4.47 (m, 2H), 6.56 (s, 2H), 7.70 (d, J=8.4 Hz, 1H), 7.79 (d, J=8.7 Hz, 1H), 7.95–8.07 (m, 3H), 8.62 (s, 1H).

3-[5-Carbamimidoyl-1-(3-methyl-butyl)-1H-benzoimidazol-2-ylmethyl]-3H-benzotriazole-5-carboxamidine

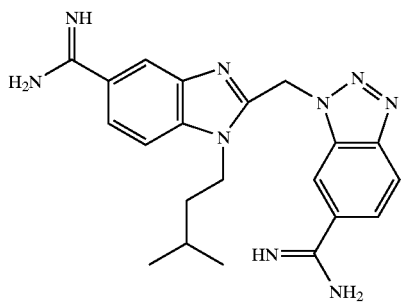

3-[5-Carbamimidoyl-1-(3-methyl-butyl)-1H-benzoimidazol-2-ylmethyl]-3H-benzotriazole-5-carboxamidine was prepared as described for {3-[5-carbamimidoyl-1-(3-methyl-butyl)-1H-benzoimidazol-2-ylmethyl]-2-oxo-2,3-dihydro-benzoimidazol-1-yl}-acetic acid tert-butyl ester using N-Hydroxy-3-[5-(N-hydroxycarbamimidoyl)-1-(3-methyl-butyl)-1H-benzoimidazol-2-ylmethyl]-3H-benzotriazole-5-carboxamidine.

$^1$H-NMR (CD$_3$OD) δ: 1.02 (d, J=6.6 Hz, 1H), 1.50–1.58 (m, 2H), 1.71–1.80 (m, 1H), 4.54–4.60 (m, 2H), 6.51 (s, 2H), 7.79–7.84 (m, 3H), 8.13 (s, 1H), 8.29 (d, J=8.7 Hz, 1H), 8.51 (s, 1H);

MS m/e 403 (MH$^+$).

2-[5-Carbamimidoyl-1-(3-methyl-butyl)-1H-benzoimidazol-2-ylmethyl]-2H-benzotriazole-5-carboxamidine

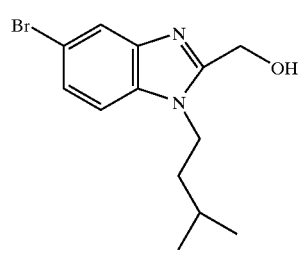

2-[5-Carbamimidoyl-1-(3-methyl-butyl)-1H-benzoimidazol-2-ylmethyl]-2H-benzotriazole-5-carboxamidine was prepared as described for {3-[5-carbamimidoyl-1-(3-methyl-butyl)-1H-benzoimidazol-2-ylmethyl]-2-oxo-2,3-dihydro-benzoimidazol-1-yl}-acetic acid tert-butyl ester using N-Hydroxy-2-[5-(N-hydroxycarbamimidoyl)-1-(3-methyl-butyl)-1H-benzoimidazol-2-ylmethyl]-2H-benzotriazole-5-carboxamidine.

$^1$H-NMR (DMSO-d6) δ: 0.93 (d, J=6.6 Hz, 6H), 1.43–1.50 (m, 2H), 1.67–1.71 (m, 1H), 4.48–4.53 (m, 2H), 6.52 (s, 2H), 7.77–7.81 (m, 2H), 8.15 (d, J=8.9 Hz, 1H), 8.19 (s, 1H), 8.51 (s, 1H).

(4-Bromo-2-nitro-phenyl)-(3-methyl-butyl)-amine

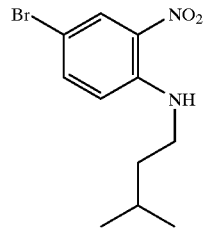

(4-Bromo-2-nitro-phenyl)-(3-methyl-butyl)-amine was prepared by the same procedure as 4-(3-methyl-butylamino)-3-nitro-benzonitrile, except using 3-bromo-6-fluoro-nitrobenzene.

$^1$H NMR (CDCl$_3$) δ: 0.98 (d, J=6.6 Hz, 6 H), 1.60–1.65 (m, 2 H), 1.75–1.78 (m, 1 H), 3.27–3.31 (m, 2 H), 6.76 (d, J=9.2 Hz, 1 H), 7.48–7.50 (m, 1 H), 8.02 (b, 1 H), 8.31 (d, J=2.4 Hz, 1 H).

[5-Bromo-1-(3-methyl-butyl)-1H-benzoimidazol-2-yl]-methanol

A mixture of (4-bromo-2-nitro-phenyl)-(3-methyl-butyl)-amine (2.87 g, 10.0 mmol), iron powder (1.67 g, 30.0 mmol) and ammonium chloride (2.68 g, 50.0 mmol) in 1:1 MeOH–H$_2$O (150 mL) was heated to reflux for 12 h then filtered through celite when hot. The filtrate was diluted with EtOAc (100 mL), and washed with brine. The organic layer was dried over MgSO$_4$ and evaporated. The residue was used for the next reaction without further purification.

A mixture of the compound mentioned above and glycolic acid (0.82 g, 10.7 mmol) in 6N HCl (30 mL) was heated to reflux for 12 h. After cooling, the final solution was neutralized with conc. ammonia to pH 7 and was extracted with EtOAc. The organic layer was washed with brine and was dried over MgSO$_4$ and evaporated. The residue was purified by prep-HPLC (gradient 10%–100% B) to yield 1.37 g (46% two steps) of [5-bromo-1-(3-methyl-butyl)-1H-benzoimidazol-2-yl]-methanol as a white solid.

$^1$H NMR (CDCl$_3$) δ: 1.01 (d, J=6.2 Hz, 6 H), 1.67–1.70 (m, 3 H), 4.17 (t, J=7.7 Hz, 2 H), 4.87 (s, 2 H), 7.16 (d, J=8.6 Hz, 1 H), 7.34–7.36 (m, 1 H), 7.82 (d, J=1.7 Hz, 1 H);

MS m/e 297, 299 (MH$^+$).

5-Bromo-2-chloromethyl-1-(3-methyl-butyl)-1H-benzoimidazole

48

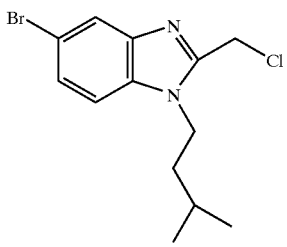

To a solution of [5-bromo-1-(3-methyl-butyl)-1H-benzoimidazol-2-yl]-methanol (1.32 g, 4.44 mmol) in DCM (20 mL) was added thionyl chloride (1.06 g, 8.88 mL) at 0° C. The final solution was stirred at 0° C. for 1 h. The solvent was evaporated and the residue triturated with EtOAc and filtered to give 1.42 g (91%) of 5-bromo-2 chloromethyl-1-(3-methyl-butyl)-1H-benzoimidazole as a white solid.

$^1$H NMR (CD$_3$OD) δ: 1.06 (d, J=6.2 Hz, 6 H), 1.82–1.85 (m, 3 H), 4.54 (t, J=8.1 Hz, 2 H), 5.26 (s, 2 H), 7.67–7.80 (m, 1 H), 7.81–7.92 (m, 2 H), 8.04 (s, 1 H);

MS m/e 315, 317 (MH$^+$).

1-[5-Bromo-1-(3-methyl-butyl)-1H-benzoimidazol-2-ylmethyl]-3-isopropyl-1,3-dihydro-benzoimidazol-2-one

49

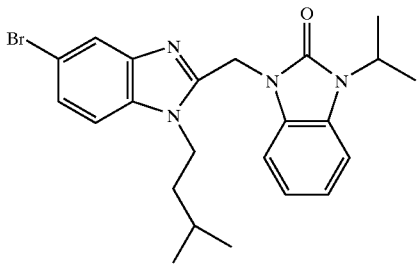

1-[5-Bromo-1-(3-methyl-butyl)-1H-benzoimidazol-2-ylmethyl]-3-isopropyl-1,3-dihydro-benzoimidazol-2-one was prepared by the same procedure as 2-(3-isopropyl-2-oxo-2,3-dihydro-benzoimidazol-1-ylmethyl)-1-(3-methyl-butyl)-1H-benzoimidazole-5-carbonitrile.

$^1$H NMR (CDCl$_3$) δ: 0.94 (d, J=6.6 Hz, 6H), 1.38–1.43 (m, 2H), 1.57 (d, J=7.0 Hz, 6H), 1.66–1.70 (m, 1H), 4.29 (t, J=8.0 Hz, 2H), 4.75–4.79 (m, 1H), 5.36 (s, 2H), 7.02–7.05 (m, 2H), 7.11–7.13 (m, 1H), 7.27–7.28 (m, 2 H), 7.37–7.41 (m, 1H), 7.93 (s, 1H);

MS m/e 457, 459 (MH$^+$).

1-[5-(Benzhydrylidene-amino)-1-(3-methyl-butyl)-1H-benzoimidazol-2-ylmethyl]-3-isopropyl-1,3-dihydro-benzoimidazol-2-one

50

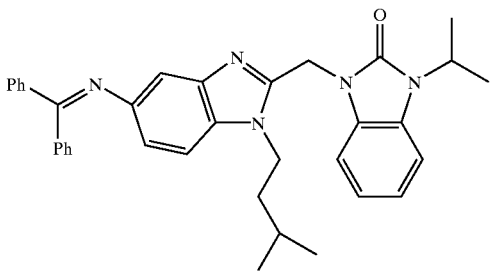

A mixture of 1-[5-bromo-1-(3-methyl-butyl)-1H-benzoimidazol-2-ylmethyl]-3-isopropyl-1,3-dihydro-benzoimidazol-2-one (45 mg, 0.1 mmol), benzophenone imine (22 mg, 0.12 mmol), sodium tert-butoxide (13 mg, 0.14 mmol), BINAP (19 mg, 0.03 mmol) and Pd$_2$(dba)$_3$ (9 mg, 0.01 mmol) in toluene (2 mL) was heated to reflux for 6 h. After cooling, the reaction mixture was diluted with EtOAc and washed with sat. NaHCO$_3$ and brine. The organic layer was dried over MgSO$_4$ and evaporated. The residue was purified by flash chromatography (hexanes:EtOAc 4:1 to 1:1) to give 48 mg (87%) of 1-[5-(benzhydrylidene-amino)-1-(3-methyl-butyl)-1H-benzoimidazol-2-ylmethyl]-3-isopropyl-1,3-dihydro-benzoimidazol-2-one as a yellow solid.

$^1$H NMR (CD$_3$OD) δ: 0.89 (d, J=6.6 Hz, 6 H), 1.34–1.39 (m, 2 H), 1.55 (d, J=6.9 Hz, 6 H), 1.60–1.63 (m, 1 H), 4.22 (t, J=8.0 Hz, 2 H), 4.70–4.73 (m, 1 H), 5.30 (s, 2 H), 6.78–6.82 (m, 1 H), 6.97–6.98 (m, 2H), 7.08–7.11 (m, 4 H), 7.19–7.24 (m, 5 H), 7.27–7.29 (m, 2 H), 7.39–7.41 (m, 1 H), 7.65–7.67 (m, 2 H);

MS m/e 556 (MH$^+$).

1-[5-Amino-1-(3-methyl-butyl)-1H-benzoimidazol-2-ylmethyl]-3-isopropyl-1,3-dihydro-benzoimidazol-2-one

51

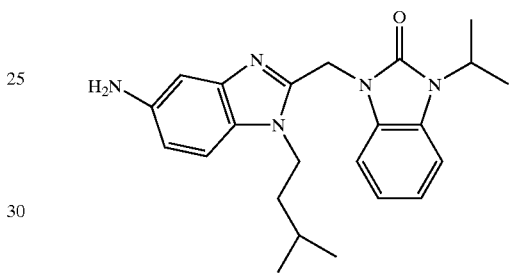

A solution of 1-[5-(benzhydrylidene-amino)-1-(3-methyl-butyl)-1H-benzoimidazol-2-ylmethyl]-3-isopropyl-1,3-dihydro-benzoimidazol-2-one (32 mg, 0.06 mmol) in 0.5 M HCl-THF was stirred at ambient temperature for 1 h. The solvent was evaporated and the residue purified by prep-HPLC (gradient 10%–100% B) to give 20 mg (85%) of 1-[5-amino-1-(3-methyl-butyl)-1H-benzoimidazol-2-ylmethyl]-3-isopropyl-1,3-dihydro-benzoimidazol-2-one as a white solid.

$^1$H NMR (CD$_3$OD) δ: 0.94 (d, J=6.6 Hz, 6 H), 1.55–1.58 (m, 8 H), 1.65–1.69 (m, 1 H), 4.42 (t, J=8.2 Hz, 2 H), 4.71–4.74 (m, 1 H), 5.51 (s, 2 H), 7.09–7.11 (m, 1 H), 7.14–7.21 (m, 3 H), 7.32–7.37 (m, 2 H), 7.62 (d, J=8.8 Hz, 1 H);

MS m/e 392 (MH$^+$).

1-Isopropyl-3-[1-(3-methyl-butyl)-5-vinyl-1H-benzoimidazol-2-ylmethyl]-1,3-dihydro-benzoimidazol-2-one

52

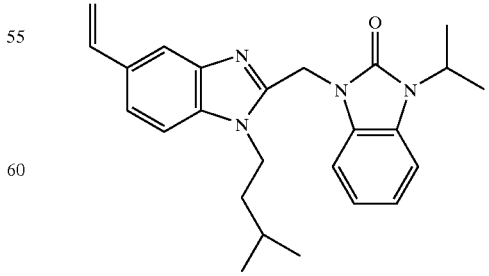

A mixture of 1-[5-bromo-1-(3-methyl-butyl)-1H-benzoimidazol-2-ylmethyl]-3-isopropyl-1,3-dihydrobenzoimidazol-2-one (90 mg, 0.2 mmol), tributylvinyltin (76 mg, 0.24 mmol) and tetrakis(triphenylphosphine) palladium(0) (23 mg, 0.02 mmol) in toluene (4 mL) was heated to reflux for 4 h. After cooling, the reaction mixture was diluted with EtOAc and washed with sat. NaHCO$_3$ and brine. The organic layer was dried over MgSO$_4$ and evaporated. The residue was purified by flash chromatography (hexanes:EtOAc 4:1 to 2:1) to give 26 mg (32%) of 1-isopropyl-3-[1-(3-methyl-butyl)-5-vinyl-1H-benzoimidazol-2-ylmethyl]-1,3-dihydro-benzoimidazol-2-one as a off-white solid.

$^1$H NMR (CDCl$_3$) δ: 0.94 (d, J=6.6 Hz, 6 H), 1.39–1.43 (m, 2 H), 1.55 (d, J=7.0 Hz, 6 H), 1.65–1.75 (m, 1 H), 4.29 (t, J=8.1 Hz, 2 H), 4.75–4.78 (m, 1 H), 5.21 (d, J=10.9 Hz, 1 H), 5.37 (s, 2 H), 5.74 (d, J=17.6 Hz, 1 H), 6.79–6.84 (m, 1 H), 7.00–7.04 (m, 2 H), 7.11 (d, J=7.4 Hz, 1 H), 7.23–7.26 (m, 1 H), 7.37–7.44 (m, 2 H), 7.80 (s, 1 H);

MS m/e 403 (MH$^+$).

1-[5-Ethyl-1-(3-methyl-butyl)-1H-benzoimidazol-2-ylmethyl]-3-isopropyl-1,3-dihydro-benzoimidazol-2-one

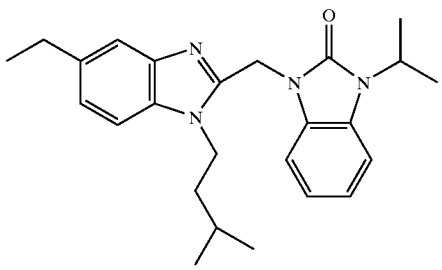

53

1-[5-Ethyl-1-(3-methyl-butyl)-1H-benzoimidazol-2-ylmethyl]-3-isopropyl-1,3-dihydro-benzoimidazol-2-one was prepared by the same procedure as 1-isopropyl-1,3-dihydro-benzoimidazol-2-one.

$^1$H NMR (CDCl$_3$) δ: 0.93 (d, J=6.6 Hz, 6 H), 1.29 (t, J=7.6 Hz, 3 H), 1.37–1.42 (m, 2 H), 1.55 (d, J=7.0 Hz, 6 H), 1.62–1.69 (m, 1 H), 2.75–2.80 (m, 2 H), 4.27 (t, J=8.1 Hz, 2 H), 4.75–4.78 (m, 1 H), 5.36 (s, 2 H), 7.00–7.05 (m, 2 H), 7.10–7.13 (m, 2 H), 7.20 (d, J=8.3 Hz, 1 H), 7.43–7.44 (m, 1 H), 7.60 (s, 1 H);

MS m/e 405 (MH$^+$).

(5-Bromo-1H-benzoimidazol-2-yl)-methanol

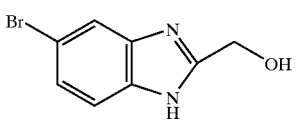

54

(5-Bromo-1H-benzoimidazol-2-yl)-methanol was prepared by the same procedure as [5-bromo-1-(3-methyl-butyl)-1H-benzoimidazol-2-yl]-methanol, starting with 3-bromophenylenediamine.

$^1$H NMR (DMSO-d$_6$) δ: 4.68 (d, J=8.9 Hz, 2 H), 5.74 (t, J=9.4 Hz, 1 H), 7.25–7.29 (m, 1 H), 7.43–7.46 (m, 1 H), 7.66 (s, 1 H), 12.49 (b, 1 H);

MS m/e 226, 228 (MH$^+$).

[6-Bromo-1-(3-methyl-butyl)-1H-benzoimidazol-2-yl]-methanol

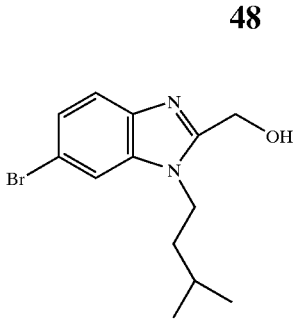

55

[6-Bromo-1-(3-methyl-butyl)-1H-benzoimidazol-2-yl]-methanol was prepared by the same procedure as 2-(3-isopropyl-2-oxo-2,3-dihydro-benzoimidazol-1-ylmethyl)-1-(3-methyl-butyl)-1H-benzoimidazole-5-carbonitrile.

$^1$H NMR (CDCl$_3$) δ1.01 (d, J=6.2 Hz, 6 H), 1.67–1.72 (m, 3 H), 4.15 (t, J=7.8 Hz, 2 H), 4.86 (s, 2 H), 7.33–7.36 (m, 1 H), 7.45 (d, J=1.7 Hz, 1 H), 7.55 (d, J=8.6 Hz, 1 H);

MS m/e 297, 299 (MH$^+$).

2-Hydroxymethyl-3-(3-methyl-butyl)-3H-benzoimidazole-5-carbonitrile

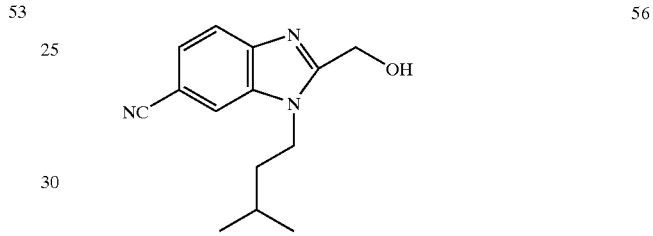

56

A mixture of [6-bromo-1-(3-methyl-butyl)-1H-benzoimidazol-2-yl]-methanol (30 mg, 0.1 mmol), Zn(CN)$_2$ (7 mg, 0.06 mmol) and tetrakis(triphenylphosphine) palladium(0) (12 mg, 0.01 mmol) in DMF (1 mL) was heated to 80° C. for 4 h. After cooling, the reaction mixture was diluted with MeOH and filtered. The filtrate was purified by prep-HPLC (gradient 10%–100% B) to give 16 mg (66%) of 2-hydroxymethyl-3-(3-methyl-butyl)-3H-benzoimidazole-5-carbonitrile as a white solid.

$^1$H NMR (CD$_3$OD) δ: 1.04 (d, J=6.0 Hz, 6 H), 1.77–1.80 (m, 3 H), 4.44 (t, J=7.8 Hz, 2 H), 5.10 (s, 2 H), 7.81–7.83 (m, 1 H), 7.89 (d, J=8.5 Hz, 1 H), 8.32 (s, 1 H);

MS m/e 244 (MH$^+$).

2-Chloromethyl-3-(3-methyl-butyl)-3H-benzoimidazole-5-carbonitrile

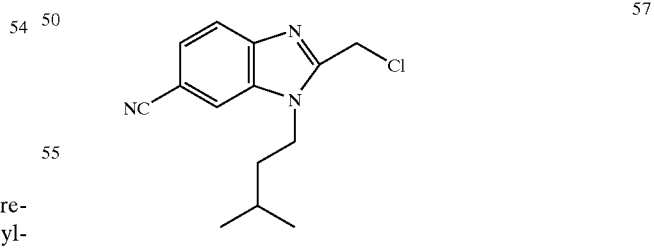

57

2-Chloromethyl-3-(3-methyl-butyl)-3H-benzoimidazole-5-carbonitrile was prepared by the same procedure as 5-bromo-2-chloromethyl-1-(3-methyl-butyl)-1H-benzoimidazole and was used as crude without purification.

MS m/e 262 (MH$^+$).

2-(3-Isopropyl-2-oxo-2,3-dihydro-benzoimidazol-1-ylmethyl)-3-(3-methyl-butyl)-3H-benzoimidazole-5-carbonitrile

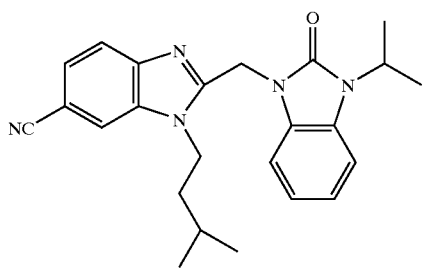

58

2-(3-Isopropyl-2-oxo-2,3-dihydro-benzoimidazol-1-ylmethyl)-3-(3-methyl-butyl)-3H-benzoimidazole-5-carbonitrile was prepared by the same procedure as 2-(3-isopropyl-2-oxo-2,3-dihydro-benzoimidazol-1-ylmethyl)-1-(3-methyl-butyl)-1H-benzoimidazole-5-carbonitrile.

$^1$H NMR (CDCl$_3$) δ: 0.97 (d, J=6.6 Hz, 6 H), 1.43–1.46 (m, 2 H), 1.57 (d, J=7.0 Hz, 6 H), 1.68–1.72 (m, 1 H), 4.36 (t, J=8.2 Hz, 2 H), 4.73–4.78 (m, 1 H), 5.39 (s, 2 H), 7.03–7.07 (m, 2 H), 7.13 (d, J=7.4 Hz, 1 H), 7.38–7.40 (m, 1 H), 7.51–7.53 (m, 1 H), 7.64 (s, 1 H), 7.84 (d, J=8.4 Hz, 1 H);

MS m/e 402 (MH$^+$).

1-[6-Aminomethyl-1-(3-methyl-butyl)-1H-benzoimidazol-2-ylmethyl]-3-isopropyl-1,3-dihydro-benzoimidazol-2-one

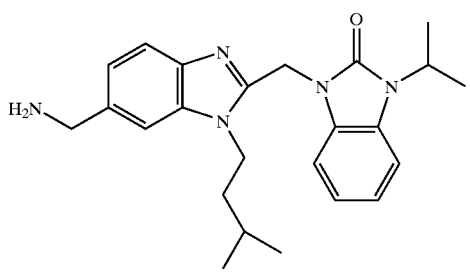

59

1-[6-Aminomethyl-1-(3-methyl-butyl)-1H-benzoimidazol-2-ylmethyl]-3-isopropyl-1,3-dihydro-benzoimidazol-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 0.97 (d, J=6.6 Hz, 6 H), 1.53–1.58 (m, 8 H), 1.69–1.73 (m, 1 H), 4.29 (s, 2 H), 4.42 (t, J=8.3 Hz, 2 H), 4.72–4.75 (m, 1 H), 5.52 (s, 2 H). 7.07–7.08 (m, 1 H), 7.13–7.16 (m, 1 H), 7.19 (d, J=7.8 Hz, 1 H), 7.36 (d, J=7.8 Hz, 1 H), 7.47–7.49 (m, 1 H), 7.73–7.76 (m, 2 H);

MS m/e 406 (MH$^+$).

N-[2-(3-Isopropyl-2-oxo-2,3-dihydro-benzoimidazol-1-ylmethyl)-3-(3-methyl-butyl)-3H-benzoimidazol-5-ylmethyl]-acetamide

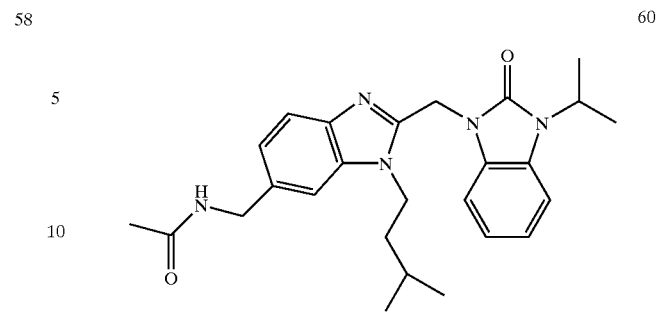

60

N-[2-(3-Isopropyl-2-oxo-2,3-dihydro-benzoimidazol-1-ylmethyl)-3-(3-methyl-butyl)-3H-benzoimidazol-5-ylmethyl]-acetamide was prepared by the same procedure as N-[2-(3-isopropyl-2-oxo-2,3-dihydro-benzoimidazol-1-ylmethyl)-1-(3-methtyl-butyl)-1H-benzoimidazol-5-ylmethyl]-acetamide.

$^1$H NMR (CD$_3$OD) δ: 0.97 (d, J=6.6 Hz, 6 H), 1.57 (d, J=6.9 Hz, 6 H), 1.59–1.65 (m, 2 H), 1.68–1.72 (m, 1 H), 2.00 (s, 3 H), 4.50 (t, J=8.3 Hz, 2 H), 4.54 (s, 2 H), 4.71–4.73 (m, 1 H), 5.65 (s, 2 H), 7.14–7.16 (m, 1 H), 7.18–7.20 (m, 1 H), 7.24 (d, J=7.8 Hz, 1 H), 7.40 (d, J=7.8 Hz, 1 H), 7.51–7.53 (m, 1 H), 7.68–7.71 (m, 2 H);

MS m/e 448 (MH$^+$).

2-(3-Isopropyl-2-oxo-2,3-dihydro-benzoimidazol-1-ylmethyl)-3-(3-methyl-butyl)-3H-benzoimidazole-5-carboxylic Acid

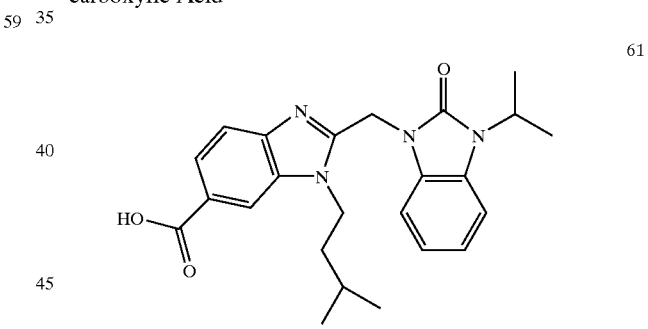

61

2-(3-Isopropyl-2-oxo-2,3-dihydro-benzoimidazol-1-ylmethyl)-3-(3-methyl-butyl)-3H-benzoimidazole-5-carboxylic acid was prepared by the same procedure as 2-(3-isopropyl-2-oxo-2,3-dihydro-benzoimidazol-1-ylmethyl)-1-(3-methyl-butyl)-1H-benzoimidazole-5 carboxylic acid.

$^1$H NMR (d$_6$-DMSO) δ: 0.92 (d, J=6.6 Hz, 6 H), 1.41–1.46 (m, 2 H), 1.48 (d, J=6.9 Hz, 6 H), 1.68–1.68 (m, 1 H), 4.38 (t, J=7.9 Hz, 2 H), 4.65–4.68 (m, 1 H), 5.38 (s, 2 H), 6.99–7.06 (m, 2 H), 7.24 (d, J=7.6 Hz, 1 H), 7.35 (d, J=7.6 Hz, 1 H), 7.64 (d, J=8.4 Hz, 1 H), 7.80 (d, J=8.4 Hz, 1 H), 8.08 (s, 1 H);

MS m/e 421 (MH$^+$).

2-(3-Isopropyl-2-oxo-2,3-dihydro-benzoimidazol-1-ylmethyl)-3-(3-methyl-butyl)-3H-benzoimidazole-5-carboxylic Acid Amide

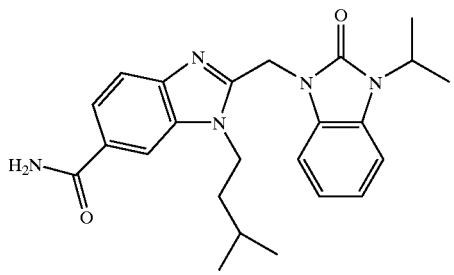

62

2-(3-Isopropyl-2-oxo-2,3-dihydro-benzoimidazol-1-ylmethyl)-3-(3-methyl-butyl)-3H-benzoimidazole-5-carboxylic acid amide was prepared by the same procedure as 2-(3-isopropyl-2-oxo-2,3-dihydro-benzoimidazol-1-ylmethyl)-1-(3-methyl-butyl)-1H-benzoimidazole-5-carboxylic acid dimethylamide, except using ammonium hydroxide.

$^1$H NMR (CD$_3$OD) δ: 0.98 (d, J=6.6 Hz, 6 H), 1.57–1.64 (m, 8 H), 1.71–1.76 (m, 1 H), 4.51 (t, J=8.3 Hz, 2 H), 4.72–4.76 (m, 1 H), 5.61 (s, 2 H), 7.09–7.18 (m, 2 H), 7.22–7.25 (m, 1 H), 7.38 (d, J=7.8 Hz, 1 H), 7.74–7.77 (m, 1 H), 7.97–8.00 (m, 1 H), 8.24 (s, 1 H);

MS m/e 420 (MH$^+$);

2-(3-Isopropyl-2-oxo-2,3-dihydro-benzoimidazol-1-ylmethyl)-3-(3-methyl-butyl)-3H-benzoimidazole-5-carboxylic Acid Methyl Ester

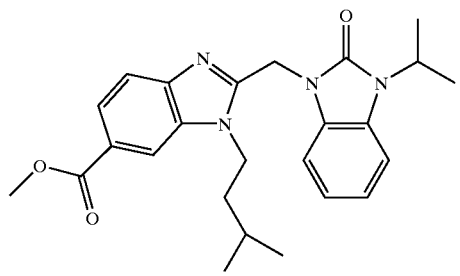

63

2-(3-Isopropyl-2-oxo-2,3-dihydro-benzoimidazol-1-ylmethyl)-3-(3-methyl-butyl)-3H-benzoimidazole-5-carboxylic acid methyl ester was prepared by the same procedure as the first step of making 1-[5-hydroxymethyl-1-(3-methyl-butyl)-1H-benzoimidazol-2-ylmethyl]-3-isopropyl-1,3-dihydro-benzoimidazol-2-one.

$^1$H NMR (CDCl$_3$) δ: 0.96 (d, J=6.6 Hz, 6 H), 1.45–1.58 (m, 2 H), 1.56 (d, J=7.0 Hz, 6 H), 1.69–1.73 (m, 1 H), 3.95 (s, 3 H), 4.37 (t, J=8.2 Hz, 2 H), 4.73–4.77 (m, 1 H), 5.39 (s, 2 H), 7.02–7.06 (m, 2 H), 7.13 (d, J=7.5 Hz, 1 H), 7.41–7.43 (m, 1 H), 7.79 (d, J=8.6 Hz, 1 H), 7.96–7.98 (m, 1 H), 8.05 (s, 1 H);

MS m/e 435 (MH$^+$);

1-[6-Hydroxymethyl-1-(3-methyl-butyl)-1H-benzoimidazol-2-ylmethyl]-3-isopropyl-1,3-dihydro-benzoimidazol-2-one

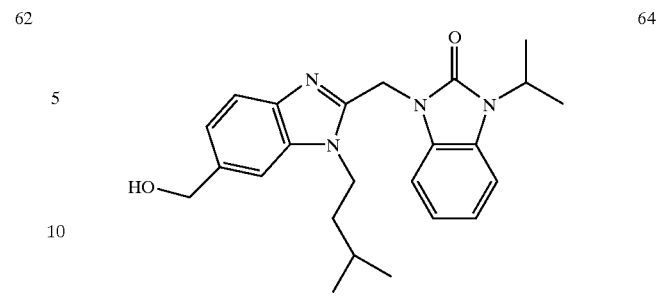

64

1-[6-Hydroxymethyl-1-(3-methyl-butyl)-1H-benzoimidazol-2-ylmethyl]-3-isopropyl-1,3-dihydro-benzoimidazol-2-one was prepared by the same procedure as the second step of making 1-[5-hydroxymethyl-1-(3-methyl-butyl)-1H-benzoimidazol-2-ylmethyl]-3-isopropyl-1,3-dihydro-benzoimidazol-2-one.

$^1$H NMR (CDCl$_3$) δ: 0.94 (d, J=6.6 Hz, 6 H), 1.40–1.43 (m, 2 H), 1.55 (d, J=7.0 Hz, 6 H), 1.69–1.73 (m, 1 H), 4.30 (t, J=8.2 Hz, 2 H), 4.75–4.78 (m, 1 H), 4.82 (d, J=5.5 Hz, 2 H), 5.37 (s, 2 H), 7.02–7.04 (m, 2 H), 7.12 (d, J=7.7 Hz, 1 H), 7.24–7.26 (m, 1 H), 7.33 (s, 1 H), 7.41 (d, J=7.6 Hz, 1 H), 7.76 (d, J=8.2 Hz, 1 H);

MS m/e 407 (MH$^+$).

1-[6-Chloromethyl-1-(3-methyl-butyl)-1H-benzoimidazol-2-ylmethyl]-3-isopropyl-1,3-dihydro-benzoimidazol-2-one

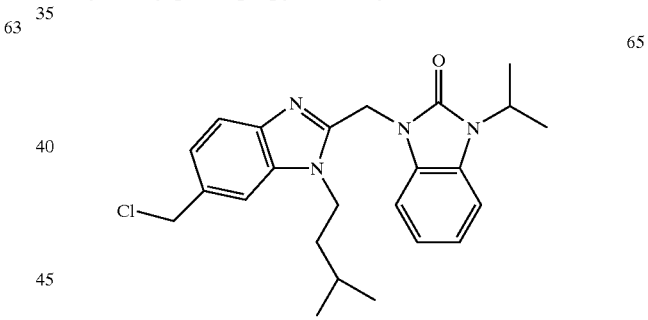

65

1-[6-Chloromethyl-1-(3-methyl-butyl)-1H-benzoimidazol-2-ylmethyl]-3-isopropyl-1,3-dihydro-benzoimidazol-2-one was prepared by the same procedure as 5-bromo-2-chloromethyl-1-(3-methyl-butyl)-1H-benzoimidazole.

$^1$H NMR (CD$_3$OD) δ: 0.98 (d, J=6.6 Hz, 6 H), 1.58 (d, J=7.0 Hz, 6 H), 1.66–1.75 (m, 3 H), 4.55 (t, J=8.2 Hz, 2 H), 4.71–4.74 (m, 1 H), 4.88 (s, 2 H), 5.70 (s, 2 H), 7.17–7.23 (m, 2 H), 7.26–7.28 (m, 1 H), 7.42 (d, J=7.6 Hz, 1 H), 7.70–7.75 (m, 2 H), 7.98 (s, 1 H);

MS m/e 425 (MH$^+$).

1-[6-Dimethylaminomethyl-1-(3-methyl-butyl)-1H-benzoimidazol-2-ylmethyl]-3-isopropyl-1,3-dihydro-benzoimidazol-2-one

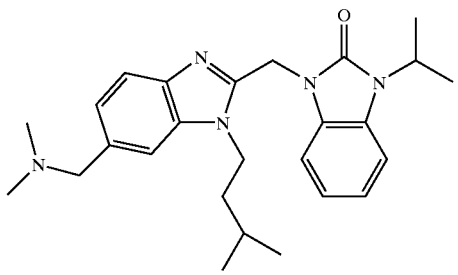

1-[6-Dimethylaminomethyl-1-(3-methyl-butyl)-1H-benzoimidazol-2-ylmethyl]-3-isopropyl-1,3-dihydro-benzoimidazol-2-one was prepared by the same procedure as 1-[5-methylaminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 0.98 (d, J=6.6 Hz, 6 H), 1.53–1.62 (m, 8 H), 1.70–1.74 (m, 1 H), 2.88 (s, 6 H), 4.43–4.51 (m, 4 H), 4.72–4.76 (m, 1 H), 5.55 (s, 2 H), 7.07–7.10 (m, 1 H), 7.13–7.17 (m, 1 H), 7.21–7.24 (m, 1 H), 7.35–7.38 (m, 1 H), 7.50–7.52 (m, 1 H), 7.78–7.83 (m, 2 H);

MS m/e 434 (MH$^+$).

1-Isopropyl-3-[6-methylaminomethyl-1-(3-methyl-butyl)-1H-benzoimidazol-2-ylmethyl]-1,3-dihydro-benzoimidazol-2-one

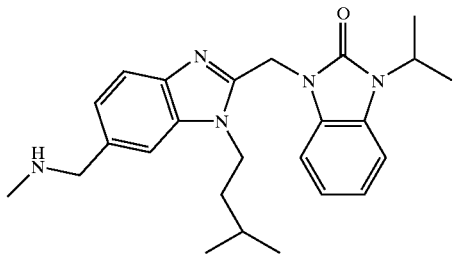

1-Isopropyl-3-[6-methylaminomethyl-1-(3-methyl-butyl)-1H-benzoimidazol-2-ylmethyl]-1,3-dihydro-benzoimidazol-2-one was prepared by the same procedure as 1-[5-methylaminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 0.98 (d, J=6.6 Hz, 6 H), 1.53–1.61 (m, 8 H), 1.70–1.74 (m, 1 H), 2.76 (s, 3 H), 4.36 (d, J=6.4 Hz, 2 H), 4.45 (t, J=8.1 Hz, 2 H), 4.72–4.76 (m, 1 H), 5.55 (s, 2 H), 7.07–7.10 (m, 1 H), 7.14–7.16 (m, 1 H), 7.20–7.23 (m, 1 H), 7.35–7.38 (m, 1 H), 7.49–7.52 (m, 1 H), 7.76–7.79 (m, 2 H);

MS m/e 420 (MH$^+$).

[2-(3-Isopropyl-2-oxo-2,3-dihydro-benzoimidazol-1-ylmethyl)-3-(3-methyl-butyl)-3H-benzoimidazol-5-yl]-acetonitrile

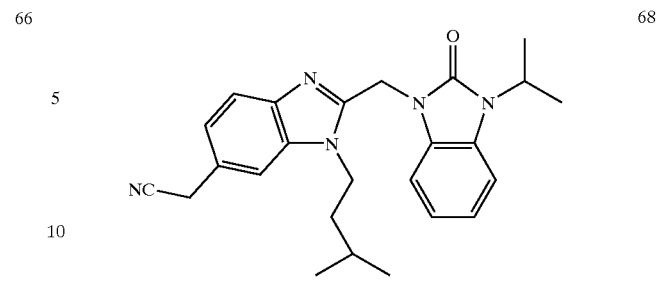

[2-(3-Isopropyl-2-oxo-2,3-dihydro-benzoimidazol-1-ylmethyl)-3-(3-methyl-butyl)-3H-benzoimidazol-5-yl]-acetonitrile was prepared by the same procedure as [2-(3-isopropyl-2-oxo-2,3-dihydro-benzoimidazol-1-ylmethyl)-1-(3-methyl-butyl)-1H-benzoimidazol-5-yl]-acetonitrile and was used without further purification in the next reaction.

MS m/e 416 (MH$^+$).

1-[6-(2-Amino-ethyl)-1-(3-methyl-butyl)-1H-benzoimidazol-2-ylmethyl]-3-isopropyl-1,3-dihydro-benzoimidazol-2-one

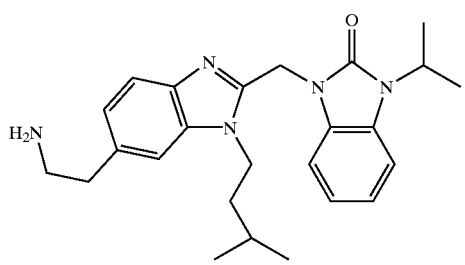

1-[6-(2-Amino-ethyl)-1-(3-methyl-butyl)-1H-benzoimidazol-2-ylmethyl]-3-isopropyl-1,3-dihydro-benzoimidazol-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 0.95 (d, J=6.6 Hz, 6 H), 1.49–1.59 (m, 8 H), 1.68–1.72 (m, 1 H), 3.12 (t, J=7.0 Hz, 2 H), 3.24 (t, J=7.5 Hz, 2 H), 4.41 (t, J=8.2 Hz, 2 H), 4.71–4.78 (m, 1 H), 5.51 (s, 2 H), 7.04–7.20 (m, 3 H), 7.32–7.37 (m, 2 H), 7.52 (s, 1 H), 7.67 (d, J=8.4 Hz, 1 H);

MS m/e 420 (MH$^+$).

3-[5-Cyano-1-(3-methyl-butyl)-1H-benzoimidazol-2-ylmethyl]-2-oxo-2,3-dihydro-benzoimidazole-1-carboxylic Acid Ethyl Ester

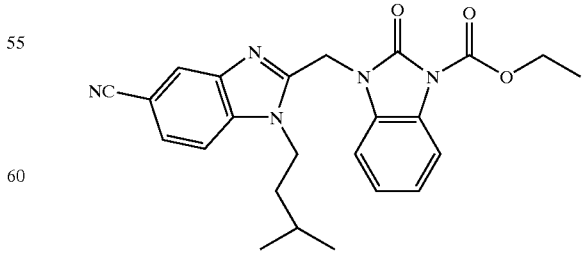

3-[5-Cyano-1-(3-methyl-butyl)-1H-benzoimidazol-2-ylmethyl]-2-oxo-2,3-dihydro-benzoimidazole-1-carboxylic acid ethyl ester was prepared by the same procedure as 2-(3-isopropyl-2-oxo-2,3-dihydro-benzoimidazol-1-ylmethyl)-1-(3-methyl-butyl)-1H-benzoimidazole-5-carbonitrile, except using 2-oxo-2,3-dihydro-benzoimidazole-1-carboxylic acid ethyl ester (N. Meanwell et al, *J. Org. Chem*, 1995, 60(6), 1565–82) and was used without purification in the next reaction.

MS m/e 420 (MH⁺).

1-(3-Methyl-butyl)-2-(2-oxo-2,3-dihydro-benzoimidazol-1-ylmethyl)-1H-benzoimidazole-5-carbonitrile

71

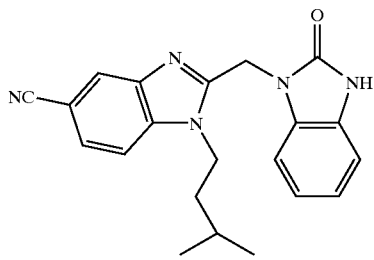

A solution of 3-[5-cyano-1-(3-methyl-butyl)-1H-benzoimidazol-2-ylmethyl]-2-oxo-2,3-dihydro-benzoimidazole-1-carboxylic acid ethyl ester in dimethylamine/THF (1M, 2 mL) was stirred at ambient temperature for 12 h. After the solvent was removed, the residue was used as crude for the next reaction without purification.

MS m/e 360 (MH⁺).

1-[5-Aminomethyl-1-(3-methyl-butyl)-1H-benzoimidazol-2-ylmethyl]-1,3-dihydro-benzoimidazol-2-one

72

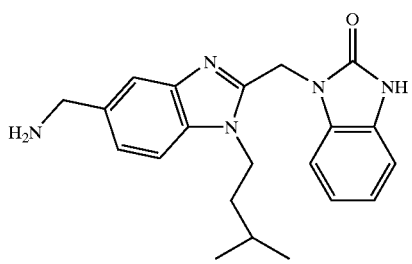

1-[5-Aminomethyl-1-(3-methyl-butyl)-1H-benzoimidazol-2-ylmethyl]-1,3-dihydro-benzoimidazol-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 0.95 (d, J=6.6 Hz, 6 H), 1.40–1.48 (m, 2 H), 1.67–1.72 (m, 1 H), 4.25 (s, 2 H), 4.41 (t, J=8.2 Hz, 2 H), 5.50 (s, 2 H), 7.00–7.06 (m, 1 H), 7.09–7.14 (m, 3 H), 7.47–7.50 (m, 1 H), 7.66 (d, J=8.5 Hz, 1 H), 7.80 (s, 1 H);

MS m/e 364 (MH⁺).

Cyclopropyl-(3-nitro-pyridin-4-yl)-amine

73

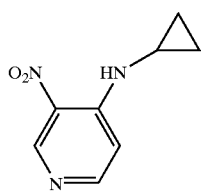

A solution of 4-methoxy-3-nitropyridine (7.71 g, 50 mmol) and cyclopropylamine (7.14 g, 125 mmol) in EtOH (20 mL) was heated at 80° C. in a sealed tube for 2 h. The solvent was evaporated to give cyclopropyl-(3-nitro-pyridin-4-yl)-amine as a yellow solid.

$^1$H NMR (CD$_3$OD) δ: 0.72–0.75 (m, 2 H), 0.99–1.03 (m, 2 H), 2.63–2.68 (m, 1 H), 7.19 (d, J=6.2 Hz, 1 H), 8.26 (b, 1 H), 8.35 (d, J=6.2 Hz, 1 H), 9.22 (s, 1 H);

IR (KBr, cm$^{-1}$): 3369, 1613, 1560, 1515, 1406, 1254, 1195, 1039, 881, 846, 769, 545;

MS m/e 180 (MH⁺).

N⁴-Cyclopropyl-pyridine-3,4-diamine

74

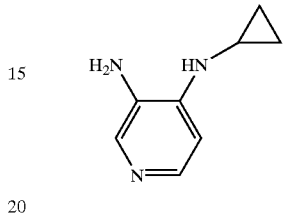

N-Cyclopropyl-pyridine-3,4-diamine was prepared by the same procedure as 1-isopropyl-1,3-dihydro-benzoimidazol-2-one and was used as crude without purification.

1-Cyclopropyl-1,3-dihydro-imidazo[4,5-c]pyridin-2-one

75

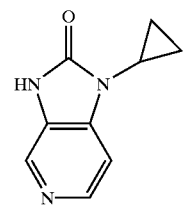

To a slurry of the diamine mentioned above and polyvinylpyridine (22.0 g) in acetonitrile (70 mL) was added a 20% phosgene in toluene dropwise (70 mL, 135 mmol). After stirring at room temperature for 2 h, the reaction was quenched with water. Polyvinylpyridine was removed by filtration and rinsed with MeOH. The filtrate was concentrated and Et$_2$O was added to precipitate 1-cyclopropyl-1,3-dihydro-imidazo[4,5-c]pyridin-2-one (15.5 g, 98% yield) as an off-white solid.

$^1$H NMR (CD$_3$OD) δ: 0.95–0.98 (m, 2 H), 1.07–1.14 (m, 2 H), 2.91–2.96 (m, 1 H), 7.32 (dd, J=0.5, 5.3 Hz, 1 H), 7.18 (s, 1 H), 8.21 (d, J=5.3 Hz, 1 H);

MS m/e 176 (MH⁺).

2-(1-Cyclopropyl-2-oxo-1,2-dihydro-imidazo[4,5-c]pyridin-3-ylmethyl)-1-(3-methyl-butyl)-1H-benzoimidazole-5-carbonitrile

76

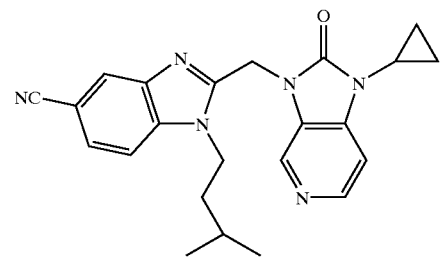

2-(1-Cyclopropyl-2-oxo-1,2-dihydro-imidazo[4,5-c]pyridin-3-ylmethyl)-1-(3-methyl-butyl)-1H-benzoimidazole-5-carbonitrile was prepared by the same procedure as 2-(3-isopropyl-2-oxo-2,3-dihydro-benzoimidazol-1-ylmethyl)-1-(3-methyl-butyl)-1H-benzoimidazole-5-carbonitrile, except using 1-cyclopropyl-1,3-dihydro-imidazo[4,5-c]pyridin-2-one.

$^1$H NMR (CDCl$_3$) δ: 0.99 (d, J=6.6 Hz, 6 H), 1.01–1.04 (m, 2 H), 1.15–1.19 (m, 2 H), 1.48–1.51 (m, 2 H), 1.69–1.72 (m, 1 H), 2.88–2.92 (m, 1 H), 4.34 (t, J=8.2 Hz, 2 H), 5.37 (s, 2 H), 7.14 (d, J=5.2 Hz, 1 H), 7.38 (d, J=8.4 Hz, 1 H), 7.53–7.55 (m, 1 H), 8.09 (s, 1 H), 8.34 (d, J=5.2 Hz, 1 H), 8.62 (s, 1 H);

MS m/e 401 (MH$^+$).

3-[5-Aminomethyl-1-(3-methyl-butyl)-1H-benzoimidazol-2-ylmethyl]-1-cyclopropyl-1,3-dihydro-imidazo[4,5-c]pyridin-2-one

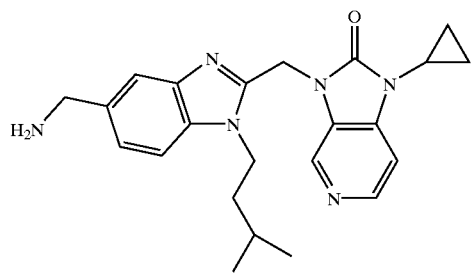

77

3-[5-Aminomethyl-1-(3-methyl-butyl)-1H-benzoimidazol-2-ylmethyl]-1-cyclopropyl-1,3-dihydro-imidazo[4,5-c]pyridin-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CDCl$_3$) δ: 1.06 (d, J=6.6 Hz, 6 H), 1.11–1.14 (m, 2 H), 1.19–1.29 (m, 2 H), 1.76–1.82 (m, 3 H), 3.13–3.19 (m, 1 H), 4.21 (s, 2 H), 4.46 (t, J=7.8 Hz, 2 H), 5.57 (s, 2 H), 7.43–7.46 (m, 1 H), 7.65–7.68 (m, 2 H), 7.89 (d, J=6.4 Hz, 1 H), 8.53 (d, J=6.6 Hz, 1 H), 8.72 (s, 1 H);

MS m/e 405 (MH$^+$).

1-(3-Methyl-butyl)-2-(2-oxo-2,3-dihydro-imidazo[4,5-c]pyridin-1-ylmethyl)-1H-benzoimidazole-5-carbonitrile

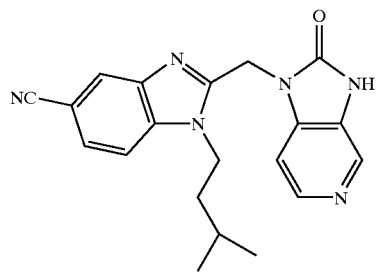

78

1-(3-Methyl-butyl)-2-(2-oxo-2,3-dihydro-imidazo[4,5-c]pyridin-1-ylmethyl)-1H-benzoimidazole-5-carbonitrile was prepared by the same procedure as 2-(3-isopropyl-2-oxo-2,3-dihydro-benzoimidazol-1-ylmethyl)-1-(3-methyl-butyl)-1H-benzoimidazole-5-carbonitrile, except using 2-oxo-2,3-dihydro-imidazo[4,5-c]pyridine-1-carboxylic acid tert-butyl ester (N. Meanwell et al, *J. Org. Chem*, 1995, 60(6), 1565–82), and was purified by prep-HPLC (gradient 10% B–100% B).

MS m/e 361 (MH$^+$).

1-[5-Aminomethyl-1-(3-methyl-butyl)-1H-benzoimidazol-2-ylmethyl]-1,3-dihydro-imidazo[4,5-c]pyridin-2-one

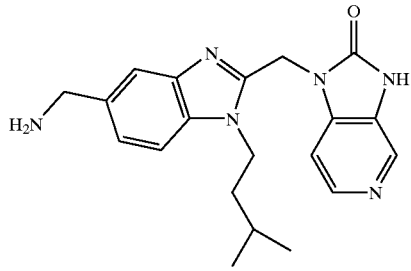

79

1-[5-Aminomethyl-1-(3-methyl-butyl)-1H-benzoimidazol-2-ylmethyl]-1,3-dihydro-imidazo[4,5-c]pyridin-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CDCl$_3$) δ: 1.05 (d, J=6.4 Hz, 6 H), 1.73–1.81 (m, 3 H), 4.22 (s, 2 H), 4.47 (t, J=7.9 Hz, 2 H), 5.63 (s, 2 H), 7.44–7.47 (m, 1 H), 7.63–7.70 (m, 2 H), 7.78 (d, J=6.4 Hz, 1 H), 8.45 (d, J=6.5 Hz, 1 H), 8.55 (s, 1 H);

MS m/e 365 (MH$^+$).

1,3-Bis-[5-cyano-(3-methyl-butyl)-1H-benzoimidazol-2-ylmethyl]-1,3-dihydro-imidazo[4,5-c]pyridin-2-one

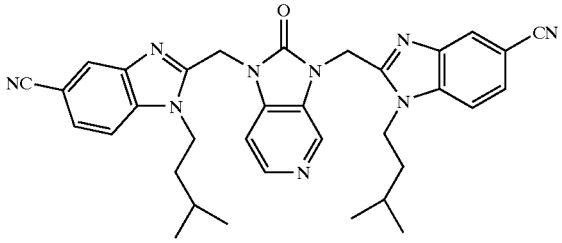

80

1,3-Bis-[5-cyano-(3-methyl-butyl)-1H-benzoimidazol-2-ylmethyl]-1,3-dihydro-imidazo[4,5-c]pyridin-2-one was obtained in the reaction of making 1-[5-cyano-1-(3-methyl-butyl)-1H-benzoimidazol-2-ylmethyl]-2-oxo-1,2-dihydro-imidazo[4,5-c]pyridine-3-carboxylic acid tert-butyl ester as by-product after prep-HPLC purification (gradient 10% B–100% B).

MS m/e 586 (MH$^+$).

1,3-Bis-[5-aminomethyl-1-(3-methyl-butyl)-1H-benzoimidazol-2-ylmethyl]-1,3-dihydro-imidazo[4,5-c]pyridin-2-one

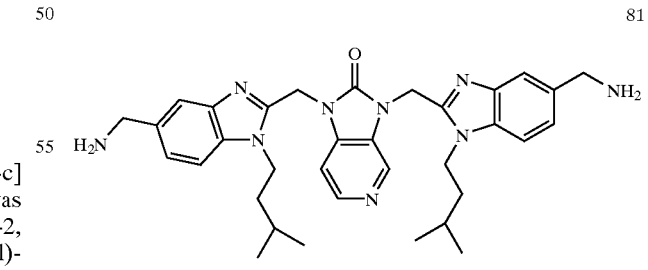

81

1,3-Bis-[5-aminomethyl-1-(3-methyl-butyl)-1H-benzoimidazol-2-ylmethyl]-1,3-dihydro-imidazo[4,5-c]pyridin-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CDCl$_3$) δ: 1.02 (d, J=6.4 Hz, 12 H), 1.74–1.80 (m, 6 H), 4.22 (s, 4 H), 4.47 (t, J=7.9 Hz, 4 H), 5.66 (s, 2 H), 5.70 (s, 2 H), 7.44–7.47 (m, 2 H), 7.64–7.71 (m, 4 H), 7.92 (d, J=6.4 Hz, 1 H), 8.55 (d, J=6.4 Hz, 1 H), 8.87 (s, 1 H);

MS m/e 594 (MH⁺).

4-(6-Hydroxy-hexylamino)-3-nitro-benzonitrile

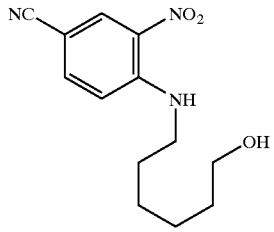

82

4-(6-Hydroxy-hexylamino)-3-nitro-benzonitrile was prepared by the same procedure as 4-(3-methyl-butylamino)-3-nitro-benzonitrile, except using 6-amino-hexan-1-ol instead.

$^1$H NMR (CDCl$_3$) δ: 1.44–1.51 (m, 4 H), 1.60–1.64 (m, 2 H), 1.75–1.81 (m, 2 H), 3.34–3.38 (m, 2 H), 3.66–3.69 (m, 2 H), 6.91 (d, J=9.0 Hz, 1 H), 7.59–7.61 (m, 1 H), 8.40 (b, 1 H), 8.51 (d, J=2.0 Hz, 1 H).

2,2-Dimethyl-propionic acid 6-(4-cyano-2-nitro-phenylamino)-hexyl Ester

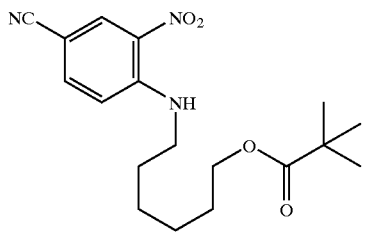

83

To a solution of 4-(6-hydroxy-hexylamino)-3-nitro-benzonitrile (13.2 g, 50.1 mmol) in pyridine (100 mL) was added trimethylacetyl chloride (6.65 g, 55.1 mmol) dropwise at 0° C. After stirring at ambient temperature for 3 h, the solvent was evaporated. The residue was taken up in EtOAc and was filtered. The filtrate was washed with water and brine, dried over MgSO$_4$ and evaporated. The residue was used as crude without purification.

MS m/e 348 (MH⁺).

2,2-Dimethyl-propionic Acid 6-(2-acetoxymethyl-5-cyano-benzoimidazol-1-yl)-hexyl Ester

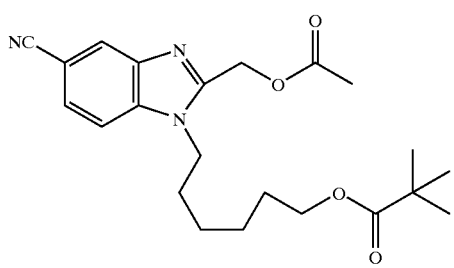

84

2,2-Dimethyl-propionic acid 6-(2-acetoxymethyl-5-cyano-benzoimidazol-1-yl)-hexyl ester was prepared by the same procedure as 5-cyano-1-(3-methyl-butyl)-1H-benzoimidazol-2-ylmethyl ester, except using 2,2-dimethyl-propionic acid 6-(4-cyano-2-nitro-phenylamino)-hexyl ester instead.

$^1$H NMR (CDCl$_3$) δ: 1.18 (s, 9 H), 1.41–1.42 (m, 4 H), 1.61–1.64 (m, 2 H), 1.83–1.86 (m, 2 H), 2.16 (s, 3 H), 4.04 (t, J=6.5 Hz, 2 H), 4.22 (t, J=7.5 Hz, 2 H), 5.38 (s, 2 H), 7.44 (d, J=8.4 Hz, 1 H), 7.57 (d, J=8.4 Hz, 1 H), 8.11 (s, 1 H);

MS m/e 400 (MH⁺).

Acetic Acid 6-(5-cyano-2-hydroxymethyl-benzoimidazol-1-yl)-hexyl Ester

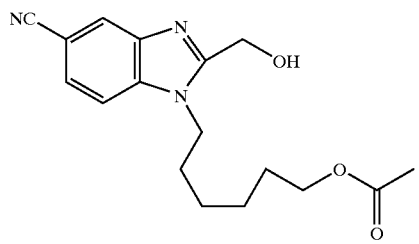

85

A mixture of 2,2-Dimethyl-propionic acid 6-(2-acetoxymethyl-5-cyano-benzoimidazol-1-yl)-hexyl ester (7.2 g, 18 mmol) and K$_2$CO$_3$ (14 g, 101 mmol) in MeOH (100 mL) was stirred at the ambient temperature for 4 h. The nixture was diluted with EtOAc (100 mL) and filtered. The filtrate was evaporated. The residue was dissolved in EtOAc (300 mL) and washed with water and brine. The organic layer was dried over MgSO$_4$ and evaporated. The residue was left for 2 weeks before being purified by flash chromatography (hexanes:acetone 1:1) to give 4.1 g (72%) of acetic acid 6-(5-cyano-2-hydroxymethyl-benzoimidazol-1-yl)-hexyl ester as a white solid.

$^1$H NMR (CDCl$_3$) δ 1.39–1.44 (m, 4 H), 1.61–1.62 (m, 2 H), 1.84–1.89 (m, 2 H), 2.03 (s, 3 H), 4.04 (t, J=6.6 Hz, 2 H), 4.19 (b, 1 H), 4.24 (t, J=7.5 Hz, 2 H), 4.91 (s, 2 H), 7.38–7.41 (m, 1 H), 7.52–7.55 (m, 1 H), 8.02 (d, J=0.8 Hz, 1 H);

MS m/e 316 (MH⁺).

Acetic Acid 6-(2-chloromethyl-5-cyano-benzoimidazol-1-yl)-hexyl Ester

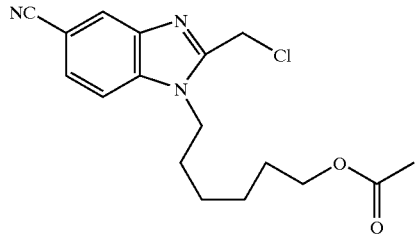

86

Acetic acid 6-(2-chloromethyl-5-cyano-benzoimidazol-1-yl)-hexyl ester was prepared by the same procedure as 5-bromo-2-chloromethyl-1-(3-methyl-butyl)-1H-benzoimidazole and was used as crude.

MS m/e 334 (MH⁺).

Acetic Acid 6-[5-cyano-2-(1-cyclopropyl-2-oxo-1,2-dihydroimidazo[4,5c]pyridin-3-ylmethyl)-benzoimidazol-1-yl]-hexyl Ester

87

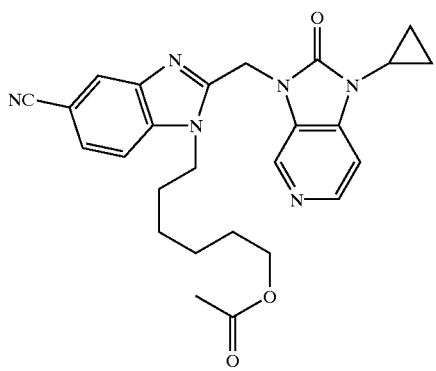

Acetic acid 6-[5-cyano-2-(1-cyclopropyl-2-oxo-1,2-dihydro-imidazo[4,5-c]pyridin-3-ylmethyl)-benzoimidazol-1-yl]-hexyl ester was prepared by the same procedure as 2-(3-isopropyl-2-oxo-2,3-dihydro-benzoimidazol-1-ylmethyl)-1-(3-methyl-butyl)-1H-benzoimidazole-5-carbonitrile and was used without further purification.

$^1$H NMR (CDCl$_3$) δ: 1.00–1.04 (m, 2 H), 1.15–1.20 (m, 2 H), 1.34–1.38 (m, 4 H), 1.54–1.58 (m, 2 H), 1.64–1.68 (m, 2 H), 2.03 (s, 3 H), 2.90–2.94 (m, 1 H), 4.02 (t, J=6.6 Hz, 2 H), 4.35 (t, J=7.5 Hz, 2 H), 5.37 (s, 2 H), 7.13–7.15 (m, 1 H), 7.39 (d, J=8.4 Hz, 1 H), 7.52–7.55 (m, 1 H), 8.10 (d, J=0.8 Hz, 1 H), 8.35 (d, J=5.2 Hz, 1 H), 8.65 (s, 1 H);

MS m/e 473 (MH$^+$);

2-(1-Cyclopropyl-2-oxo-1,2-dihydro-imidazo[4,5-c]pyridin-3-ylmethyl)-1-(6-hydroxy-hexyl)-1H-benzoimidazole-5-carbonitrile

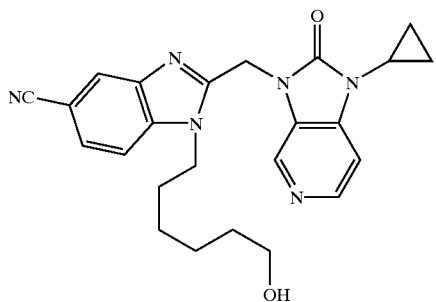

2-(1-Cyclopropyl-2-oxo-1,2-dihydro-imidazo[4,5-c]pyridin-3-ylmethyl)-1-(6-hydroxy-hexyl)-1H-benzoimidazole-5-carbonitrile was prepared by the same procedure as acetic acid 6-(5-cyano-2-hydroxymethyl-benzoimidazol-1-yl)-hexyl ester and was used without further purification.

MS m/e 431 (MH$^+$);

3-[5-Aminomethyl-1-(6-hydroxy-hexyl)-1H-benzoimidazol-2-ylmethyl]-1-cyclopropyl-1,3-dihydro-imidazo[4,5-c]pyridin-2-one

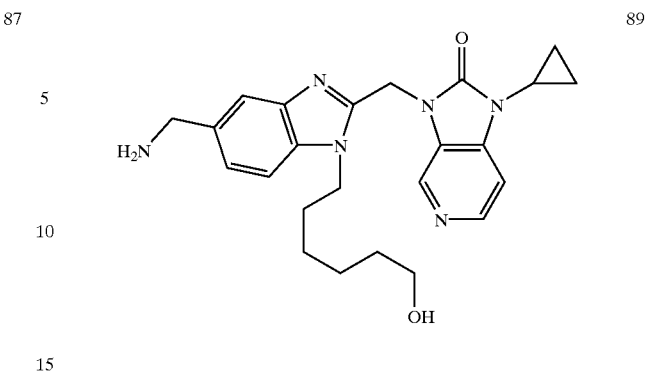

3-[5-Aminomethyl-1-(6-hydroxy-hexyl)-1H-benzoimidazol-2-ylmethyl]-1-cyclopropyl-1,3-dihydro-imidazo[4,5-c]pyridin-2-one was prepared by the same procedure as 1-[5-aminomethyl-1-(3-methyl-butyl)-1H-benzoimidazol-2-ylmethyl]-3-isopropyl-1,3-dihydro-benzoimidazol-2-one.

$^1$H NMR (CD$_3$OD) δ: 1.16–1.18 (m, 2 H), 1.21–1.25 (m, 2 H), 1.49–1.58 (m, 6 H), 2.01–2.03 (m, 2 H), 3.18–3.21 (m, 1 H), 3.56 (t, J=6.2 Hz, 2 H), 4.30 (s, 2 H), 4.63 (t, J=7.2 Hz, 2 H), 5.90 (s, 2 H), 7.71 (d, J=8.2 Hz, 1 H), 7.88 (s, 1 H), 7.93 (d, J=6.4 Hz, 1 H), 8.01 (d, J=8.6 Hz, 1 H), 8.60 (d, J=6.4 Hz, 1 H), 8.93 (s, 1 H);

MS m/e 435 (MH$^+$).

2-(3-Bromo-pyrazolo[3,4-c]pyridin-1-ylmethyl)-1-(3-methyl-butyl)-1H-benzoimidazole-5-carbonitrile

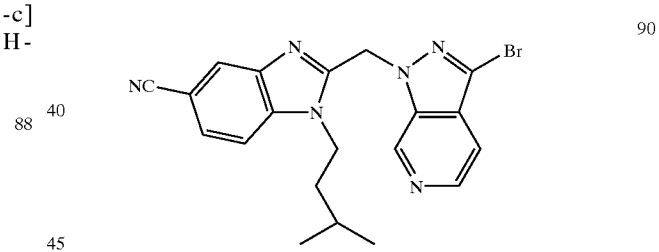

2-(3-Bromo-pyrazolo[3,4-c]pyridin-1-ylmethyl)-1-(3-methyl-butyl)-1H-benzoimidazole-5-carbonitrile was prepared by the same procedure as 2-(3-isopropyl-2-oxo-2,3-dihydro-benzoimidazol-1-ylmethyl)-1-(3-methyl-butyl)-1H-benzoimidazole-5-carbonitrile, except using 3-bromo-1H-pyrazolo[3,4-c]pyridine (D. Chapman et al, *J. Chem. Soc. Perkin Trans. I,* 1980, 2398).

$^1$H NMR (CDCl$_3$) δ: 0.97 (d, J=6.6 Hz, 6 H), 1.26–1.30 (m, 2 H), 1.65–1.75 (m, 1 H), 4.30 (t, J=8.4 Hz, 2 H), 5.98 (s, 2 H), 7.37–7.38 (m, 1 H), 7.51–7.56 (m, 2 H), 8.12 (d, J=0.8 Hz, 1 H), 8.41 (d, J=5.6 Hz, 1 H), 9.21 (d, J=0.8 Hz, 1 H);

MS m/e 423, 425 (MH$^+$).

1-[5-(1-Amino-1-methyl-ethyl)-1-(3-methyl-butyl)-1H-benzoimidazol-2-ylmethyl]-3-isopropyl-1,3-dihydro-benzoimidazol-2-one

91

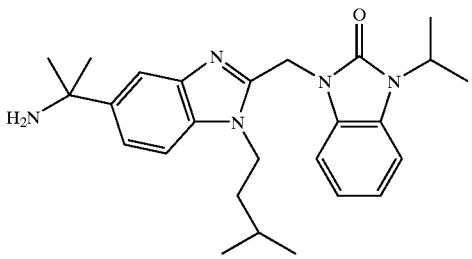

To a solution of 2-(3-isopropyl-2-oxo-2,3-dihydro-benzoimidazol-1-ylmethyl)-1-(3-methyl-butyl)-1H-benzoimidazole-5-carbonitrile (80 mg, 0.2 mmol) in THF (1 mL) was added methylcerium dichloride (E. Ciganek *J. Org. Chem*, 1992, 57 (16), 4521, 0.16 M in THF, 7.5 mL, 1.2 mmol) at −78° C. The final mixture was warmed to 0° C. with stirring. The reaction mixture was quenched with conc. ammonium hydroxide at 0° C. and filtered through celite. The filtrate was extracted with DCM twice. The combined organic layer was washed with brine, dried over MgSO$_4$ and evaporated. The residue was purified by prep-HPLC (gradient 10% B–100% B) to give 55 mg (64%) of 1-[5-(1-amino-1-methyl-ethyl)-1-(3-methyl-butyl)-1H-benzoimidazol-2-ylmethyl]-3-isopropyl-1,3-dihydro-benzoimidazol-2-one as an off-white solid.

$^1$H NMR (CD$_3$OD) δ: 0.93 (d, J=6.6 Hz, 6 H), 1.48–1.53 (m, 2 H), 1.57 (d, J=7.0 Hz, 6 H), 1.64–1.77 (m, 1 H), 1.80 (s, 6 H), 4.42 (t, J=8.2 Hz, 2 H), 4.72–4.75 (m, 1 H), 5.51 (s, 2 H), 7.05 (t, J=7.7 Hz, 1 H), 7.14 (t, J=7.7 Hz, 1 H), 7.18 (d, J=7.8 Hz, 1 H), 7.35 (d, J=7.9 Hz, 1 H), 7.59 (d, J=8.6 Hz, 1 H), 7.69 (d, J=8.7 Hz, 1 H), 7.81 (d, J=1.7 Hz, 1 H);

MS m/e 434 (MH$^+$).

[5-aminomethyl-1-(3-methyl-butyl)-1H-benzoimidazol-2-yl]-methanol, HCl salt and C-[2-Benzyloxymethyl-1-(3-methyl-butyl)-1H-benzoimidazol-5-yl]-methylamine; HCl Salt

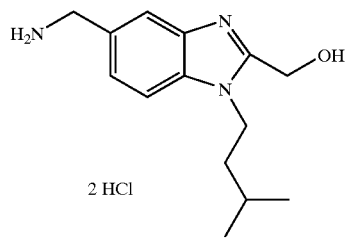

92a

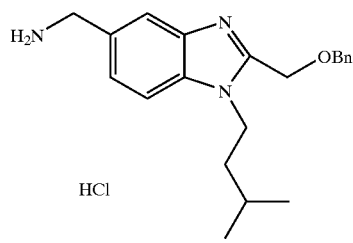

92b

To a solution 2-benzyloxymethyl-1-(3-methyl-butyl)-1H-benzoimidazole-5-carbonitrile (1.12 g, 3.36 mmol) in methanol (50 mL) and concentrated HCl (2.5 mL) was added 10% Pd/C (120 mg). This mixture was rocked under a hydrogen atmosphere in a Parr shaker(45 psi) for 48 hrs. The catalyst was removed by filtration and the solution concentrated in vacuo to give [5-aminomethyl-1-(3-methyl-butyl)-1H-benzoimidazol-2-yl]-methanol (1.14 g, 100%) as a tan solid. A small portion was purified by prep HPLC (30–100% B) to give C-[2-Benzyloxymethyl-1-(3-methyl-butyl)-1H-benzoimidazol-5-yl]-methylamine; HCl salt:

[5-aminomethyl-1-(3-methyl-butyl)-1H-benzoimidazol-2-yl]-methanol: $^1$H NMR (CD$_3$OD) δ: 1.05 (d, J=6.3, 6H), 1.81 (bs, 3 H), 4.37 (s, 2H), 4.48 (br s, 2H), 5.18 (s, 2H), 7.78 (d, J=8.5, 1H), 7.98 (d, J=8.5, 1H), 8.02 (s, 1H);

MS m/e 248 (MH$^+$).

C-[2-Benzyloxymethyl-1-(3-methyl-butyl)-1H-benzoimidazol-5-yl]-methylamine; HCl salt: $^1$H NMR (CD$_3$OD) δ: 0.98 (d, J=6.3, 6H), 1.69–1.76 (m, 3H), 4.39–4.42 (m, 2H), 4.80 (s, 2H), 5.06 (s, 2 H), 7.31–7.45 (m, 5H), 7.53 (d, J=8.6 Hz, 1 H), 7.60 (s, 1H), 7.76 (d, J=8.6, 1H);

MS m/e 337 (MH$^+$).

[2-Hydroxymethyl-1-(3-methyl-butyl)-1H-benzoimidazol-5-ylmethyl]-carbamic Acid tert-butyl Ester

93

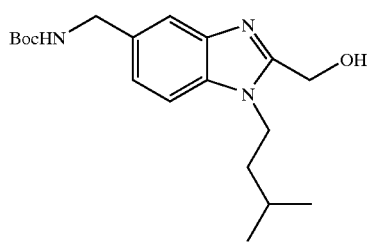

To a cooled (0° C.) solution of [5-aminomethyl-1-(3-methyl-butyl)-1H-benzoimidazol-2-yl]-methanol (558 mg, 1.74 mmol) and DIPEA (667 µL, 3.83 mmol) in DMF (6 mL) was added Boc$_2$O (342 mg, 1.57 mmol) in one portion. After stirring at the same temperature for 20 min. the volatiles were removed in vacuo. Water was added to the residue and the product extracted into ethyl acetate (2×15 mL). The combined organic extracts were washed with water, brine and dried over MgSO$_4$ and concentrated. The residue was purified by flash column chromatography (eluent 5% MeOH in CH$_2$Cl$_2$) to give [2-hydroxymethyl-1-(3-methyl-butyl)-1H-benzoimidazol-5-ylmethyl]-carbamic acid tert-butyl ester (430 mg, 71%) as a white solid.

$^1$H NMR (CDCl$_3$) δ: 0.99 (d, J=6.0, 6H), 1.46 (s, 9H), 1.68–1.70 (m, 3H), 4.20 (t, J=7.4, 2H), 4.36 (d, J=5.2, 2H), 4.84 (s, 2H), 4.94 (br s, 1H), 5.83 (br s, 1H), 7.19–7.26 (m, 2H), 7.49 (s, 1H);

MS m/e 348 (MH$^+$).

[2-Chloromethyl-1-(3-methyl-butyl)-1H-benzoimidazol-5-ylmethyl]-carbamic Acid tert-butyl Ester; HCl Salt

94

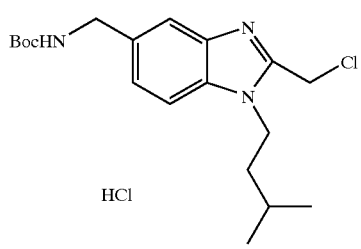

To a cooled (0° C.) solution of [2-hydroxymethyl-1-(3-methyl-butyl)-1H-benzoimidazol-5-ylmethyl]-carbamic acid tert-butyl ester (146 mg, 0.42 mmol) in DCM (5 mL) was added thionyl chloride (46 µL, 0.63 mmol). The solution was stirred at 0° C. for 15 min. and concentrated in vacuo to give [2-chloromethyl-1-(3-methyl-butyl)-1H-benzoimidazol-5-ylmethyl]-carbamic acid tert-butyl ester; HCl salt (176 mg, 100%) as a white solid, which was used without further purification.

¹H NMR (DMSO-d6) δ: 0.98 (d, J=6.1, 6H), 1.40 (s, 9H), 1.71–1.74 (m, 3H), 4.28 (d, J=5.7, 2H), 4.44–4.46 (m, 2H), 5.31 (s, 2H), 7.44 (d, J=8.5, 1H), 7.55 (br s, 1H), 7.63 (s, 1H), 7.81 (d, J=8.5, 1H);

MS m/e 366 (MH⁺).

3,3-Dibromo 7-aza Oxindole

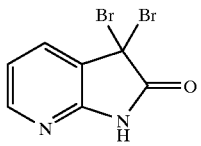

3,3-Dibromo 7-aza oxindole was prepared using a procedure described by Marfat, etc (*Tetrahedron Lett.,* 1987, 28, 4027–4031) or using the procedure below.

To a solution of 7-azaindole (2.0 g, 0.016 mol) in tert. BuOH (120 mL) was added PyBr₃ in portions. The resulting mixture was stirred at room temperature for 15 hours. The solvent was removed in vacuo and the residue was suspended in water (250 mL). The aqueous phase was extracted with ethyl acetate (2×150 mL) and the combined organic fractions were washed with water (2×100 mL) and brine (50 mL). The organic phase was dried (MgSO₄) and evaporated. The residue was triturated in methylene chloride and filtered to afford 3.72 g of 3,3-dibromo 7-aza oxindole (80%) as a white-brown solid:

¹H NMR (CDCl₃) δ 8.25 (dd, J=1.4, 5.3 Hz, 1H), 7.88 (dd, J=1.4, 7.6 Hz, 1H), 7.16 (dd, J=5.3, 7.6 Hz, 1H);

MS m/e 293 (MH⁺).

1H-Pyrrolo[2,3-b]pyridine-2,3-dione 3-[O-(2-fluoro-ethyl)-oxime]

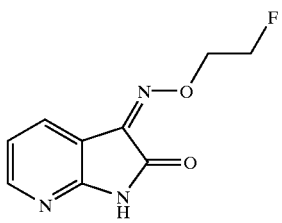

A solution of 3,3-dibromo 7-aza oxindole (300 mg, 1.03 mmol) in DMSO (25 mL) was heated at 95° C. under house vacuum for 6.5 hours. The solution containing the corresponding 7-aza isatin was cooled to room temperature, followed by the addition O-(2-fluoro-ethyl)-hydroxylamine hydrochloride (prepared as described by Ishikawa et al *J. Antibiot.,* 2000, 53, 1071) (131 mg, 1.13 mmol). After stirring for 1 hour at room temperature the mixture was quenched with water and extracted with ethyl acetate (6×25 mL). The combined organic phases were washed with brine and dried over MgSO₄. The solvent was removed in vacuo and the residue purified by flash column chromatography (gradient, 2% MeOH in methylene chloride to 3%) to give 1H-pyrrolo[2,3-b]pyridine-2,3-dione 3-[O-(2-fluoro-ethyl)-oxime] (200 mg, 93%) as an orange solid that was further purified by trituration from diethyl ether-DCM (1:1).

¹H NMR (DMSO) δ 11.5 (s, 1 H), 4.57–4.84 (m, 4 H), 7.08 (m, 1 H), 8.10 (d, J=7.0 Hz, 1 H), 8.24 (d, J=4.1 Hz, 1 H);

MS m/e 210 (MH⁺).

[2-[3-(2-Fluoro-ethoxyimino)-2-oxo-2,3-dihydro-pyrrolo[2,3-b]pyridin-1-ylmethyl]-1-(3-methyl-butyl)-1H-benzoimidazol-5-ylmethyl]-carbamic Acid tert-butyl Ester

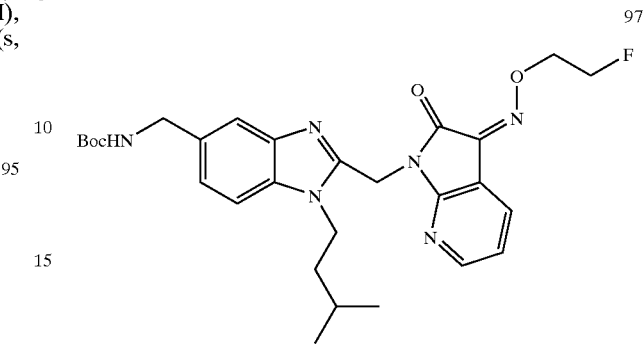

To a solution of 1H-pyrrolo[2,3-b]pyridine-2,3-dione 3-[O-(2-fluoro-ethyl)-oxime] (23 mg, 0.11 mmol) in DMF (1.6 mL) was added Cs₂CO₃ (108 mg, 0.33 mmol). After stirring for 20 minutes, [2-chloromethyl-1-(3-methyl-butyl)-1H-benzoimidazol-5-ylmethyl]-carbamic acid tert-butyl ester; HCl salt (44 mg, 0.11 mmol) was added and the resulting mixture was stirred at room temperature overnight. The solvent was removed in vacuo and the residue partitioned between ethyl acetate and water. The aqueous phase was extracted with ethyl acetate and the combined organic fractions washed with water, brine, dried over MgSO₄ and evaporated. The residue was purified by flash chromatography (eluant 1%, 5% MeOH in CH₂Cl₂) to give [2-[3-(2-fluoro-ethoxyimino)-2-oxo-2,3-dihydro-pyrrolo[2,3-b]pyridin-1-ylmethyl]-1-(3-methyl-butyl)-1H-benzoimidazol-5-ylmethyl]-carbamic acid tert-butyl ester (53 mg, 72%) as an off-white solid:

¹H NMR (DMSO-d6) δ: 0.96 (d, J=6.1, 6H), 1.37 (s, 9H), 1.63–1.67 (m, 3H), 4.16 (d, J=6.0, 2H), 4.30–4.33 (m, 2H), 4.71–4.89 (m, 4H), 5.25 (s, 2H), 7.12 (d, J=8.4, 1H), 7.17 (dd, J=5.3, 7.4, 1H), 7.32–7.34 (m, 2H), 7.45 (d, J=8.3, 1H), 8.23 (d, J=7.4, 1H), 8.26 (d, J=5.3, 1H);

MS m/e 539 (MH⁺).

1-[5-Aminomethyl-1-(3-methyl-butyl)-1H-benzoimidazol-2-ylmethyl]-1H-pyrrolo[2,3-b]pyridine-2,3-dione 3-[O-(2-fluoro-ethyl)-oxime]; HCl Salt To a cooled (0° C.) solution of [2-[3-(2-fluoro-ethoxyimino)-2-oxo-2,3-dihydro-pyrrolo[2,3-b]pyridin-1-ylmethyl]-1-(3-methyl-butyl)-1H-benzoimidazol-5-ylmethyl]-carbamic acid tert-butyl ester (15 mg, 0.028 mmol) and anisole (30 μL, 0.28 mmol) in DCM (0.5 mL) was added 4N HCl in dioxane (42 μL, 0.17 mmol). After 30 min. the solution was allowed to reach room temperature and more 4N HCl in dioxane (10 μL) was added. After 3 h. the volatiles were removed in vacuo, stripped with methanol (3 times), and the residue was triturated in diethyl ether. 1-[5-Aminomethyl-1-(3-methyl-butyl)-1H-benzoimidazol-2-ylmethyl]-1H-pyrrolo[2,3-b]pyridine-2,3-dione 3-[O-(2-fluoro-ethyl)-oxime]; HCl salt (9 mg, 69%) was collected by filtration as a yellow, hygroscopic solid:

$^1$H NMR (DMSO-d6) δ: 0.97 (d, J=5.2, 6H), 1.70 (m, 3H), 4.15 (d, J=4.1, 2H), 4.48 (br s, 2H), 4.73–4.89 (m, 4H), 5.46 (s, 2H), 7.21 (t, J=6.2, 1H), 7.57 (br s, 1H), 7.83–7.85 (m, 2H), 8.25–8.26 (m, 2H), 8.44 (br s, 3H);

MS m/e 439 (MH$^+$).

2-Amino-N-cyclopropyl-benzamide

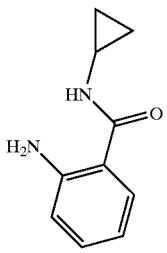

99

To a mixture of anthranilic acid (10 g, 72.2 mmol) in DMF (80 ml) was added HOBT (10.0 g, 72.99 mmol), EDC (13.9 g, 72.99 mmol) and cyclopropyl amine (4.2 g, 72.9 mmol). The mixture was stirred for 24 h at 23° C. then concentrated. The solvent was removed and the residue dissolved in EtOAc and washed with 1N HCl, saturated NaHCO$_3$ then the organic layer was dried over MgSO$_4$ and concentrated to give 6.7 g (52%) of 2-amino-N-cyclopropyl-benzamide as a tan solid.

$^1$H NMR (DMSO-d6) δ: 0.52–0.55 (m, 2H), 0.64–0.67 (m, 2H), 2.76–2.81 (m, 1H), 6.38 (br s, 2H), 6.47 (t, J=7.5 Hz, 11H), 6.66 (d, J=8.2 Hz, 1H), 7.11 (t, J=7.5 Hz, 1H), 7.40 (dd, J=1.4 Hz, 7.8 Hz, 1H), 8.15 (d, J=3.3 Hz, 1H);

MS m/e 176 (MH$^+$).

(2-Cyclopropylcarbamoyl-phenyl)-carbamic Acid Methyl Ester

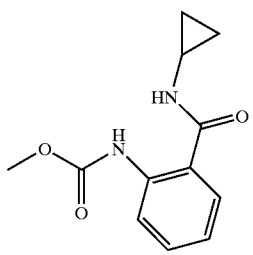

100

To a slurry of 2-amino-N-cyclopropyl-benzamide (6.7 g, 38.1 mmol) in water was added KHCO$_3$ (9.5 g, 95.1 mmol) followed by careful addition of methylchloroformate (5.88 ml, 76.2 mmol). The mixture was stirred for 12 h then the aqueous layer was extracted with EtOAc. The EtOAc extract was washed with 1N HCl then dried over MgSO$_4$ and concentrated to give 8.9 g (99%) of (2-cyclopropylcarbamoyl-phenyl)-carbamic acid methyl ester.

$^1$H NMR (DMSO-d6) δ: 0.58–0.61 (m, 2H), 0.69–0.73 (m, 2H), 2.84–2.86 (m, 1H), 3.68 (s, 3H), 7.07 (t, J=7.6 Hz, 1H), 7.48 (t, J=7.6 Hz, 1H), 8.15 (d, J=8.1 Hz, 1), 8.69 (d, J=3.7 Hz, 1H);

MS m/e 234 (MH$^+$).

3-Cyclopropyl-1H-quinazoline-2,4-dione

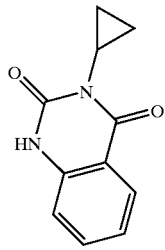

101

A solution of (2-cyclopropylcarbamoyl-phenyl)-carbamic acid methyl ester was dissolved in MeOH (100 ml) and treated with NaOMe (0.5 M, 5 ml, 2.5 mmol) and the mixture heated to reflux for 12 h. The mixture was cooled and filtered to give 4.05 g (53%) of 3-cyclopropyl-1H-quinazoline-2,4-dione as a white solid.

$^1$H NMR (DMSO-d$_6$) δ: 0.70–0.74 (m, 2 H), 0.98–1.02 (m, 2 H), 2.61–2.65 (m, 1 H), 7.11–7.18 (m, 2 H), 7.61 (t, J=7.5 Hz, 1 H), 7.89 (d, J=7.9 Hz, 1 H);

IR (KBr, cm$^{-1}$) 1727, 1666, 1163, 1082;

MS m/e 202 (MH$^+$);

Anal. Calcd for $C_{11}H_{10}N_2O_2 \cdot 0.4 H_2O$: C, 63.29; H, 5.18; N, 13.42. Found: C, 63.55; H, 5.44; N, 13.02.

[2-(3-Cyclopropyl-2,4-dioxo-3,4-dihydro-2H-quinazolin-1-ylmethyl)-1-(3-methyl-butyl)-1H-benzoimidazol-5-ylmethyl]-carbamic Acid tert-butyl Ester

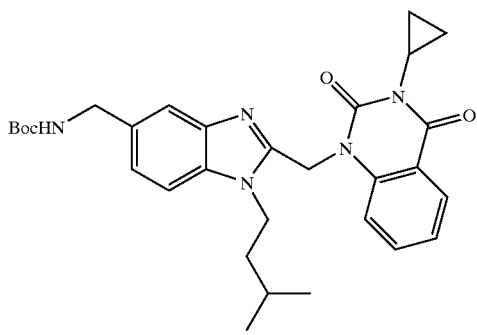

102

To a solution of the 3-cyclopropyl-1H-quinazoline-2,4-dione (148 mg, 0.73 mmol) in DMF (10 mL) was added BTPP (684 mg, 2.19 mmol). After stirring for 20 minutes, [2-chloromethyl-1-(3-methyl-butyl)-1H-benzoimidazol-5-ylmethyl]-carbamic acid tert-butyl ester; HCl salt (294 mg, 0.73 mmol) was added and the resulting mixture was stirred at room temperature overnight. The solvent was removed in vacuo and the residue precipitated from water. The title compound was collected by filtration and extensively washed with water and dried in vacuo to yield [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester as an off-white solid (310 mg, 80%):

$^1$H NMR (DMSO-d6) δ: 0.73–0.76 (m, 2H), 0.98 (d, J=6.5, 6H), 1.03–1.07 (m, 2H), 1.40 (s, 9H), 1.60–1.73 (m, 3H), 2.75–2.78 (m, 1H), 4.15 (d, J=6.0, 2H), 4.34 (t, J=7.8, 2H), 5.62 (s, 2H), 7.13 (d, J=8.2, 1H), 7.27 (t, J=7.7, 1H), 7.32 (s, 1H), 7.34 (br t, J=6.4, 1H), 7.47 (d, J=7.5, 1H), 7.48 (d, J=7.3, 1H), 7.67 (t, J=7.9), 8.06 (d, J=7.8, 1H);

MS m/e 532 (MH$^+$).

1-[5-Aminomethyl-1-(3-methyl-butyl)-1H-benzoimidazol-2-ylmethyl]-3-cyclopropyl-1H-quinazoline-2,4-dione; HCl Salt

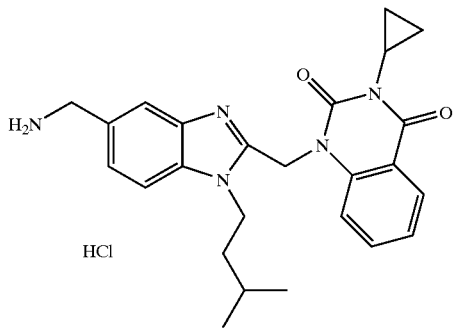

To a cooled (0° C.) solution of [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester (34 mg, 0.064 mmol) and anisole (70 µL, 0.64 mmol) in DCM (2 mL) was added TFA (148 µL, 1.92 mmol). The solution was allowed to reach room temperature and concentrated after 4 h. The residue was stripped with DCM (2×) and methanol (1×). The TFA salt was dissolved in methanol followed by the addition of acetyl cloride (46 µL, 0.64 mmol). After 10 min the solution was concentrated in vacuo and stripped with methanol (2×) and dichloromethane (2×) to give 1-[5-aminomethyl-1-(3-methyl-butyl)-1H-benzoimidazol-2-ylmethyl]-3-cyclopropyl-1H-quinazoline-2,4-dione; HCl salt (24 mg, 80%) as an off white solid.

$^1$H NMR (CD$_3$OD) δ: 0.85–0.87 (m, 2H), 1.08 (d, J=6.5, 6H), 1.14 (m, 2H), 1.83–1.93 (m, 3H), 2.82–2.85 (m, 1H), 4.32 (s, 2H), 4.63–4.66 (m, 2H), 5.96 (s, 2H), 7.39 (t, J=7.5, 1H), 7.43 (d, J=8.5, 1H), 7.74–7.76 (m, 2H), 7.83 (s, 1H), 8.01 (d, J=8.6, 1H), 8.26 (d, J=7.9, 1H);

MS m/e 432 (MH$^+$).

N-Cyclopropyl-2-nitro-benzenesulfonamide

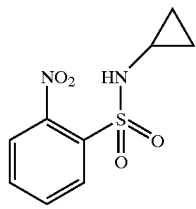

To a −78° C. mixture of cyclopropylamine (10 g, 1.75 mmol) in CH$_2$Cl$_2$ (100 mL) was added a solution of 2-nitrobenzene sulfonyl chloride (22.1 g, 85.7 mmol) and the mixture was stirred for 12 h. The mixture was washed with 1N HCl dried over MgSO$_4$ then concentrated to give 18.7 g, (88%) of a N-Cyclopropyl-2-nitro-benzenesulfonamide as a tan solid.

$^1$H NMR(CDCl$_3$) δ: 0.66–0.70 (m, 2H), 0.70–0.75 (m, 2H), 2.32–2.37 (m, 1H), 5.58 (s, 1H), 7.13–7.78 (m, 2H), 7.83–7.87 (m, 1H), 8.18–8.22 (m, 3H);

MS m/e 242 (MH$^+$).

2-Amino-N-cyclopropyl-benzenesulfonamide

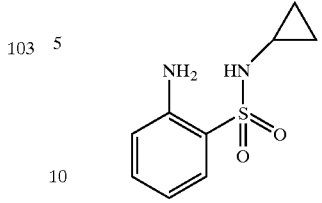

A solution of N-cyclopropyl-2-nitro-benzenesulfonamide (7.9 g, 33.0 mmol) in EtOH (50 ml) was treated with HCl (3.0 ml, 4.0 N in dioxane), Pd/C (10%, 100 mg) and shaken in a Parr Hydrogenator at 50 psi for 48 h. The catalyst was removed by filtration and the solvent evaporated to give 6.9 g (84%) of 2-Amino-N-cyclopropyl-benzenesulfonamide as a light grey solid.

$^1$H NMR (DMSO-d6) δ: 0.35–0.37 (m, 2H), 0.42–0.44 (m, 2H), 2.0–2.08 (m, 1H), 5.89 (s, 2H), 6.62 (t, J=7.1 Hz, 1H), 6.80 (d, J=8.3 Hz, 1H), 7.27 (t, J=7.1 Hz, 1H), 7.50 (d, j=8.0, 1H), 7.82 (s, 1H);

MS m/e 242 (MH$^+$).

2-cyclopropyl-1,1-dioxo-1,4-dihydro-2H-1λ$^6$-benzo[1,2,4]thiadiazin-3-one

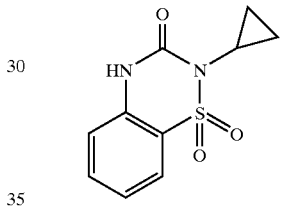

A solution of 2-amino-N-cyclopropyl-benzenesulfonamide (6.9 g, 32.5 mmol) in CH$_2$Cl$_2$ (50 ml) was treated with CDI (6.5 g, 40 mmol) and stirred for 12 h at reflux. The solution was a washed with HCl (1N), dried over MgSO$_4$ and concentrated to give 6.5 g (84%) of 2-cyclopropyl-1,1-dioxo-1,4-dihydro-2H-1λ$^6$-benzo[1,2,4]thiadiazin-3-one as a brown solid.

$^1$H NMR (DMSO-d6) δ: 0.72–0.80 (m, 2H), 0.90–1.1 (m, 2H), 2.71–2.75 (m, 1H), 7.23 (d. 8.1 Hz, 1H), 7.29 (t, J=7.7 Hz, 1H), 7.68 (t, J=7.5 Hz, 1H), 7.81 (d, J=7.6 Hz, 1H);

MS m/e 238 (MH$^+$).

[2-(2-Cyclopropyl-1,1,3-trioxo-2,3-dihydro-1H-1λ$^6$-benzo[1,2,4]thiadiazin-4-ylmethyl)-1-(3-methyl-butyl)-1H-benzoimidazol-5-ylmethyl]-carbamic Acid tert-butyl Ester

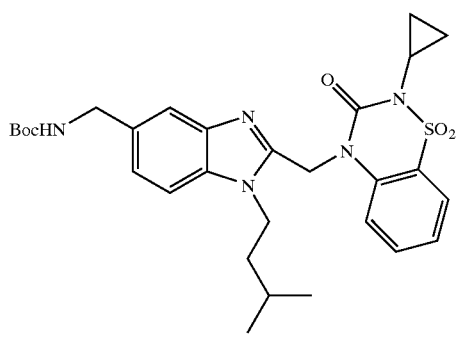

[2-(2-Cyclopropyl-1,1,3-trioxo-2,3-dihydro-1H-1λ$^6$-benzo[1,2,4]thiadiazin-4-ylmethyl)-1-(3-methyl-butyl)-1H- benzoimidazol-5-ylmethyl]-carbamic acid tert-butyl ester was prepared following the same procedure as [2-[3-(2-fluoro-ethoxyimino)-2-oxo-2,3-dihydro-pyrrolo[2,3-b]pyridin-1-ylmethyl]-1-(3-methyl-butyl)-1H-benzoimidazol-5-ylmethyl]-carbamic acid tert-butyl ester, using 2-cyclopropyl-1,1-dioxo-1,4-dihydro-2H-1λ⁶-benzo[1,2,4]thiadiazin-3-one (26 mg, 0.11 mmol) and [2-chloromethyl-1-(3-methyl-butyl)-1H-benzoimidazol-5-ylmethyl]-carbamic acid tert-butyl ester; HCl salt (40 mg, 0.11 mmol). Purification was accomplished by flash chromatography (eluent hexanes-ethyl acetate (1:1), followed by trituration from diisopropyl ether to [2-(2-cyclopropyl-1,1,3-trioxo-2,3-dihydro-1H-1λ⁶-benzo[1,2,4]thiadiazin-4-ylmethyl)-1-(3-methyl-butyl)-1H-benzoimidazol-5-ylmethyl]-carbamic acid tert-butyl ester (34 mg, 55% yield) as a white solid.

¹H NMR (CDCl₃) δ: 0.86–0.90 (m, 2H), 1.02 (d, J=6.5 Hz, 6H), 1.05–1.09 (m, 2H), 1.45 (s, 9H), 1.69–1.74 (m, 3H), 2.88–2.95 (m, 1H), 4.21–4.24 (m, 2H), 4.40 (d, J=5.2 Hz, 2H), 4.86 (br s, 1H), 5.51 (s, 2H), 7.22 (d, J=8.2 Hz, 1H), 7.27–7.29 (m, 2H), 7.60–7.64 (m, 2H), 7.83 (d, J=7.8 Hz, 1H), 7.86 (d, J=8.5 Hz, 1H);

MS m/e 568 (MH⁺).

4-[5-Aminomethyl-1-(3-methyl-butyl)-1H-benzoimidazol-2-ylmethyl]-2-cyclopropyl-1,1-dioxo-1,4-dihydro-2H-1λ⁶-benzo[1,2,4]thiadiazin-3-one; HCl Salt

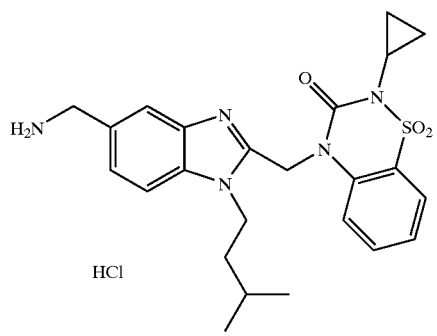

108

To a cooled (0° C.) solution of [2-(2-cyclopropyl-1,1,3-trioxo-2,3-dihydro-1H-1λ⁶-benzo[1,2,4]thiadiazin-4-ylmethyl)-1-(3-methyl-butyl)-1H-benzoimidazol-5-ylmethyl]-carbamic acid tert-butyl ester (21 mg, 0.036 mmol) and anisole (39 µL, 0.36 mmol) in DCM (0.5 mL) was added 4N HCl in dioxane (90 µL, 0.36 mmol). After 30 min. the solution was allowed to reach room temperature. After 3 h. the volatiles were removed in vacuo, stripped with methanol (3 times), and the residue was triturated in diethyl ether. 4-[5-Aminomethyl-1-(3-methyl-butyl)-1H-benzoimidazol-2-ylmethyl]-2-cyclopropyl-1,1-dioxo-1,4-dihydro-2H-1λ⁶-benzo[1,2,4]thiadiazin-3-one; HCl salt (12 mg, 92%) was collected by filtration as a white solid:

¹H NMR (DMSO-d6) δ: 0.83 (br s, 2H), 1.00 (m, 8H), 1.45 (s, 9H), 1.75 (br s, 3H), 2.84–2.85 (m, 1H), 4.15 (d, J=5.1 Hz, 2H), 4.45 (br s, 2H), 5.77 (s, 2H), 7.47 (t, J=7.5 Hz, 1H), 7.58 (br m, 1H), 7.63 (d, J=8.2 Hz, 1H), 7.79 (t, J=7.8 Hz, 1H), 7.83 (br m, 2H), 7.98 (d, J=7.7 Hz, 1H), 8.50 (br s, 3H);

MS m/e 468 (MH⁺).

[2-(3-Cyclopropyl-2,4-dioxo-3,4-dihydro-2H-quinazolin-1-ylmethyl)-1-(3-methyl-butyl)-1H-benzoimidazol-5-ylmethyl]-methyl-carbamic Acid tert-butyl Ester

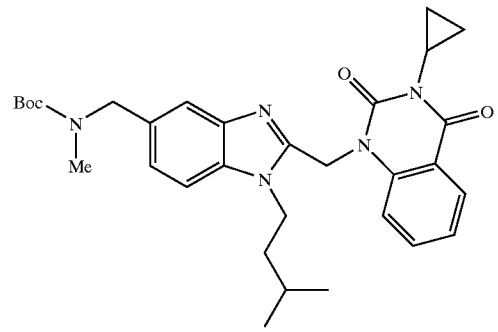

109

To a suspension of NaH (60% mineral oil, 11.2 mg, 0.28 mmol) in DMF (2 mL) at room temperature was added [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester (50 mg, 0.094 mmol). After stirring for 5 min iodomethane (47 µL, 0.75 mmol) was added. The mixture was stirred overnight under a nitrogen atmosphere and partitioned between water and ethyl acetate. The aqueous phase was extracted with ethyl acetate and the combined organic phases washed with 5% sodium meta-bisulfite and brine. After drying over MgSO₄ the residue was purified by flash chromatography (eluent 2% MeOH in CH₂Cl₂) to give [2-(3-cyclopropyl-2,4-dioxo-3,4-dihydro-2H-quinazolin-1-ylmethyl)-1-(3-methyl-butyl)-1H-benzoimidazol-5-ylmethyl]-methyl-carbamic acid tert-butyl ester (39 mg, 76%) as a white solid:

¹H NMR (CD₃OD) δ 0.85–0.88 (m, 2H), 1.06 (d, J=6.2 Hz, 6H), 1.11–1.14 (m, 2H), 1.45 (s, 9H), 1.75–1.78 (m, 3H), 2.77 (s, 3H), 2.79–2.83 (m, 1H), 4.40 (t, J=7.6 Hz, 2H), 4.49 (s, 2H), 5.69 (s, 2H), 7.21 (d, J=8.3 Hz, 1H), 7.25–7.28 (m, 2H), 7.36 (s, 1H), 7.50 (d, J=8.4 Hz, 1H), 7.61 (t, J=7.8 Hz, 1H), 8.16 (d, J=8.1 Hz, 1H);

MS m/e 546 (MH⁺).

3-Cyclopropyl-1-[5-methylaminomethyl-1-(3-methyl-butyl)-1H-benzoimidazol-2-ylmethyl]-1H-quinazoline-2,4-dione; HCl Salt

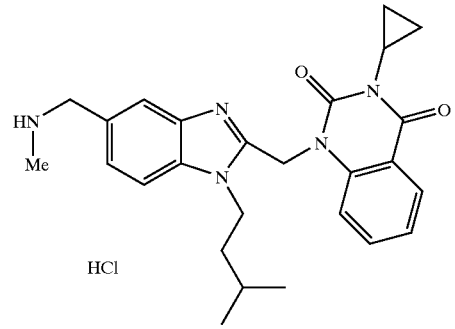

110

To a cooled (0° C.) solution of [2-(3-cyclopropyl-2,4-dioxo-3,4-dihydro-2H-quinazolin-1-ylmethyl)-1-(3-methyl-butyl)-1H-benzoimidazol-5-ylmethyl]-methyl-carbamic acid tert-butyl ester (39 mg, 0.071 mmol) and anisole (77 µL, 0.71 mmol) in DCM (3 mL) was added TFA (165 µL, 2.14 mmol). The solution was allowed to reach room temperature and after 1 h another amount of TFA (200 µL) was added. After 1 h the volatiles were removed in vacuo and the residue was stripped with DCM (2×) and methanol (1×). The TFA salt was dissolved in methanol followed by the addition of acetyl cloride (50 μL, 0.71 mmol) and concentrated. This procedure was repeated once. The product was triturated in diethyl ether to give 3-cyclopropyl-1-[5-methylaminomethyl-1-(3-methyl-butyl)-1H-benzoimidazol-2-ylmethyl]-1H-quinazoline-2,4-dione; HCl salt (31 mg, 91%) as an off white solid.

$^1$H NMR (DMSO-d6) δ: 0.78 (m, 2H), 1.01 (d, J=6.0, 6H), 1.03–1.06 (m, 2H), 1.74 (br m, 3H), 2.47 (s, 3H), 2.74–2.78 (m, 1H), 4.21 (br s, 1H), 4.49 (br s, 2H), 5.80 (br s, 2H), 7.31 (t, J=7.5, 1H), 7.48 (d, J=8.5, 1H), 7.57–7.61 (br m, 1H), 7.70 (t, J=8.4, 1H), 7.85 (br m, 2H), 8.09 (d, J=7.9, 1H), 9.33 (br s, 2H);

MS m/e 446 (MH$^+$).

4-(4-Cyano-2-nitro-phenylamino)-butan-1-ol

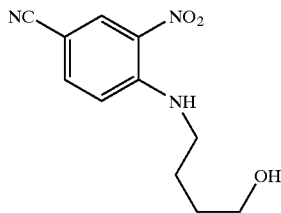

111

A mixture of 3-nitro-4-chloro-benzonitrile (20.4 g, 112.2 mmol), and 4-aminobutanol (10 g, 112 mmol) and K$_2$CO$_3$ (30.9 g, 224 mmol) in CH$_3$CN (100 ml) was stirred at 23° C. for 12 h. Starting material remains by TLC analysis. Additional 4-aminobutanol (2 g, 22 mmol) was added and stirring continued for 24 h. The mixture is filtered and concentrated. The residue is dissolved in EtOAc and washed with water. The extracts are dried over MgSO$_4$ and concentrated to give 26 g (99%) of 4-(4-cyano-2-nitro-phenylamino)-butan-1-ol as an orange solid.

$^1$H NMR (CDCl$_3$) δ: 1.62–1.75 (m, 2H), 1.84–1.90 (m, 2H), 3.40–3.44 (m, 2H), 3.74 (t, J=6.1 Hz, 2H), 6.92 (d, J=9.0 Hz, 1H), 7.59 (d, J=9.0 Hz, 1H), 8.45 (br s, 1H), 8.50 (s, 1H);

MS m/e 235 (MH$^+$).

2,2-Dimethyl-propionic Acid 4-(4-cyano-2-nitro-phenylamino)-butyl Ester

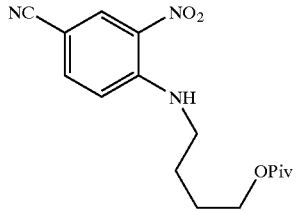

112

A solution of 4-(4-hydroxy-butylamino)-3-nitro-benzonitrile (10.0 g, 42.5 mmol) in pyridine (100 mL) was cooled to 0° C. under nitrogen. Pivaloyl chloride (5.8 mL, 47 mmol) was dropwise added and the resulting solution allowed to warm to room temperature and stirred overnight. The solvent was removed in vacuo and the residue stripped with toluene. The residue was suspended in ethyl acetate, filtered, and the filtrated concentrated to give 2,2-dimethyl-propionic acid 4-(4-cyano-2-nitro-phenylamino)-butyl ester (13.3 g, 98%) as a yellow solid.

$^1$H NMR (DMSO-d6) δ: 1.12 (s, 9H), 1.65 (m, 4H), 3.46–3.47 (br m, 2H), 4.05 (br s, 2H), 7.19 (d, J=9.2 Hz, 1H), 7.81 (d, J=9.2 Hz, 1H), 8.50 (s, 1H), 8.63 (br t, J=5.8 Hz, 1H);

MS m/e 320 (MH$^+$).

2,2-Dimethyl-propionic Acid 4-(2-amino-4-cyano-phenylamino)-butyl Ester

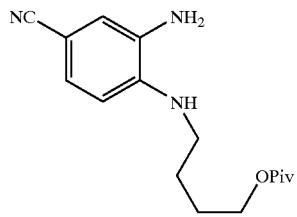

113

A mixture of 2,2-dimethyl-propionic acid 4-(4-cyano-2-nitro-phenylamino)-butyl ester (13.3 g, 41.6 mmol) and 10% Pd/C (500 mg) in THF (40 mL) and MeOH (50 mL) was rocked under a hydrogen atmosphere (42 psi) for 1.5 h. The catalyst was removed by filtration, washed with ethyl acetate, and the filtrate concentrated in vacuo to yield the title compound (11.9 g, 99%) as a black solid.

$^1$H NMR (DMSO-d6) δ: 1.13 (s, 9H), 1.62–1.69 (m, 4H), 3.11–3.15 (m, 2H), 4.05 (t, J=5.9 Hz, 1H), 4.97 (br s, 2H), 5.37 (br t, 1H), 6.45 (d, J=8.2 Hz, 1H), 6.76 (s, 1H), 6.90 (d, J=8.2 Hz, 1H);

MS m/e 290 (MH$^+$).

2,2-Dimethyl-propionic Acid 4-(2-benzyloxymethyl-5-cyano-benzoimidazol-1-yl)-butyl Ester

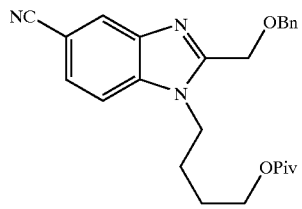

114

A solution of 2,2-dimethyl-propionic acid 4-(2-amino-4-cyano-phenylamino)-butyl ester (11.8 g, 40.8 mmol) and triethyl amine (6.8 mL, 49 mmol) in DCM (125 mL) was cooled to 0° C. under nitrogen. Acetyl chloride (7.1 mL, 45 mmol) was dropwise added and the resulting solution allowed to warm to room temperature and stirred overnight. The solution was quenched with water (100 mL), the layers separated, and the aqueous phase extracted with DCM (50 mL). The combined organic phases were washed with brine and dried (MgSO$_4$). The resulting oil was heated at reflux temperature in acetic acid (125 mL) for 45 min. The mixture was concentrated in vacuo and partitioned between satd. NaHCO$_3$ and ethyl acetate. The aqueous phase was extracted with ethyl acetate, and the combined organic phases washed with brine and dried (MgSO$_4$). The resulting oil was purified by flash chromatography (eluent hexane-ethyl acetate 2:1, 3:2) to give the title compound (14.3 g, 84%) as a grey solid.

$^1$H NMR (DMSO-d6) δ: 1.09 (s, 9H), 1.55–1.61 (m, 2H), 1.75–1.81 (m, 2H), 3.96 (t, J=6.3 Hz, 1H), 4.34 (t, J=7.5 Hz, 2H), 4.60 (s, 2H), 4.83 (s, 2H), 7.30–7.33 (m, 1H), 7.36 (m, 4H), 7.67 (d, J=8.3 Hz, 1H), 7.83 (d, J=8.3 Hz, 1H), 8.20 (s, 1H);

MS m/e 420 (MH$^+$).

2,2-Dimethyl-propionic Acid 4-(5-aminomethyl-2-hydroxymethyl-benzoimidazol-1-yl)-butyl Ester; HCl Salt

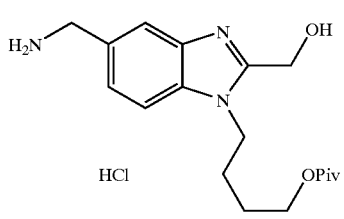

115

To a solution of 2,2-dimethyl-propionic acid 4-(2-benzyloxymethyl-5-cyano-benzoimidazol-1-yl)-butyl ester (2.0 g, 4.8 mmol) in THF (30 mL), methanol (60 mL) and concentrated HCl (1.8 mL) was added 10% Pd/C (200 mg). This mixture was rocked under a hydrogen atmosphere (47 psi) for 18 hrs. The catalyst was removed by filtration and the solution concentrated in vacuo to give the title compound as a tan solid. This procedure was repeated with another batch using identical quantities, and the two batches combined, which was used in the next step without purification:

$^1$H NMR (DMSO-d6) δ: 1.13 (s, 9H), 1.65–1.71 (m, 2H), 1.84–1.90 (m, 2H), 4.05 (t, J=6.2 Hz, 1H), 4.22 (br q, J=5.6 Hz, 2H), 4.45 (t, J=7.3 Hz, 2H), 5.04 (s, 2H), 7.70 (d, J=8.7 Hz, 1H), 7.97 (s, 1H), 8.01 (d, J=8.7 Hz, 1H), 8.57 (br s, 3H);

MS m/e 334 (MH$^+$).

2,2-Dimethyl-propionic Acid 4-[5-(tert-butoxycarbonylamino-methyl)-2-hydroxymethyl-benzoimidazol-1-yl]-butyl Ester

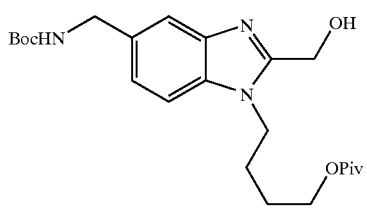

116

To a cooled (0° C.) solution of the crude 2,2-dimethyl-propionic acid 4-(5-aminomethyl-2-hydroxymethyl-benzoimidazol-1-yl)-butyl ester; HCl salt (9.6 mmol) and DIPEA (3.7 mL, 21 mmol) in DMF (40 mL) was added Boc$_2$O (2.1 g, 9.6 mmol) in one portion. After stirring at the same temperature for 30 min. the volatiles were removed in vacuo. Water was added to the residue and the product extracted into ethyl acetate (2x). The combined organic extracts were washed with water, brine and dried over MgSO$_4$ and concentrated. The title compound was obtained by trituration from Et$_2$O. The mother liquor was purified by flash column chromatography (eluent 3%, 5% MeOH in CH$_2$Cl$_2$) to give a second crop of the title compound. Combined yield: 3.08 g, 74% (2 steps) as an off-white solid.

$^1$H NMR (DMSO$^{d6}$) δ 1.11 (s, 9H), 1.40 (s, 9H), 1.59–1.64 (m, 2H), 1.79–1.85 (m, 2H), 4.03 (t, J=6.1, 1 H), 4.20 (d, J=6.4 Hz, 2H), 4.29 (t, J=7.3 Hz, 2H), 4.69 (d, J=5.8 Hz, 2H), 5.58 (t, J=5.8 Hz, 2H), 7.12 (d, J=8.1 Hz, 1H), 7.38 (br t, J=5.8 Hz, 1H), 7.43 (s, 1H), 7.47 (d, J=8.1 Hz, 1H);

MS m/e 434 (MH$^+$).

2,2-Dimethyl-propionic Acid 4-[5-(tert-butoxycarbonylamino-methyl)-2-chloromethyl-benzoimidazol-1-yl]-butyl Ester; HCl Salt

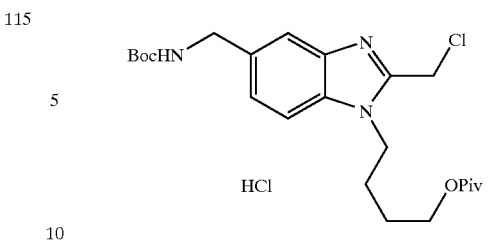

117

To a cooled (0° C.) solution of 2,2-dimethyl-propionic acid 4-[5-(tert-butoxycarbonylamino-methyl)-2-hydroxymethyl-benzoimidazol-1-yl]-butyl ester (3.08 g, 7.10 mmol) in DCM (20 mL) was added thionyl chloride (0.78 mL, 10.7 mmol). The solution was stirred at 0° C. for 15 min. and concentrated in vacuo to give the title compound (3.43 g, 99%) as a white solid, which was used without further purification.

$^1$H NMR (DMSO-d6) δ: 1.11 (s, 9H), 1.40 (s, 9H), 1.66–1.72 (m, 2H), 1.85–1.91 (m, 2H), 4.06 (t, J=6.1, 1H), 4.26 (d, J=5.5, 2H), 4.46 (t, J=7.3, 2H), 5.26 (s, 2H), 7.39 (d, J=8.5, 1H), 7.52 (br t, J=5.5, 1H), 7.60 (s, 1H), 7.81 (d, J=8.5, 1H);

MS m/e 452 (MH$^+$).

2,2-Dimethyl-propionic Acid 4-[5-(tert-butoxycarbonylamino-methyl)-2-(3-cyclopropyl-2,4-dioxo-3,4-dihydro-2H-quinazolin-1-ylmethyl)-benzoimidazol-1-yl]-butyl Ester

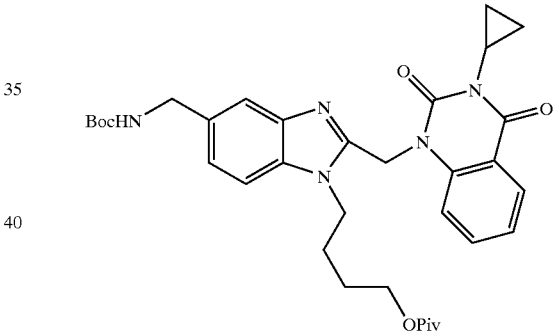

118

The procedure for [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed using 3-cyclopropyl-1H-quinazoline-2,4-dione (44 mg, 0.22 mmol) and 2,2-dimethyl-propionic acid 4-[5-(tert-butoxycarbonylamino-methyl)-2-chloromethyl-benzoimidazol-1-yl]-butyl ester; HCl salt (107 mg, 0.219 mmol) to give 2,2-Dimethyl-propionic acid 4-[5-(tert-butoxycarbonylamino-methyl)-2-(3-cyclopropyl-2,4-dioxo-3,4-dihydro-2H-quinazolin-1-ylmethyl)-benzoimidazol-1-yl]-butyl ester (110 mg, 81%) as a white solid:

$^1$H NMR (CD$_3$OD) δ: 0.85–0.88 (m, 2H), 1.11–1.15 (m, 2H), 1.16 (s, 9H), 1.41 (s, 9H), 1.76–1.82 (m, 2H), 1.92–2.02 (m, 2H), 2.80–2.84 (m, 1H), 4.15 (t, J=6.1 Hz, 1H), 4.28 (s, 2H), 4.44 (t, J=7.3 Hz, 2H), 5.68 (s, 2H), 7.23–7.29 (m, 3H), 7.39 (s, 1H), 7.50 (d, J=8.9 Hz, 1H), 7.61 (t, J=8.5 Hz, 1H), 8.17 (d, J=8.2 Hz, 1H);

MS m/e 618 (MH$^+$).

[2-(3-Cyclopropyl-2,4-dioxo-3,4-dihydro-2H-quinazolin-1-ylmethyl)-1-(4-hydroxy-butyl)-1H-benzoimidazol-5-ylmethyl]-carbamic Acid tert-butyl Ester

119

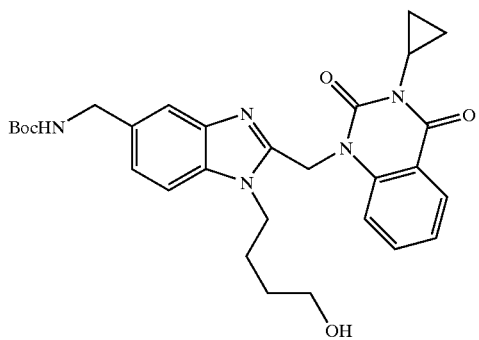

To a solution of 2,2-dimethyl-propionic acid 4-[5-(tert-butoxycarbonylamino-methyl)-2-(3-cyclopropyl-2,4-dioxo-3,4-dihydro-2H-quinazolin-1-ylmethyl)-benzoimidazol-1-yl]-butyl ester (110 mg, 0.178 mmol) in methanol (5 mL) and water (1.5 mL) was added 1M NaOH (356 µL, 0.356 mmol). The resulting mixture was heated at 70–80° C. for 2 hrs. The solution was neutralized with 1M HCl, methanol was removed in vacuo and the aqueous residue extracted with ethyl acetate (3×10 mL). The combined organic layers were washed with brine and dried (MgSO$_4$). Purification by flash chromatography (eluent 2%, 5% methanol in DCM) afforded [2-(3-Cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester (60 mg, 63%) as a white solid.

$^1$H NMR (DMSO-d6) δ: 0.73–0.76 (m, 2H), 1.03–1.07 (m, 2H), 1.37 (s, 9H), 1.48–1.53 (m, 2H), 1.77–1.82 (m, 2H), 2.76–2.78 (m, 1H), 3.44 (d, J=4.2 Hz, 2H), 4.15 (d, J=6.0 Hz, 2H), 4.36 (t, J=7.3 Hz, 2H), 4.50 (br s, 1H), 5.61 (s, 2H), 7.12 (d, J=7.9 Hz, 1H), 7.27 (t, J=7.5 Hz, 1H), 7.31 (s, 1H), 7.33 (br t, J=6.1 Hz, 1H), 7.46 (d, J=8.5 Hz, 1H), 7.51 (d, J=8.4 Hz, 1H), 7.66 (t, J=7.9 Hz, 1H), 8.06 (d, J=7.9 Hz, 1H);

MS m/e 534 (MH$^+$).

1-[5-Aminomethyl-1-(4-hydroxy-butyl)-1H-benzoimidazol-2-ylmethyl]-3-cyclopropyl-1H-quinazoline-2,4-dione; HCl Salt

120

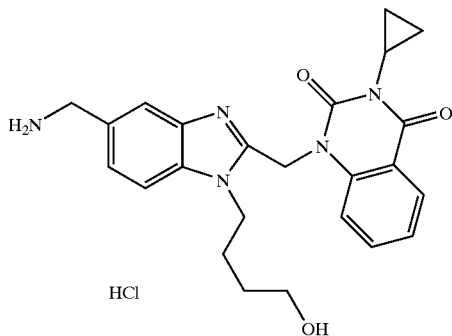

To a suspension of [2-(3-cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester (56 mg, 0.11 mmol) and anisole (57 µL, 0.53 mmol) in DCM (3 mL) was added TFA (162 µL, 2.10 mmol). The solution was allowed stirred for 11 hrs. and another portion of TFA (1 mL) was added. After stirring overnight the volatiles were removed in vacuo and the residue was stripped with DCM (2×). The resulting trifluoroacetate was dissolved in methanol followed by the addition of acetyl cloride (100 µL, 1.42 mmol) and concentrated after 1 h. The product was triturated in diethyl ether to give the title compound (50 mg, 100%) as an off white solid.

$^1$H NMR (CD$_3$OD) δ 0.85–0.88 (m, 2H), 1.11–1.15 (m, 2H), 1.71–1.77 (m, 2H), 2.12–2.18 (m, 2H), 2.82–2.86 (m, 1H), 3.68 (t, J=6.1 Hz, 1H), 4.33 (s, 2H), 4.72 (t, J=7.7 Hz, 2H), 6.02 (s, 2H), 7.39 (t, J=7.9 Hz, 1H), 7.44 (d, J=8.2 Hz, 1H), 7.74–7.78 (m, 2H), 7.87 (s, 1H), 8.11 (d, J=8.5 Hz, 1H), 8.26 (d, J=8.2 Hz, 1H);

MS m/e 434 (MH$^+$).

[2-(3-Cyclopropyl-2,4-dioxo-3,4-dihydro-2H-quinazolin-1-ylmethyl)-1-(4-fluoro-butyl)-1H-benzoimidazol-5-ylmethyl]-carbamic Acid tert-butyl Ester

121

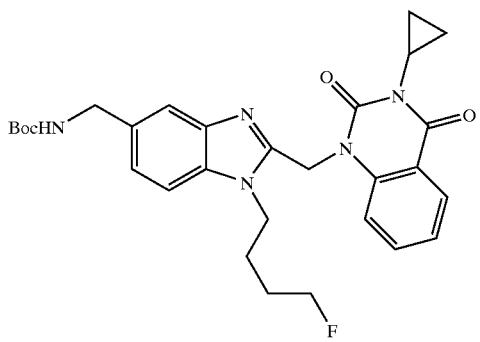

To a cooled (−78° C.) suspension of [2-(3-cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester (90 mg, 0.17 mmol) in DCM (4 mL) was added DAST (44 µL, 0.34 mmol) under nitrogen. The mixture was allowed to reach room temperature over 2 hrs. The solution was quenched with satd. NaHCO$_3$ (5 mL) and extracted with DCM (2×15 mL). The combined organic phases were washed with brine and dried (Na$_2$SO$_4$). Purification by flash chromatography (eluent 2% methanol in DCM) afforded the title compound (69 mg, 77%) as a white solid.

$^1$H NMR (DMSO-d6) δ: 0.73–0.76 (m, 2H), 1.03–1.07 (m, 2H), 1.37 (s, 9H), 1.70–1.80 (m, 2H), 1.84–1.90 (m, 2H), 2.74–2.79 (m, 1H), 4.15 (d, J=5.8 Hz, 2H), 4.39 (t, J=7.0 Hz, 2H), 4.50 (dt, J=6.0 Hz 48, 2H), 5.61 (s, 2H), 7.13 (d, J=7.9 Hz, 1H), 7.27 (t, J=7.6 Hz, 1H), 7.32 (s, 1H), 7.33 (br t, J=5.2 Hz, 1H), 7.49 (d, J=8.9 Hz, 1H), 7.53 (d, J=8.6 Hz, 1H), 7.66 (t, J=7.6 Hz, 1H), 8.06 (d, J=7.9 Hz, 1H);

MS m/e 536 (MH$^+$).

1-[5-Aminomethyl-1-(4-fluoro-butyl)-1H-benzoimidazol-2-ylmethyl]-3-cyclopropyl-1H-quinazoline-2,4-dione; HCl Salt

122

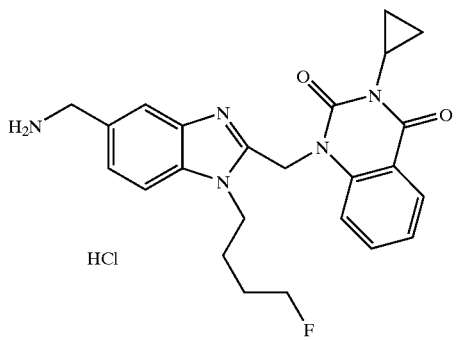

To a cooled (0° C.) solution of [2-(3-cyclopropyl-2,4-dioxo-3,4-dihydro-2H-quinazolin-1-ylmethyl)-1-(4-fluorobutyl)-1H-benzoimidazol-5-ylmethyl]-carbamic acid tert-butyl ester (67 mg, 0.13 mmol) in DCM (3 mL) was added TFA (289 μL, 3.75 mmol). The solution was allowed to reach room temperature and stirred overnight. The volatiles were removed in vacuo and the residue was stripped with DCM. The TFA salt was dissolved in methanol followed by the addition of acetyl cloride (89 μL, 1.3 mmol) and concentrated. The product was stripped with methanol and DCM (twice) to give the title compound (64 mg, 100%) as a white solid.

$^1$H NMR (DMSO-d6) δ: 0.76–0.79 (m, 2H), 1.03–1.07 (m, 2H), 1.75–1.85 (m, 2H), 1.93–1.97 (m, 2H), 2.74–2.78 (m, 1H), 4.13 (d, J=5.3 Hz, 2H), 4.47–4.59 (m, 4H), 5.80 (s, 2H), 7.31 (t, J=7.5 Hz, 1H), 7.46 (d, J=8.5 Hz, 1H), 7.54 (br d, J=7.2, 1H), 7.69 (t, J=7.4 Hz, 1H), 7.76 (s, 1H), 7.88 (br s, 1H), 8.09 (d, J=7.8 Hz, 1H), 8.40 (br s, 3H);

MS m/e 436 (MH$^+$).

3-Bromo-1H-indazole

123

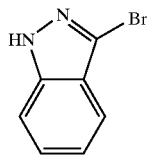

3-Bromo-1H-indazole was prepared as described (Boulton B. E. and Coller, A. W., *Aust. J. Chem.*, 1974, 27, 2343).

4-Methoxy-1H-quinolin-2-one

124

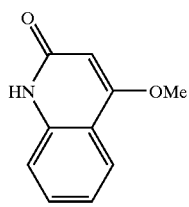

To a suspension of 2,4-dihydroxy quinoline (3.00 g, 18.6 mmol) and potassium carbonate (5.14 g, 37.2 mmol) in acetone (500 mL) was added dimethyl sulfate (2.1 mL, 22 mmol) and the resulting mixture heated at reflux during 5 hrs. The solvent was removed in vacuo and the residue triturated in water. The product was collected by filtration, washed with water and triturated from methanol to give 4-methoxy 2-quinolone (1.76 g, 54%) as a white solid, that had identical $^1$H NMR data as reported (Reisch et al., *Arch. Pharm.*, 1980, 313, 751–755).

3-(2,2,2-Trifluoro-ethyl)-1H-quinazoline-2,4-dione

125

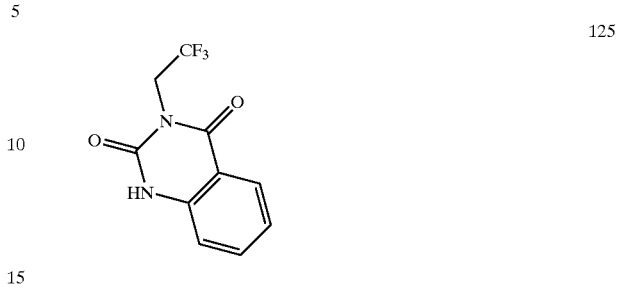

3-(2,2,2-Trifluoro-ethyl)-1H-quinazoline-2,4-dione was prepared using the same procedure as described for the preparation of 3-Cyclopropyl-1H-quinazoline-2,4-dione starting with 2,2,2-trifluoroethylamine hydrochloride:

$^1$H NMR (DMSO-d$_6$) δ: 4.72 (q, J=9.2 Hz, 2H), 7.20–7.26 (m, 2H), 7.08 (t, J=7.6 Hz, 1H), 7.96 (d, J=7.6 Hz, 1H);

IR (KBr, cm$^{-1}$) 1727, 1666, 1163, 1082;

MS m/e 244 (MH$^+$);

Anal. Calcd for $C_{10}H_7F_3N_2O_2$: C, 49.19; H, 2.89; N, 11.47.

Found: C, 49.04; H, 2.85; N, 11.42.

2,2-Dimethyl-propionic Acid 4-{5-(tert-butoxycarbonylamino-methyl)-2-[2,4-dioxo-3-(2,2,2-trifluoro-ethyl)-3,4-dihydro-2H-quinazolin-1-ylmethyl]-benzoimidazol-1-yl}-butyl Ester

126

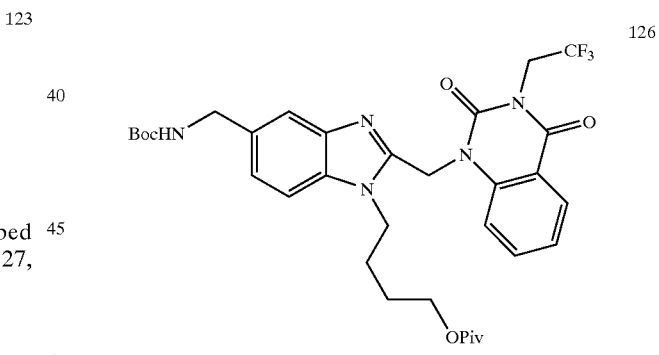

The procedure for [2-(3-Cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed using 3-(2,2,2-trifluoro-ethyl)-1H-quinazoline-2,4-dione (150 mg, 0.614 mmol) and 2,2-dimethyl-propionic acid 4-[5-(tert-butoxycarbonylamino-methyl)-2-chloromethyl-benzoimidazol-1-yl]-butyl ester; HCl salt (300 mg, 0.614 mmol). 2,2-Dimethyl-propionic acid 4-{5-(tert-butoxycarbonylamino-methyl)-2-[2,4-dioxo-3-(2,2,2-trifluoro-ethyl)-3,4-dihydro-2H-quinazolin-1-ylmethyl]-benzoimidazol-1-yl}-butyl ester was air-dried and used without further purification:

[2-[2,4-Dioxo-3-(2,2,2-trifluoro-ethyl)-3,4-dihydro-2H-quinazolin-1-ylmethyl]-1-(4-hydroxy-butyl)-1H-benzoimidazol-5-ylmethyl]-carbamic Acid tert-butyl Ester

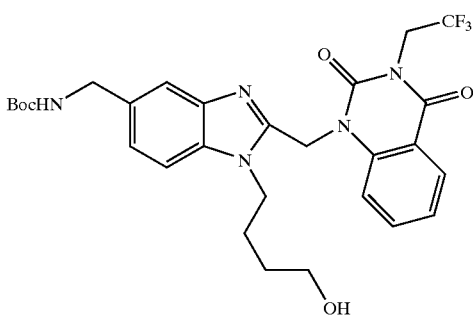

127

The procedure for the preparation of [2-(3-Cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester was followed starting from crude 2,2-dimethyl-propionic acid 4-{5-(tert-butoxycarbonylamino-methyl)-2-[2,4-dioxo-3-(2,2,2-trifluoro-ethyl)-3,4-dihydro-2H-quinazolin-1-ylmethyl]-benzoimidazol-1-yl}-butyl ester (0.614 mmol). Purification by flash chromatography (eluent 2%, 4% methanol in DCM) afforded the title compound (150 mg, 42% over two steps) as a white solid:

$^1$H NMR (DMSO-d$_6$) δ: 1.36 (s, 9H), 1.48–1.54 (m, 2H), 1.80–1.86 (m, 2H), 3.45 (q, J=5.3 Hz, 2H), 4.15 (d, J=5.8 Hz, 2H), 4.36 (t, J=6.7 Hz, 2H), 4.50 (t, J=5.3 Hz, 2H), 4.85 (q, J=9.5 Hz, 2H), 5.68 (s, 2H), 7.31 (s, 1H), 7.33 (br t, 1H), 7.36 (t, J=7.9 Hz, 1H), 7.51–7.54 (m, 2H), 7.76 (t, J=8.5 Hz, 1H), 8.14 (d, J=7.9 Hz, 1H);

MS m/e 576 (MH$^+$).

1-[5-Aminomethyl-1-(4-hydroxy-butyl)-1H-benzoimidazol-2-ylmethyl]-3-(2,2,2-trifluoro-ethyl)-1H-quinazoline-2,4-dione; HCl Salt

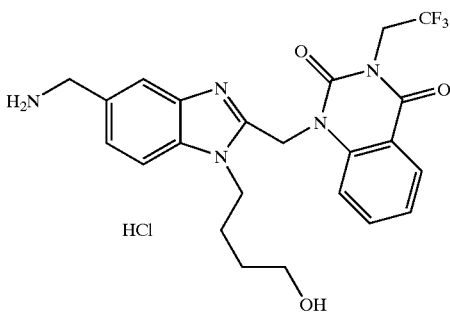

128

To a suspension of [2-[2,4-dioxo-3-(2,2,2-trifluoro-ethyl)-3,4-dihydro-2H-quinazolin-1-ylmethyl]-1-(4-hydroxy-butyl)-1H-benzoimidazol-5-ylmethyl]-carbamic acid tert-butyl ester (80 mg, 0.14 mmol) in dichloromethane (3 mL) was added TFA (319 µL, 4.14 mmol). The solution was allowed to stir for 6 hrs. followed by the removal of the volatiles in vacuo. The resulting trifluoroacetate was dissolved in methanol (3 mL) followed by the addition of acetyl cloride (98 µL, 1.4 mmol) and concentrated after 10 min. This procedure was repeated once allowing the reaction to run for 3 hrs. The solution was concentrated in vacuo and the residue stripped with DCM (thrice). The product was triturated in diethyl ether and the ether decanted to yield 1-[5-Aminomethyl-1-(4-hydroxy-butyl)-1H-benzoimidazol-2-ylmethyl]-3-(2,2,2-trifluoro-ethyl)-1H-quinazoline-2,4-dione; HCl salt (79 mg, 100%) as a white solid:

$^1$H NMR (DMSO-d6) δ: 1.51–1.56 (m, 2H), 1.88–1.93 (m, 2H), 3.47 (t, J=6.4 Hz, 2H), 4.12 (d, J=5.2 Hz, 2H), 4.52 (br t, J=6.4 Hz, 2H), 4.84 (q, J=9.2 Hz, 2H), 5.87 (s, 2H), 7.39 (t, J=7.6 Hz, 1H), 7.53 (2×d, J=8.2, 2H), 7.75 (s, 1H), 7.78 (t, J=6.7 Hz, 1H), 8.86 (br d, J=7.9 Hz, 1H), 8.17 (d, J=7.9 Hz, 1H), 8.41 (br s, 3H);

MS m/e 476 (MH$^+$).

2,2-Dimethyl-propionic Acid 4-{5-aminomethyl-2-[2,4-dioxo-3-(2,2,2-trifluoro-ethyl)-3,4-dihydro-2H-quinazolin-1-ylmethyl]-benzoimidazol-1-yl}-butyl Ester; HCl Salt

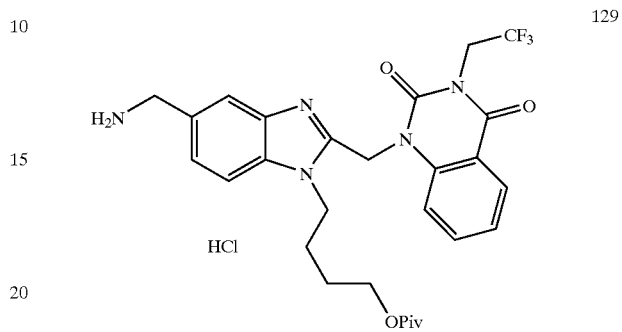

129

A solution of 2,2-dimethyl-propionic acid 4-{5-(tert-butoxycarbonylamino-methyl)-2-[2,4-dioxo-3-(2,2,2-trifluoro-ethyl)-3,4-dihydro-2H-quinazolin-1-ylmethyl]-benzoimidazol-1-yl}-butyl ester (59 mg, 0.089 mmol) and TFA (138 µL, 1.79 mmol) in dichloromethane (2 mL) was stirred for 4 hrs at room temperature. The volatiles were removed in vacuo and the residue dissolved in dichloromethane. A solution of 4N HCl in dioxane (233 µL, 10 equiv.) was added, followed by concentration. The residue was triturated from diethyl ether and filtered to give the title compound (46 mg, 87%) as a tan solid:

$^1$H NMR (DMSO-d$_6$) δ: 1.14 (s, 9H), 1.69–1.74 (m, 2H), 1.86–1.91 (m, 2H), 4.08–4.11 (m, 4H), 4.48 (t, J=7.3 Hz, 2H), 4.83 (q, J=8.9 Hz, 2H), 5.78 (s, 2H), 7.38 (t, J=7.6 Hz, 1H), 7.40 (d, J=8.1, 1H), 7.53 (d, J=8.6 Hz, 1H), 7.67 (s, 1H), 7.75–7.79 (m, 2H), 8.17 (d, J=7.9 Hz, 1H), 8.27 (br s, 3H);

MS m/e 560 (MH$^+$).

Acetic Acid 4-{5-(tert-butoxycarbonylamino-methyl)-2-[2,4-dioxo-3-(2,2,2-trifluoro-ethyl)-3,4-dihydro-2H-quinazolin-1-ylmethyl]-benzoimidazol-1-yl}-butyl Ester

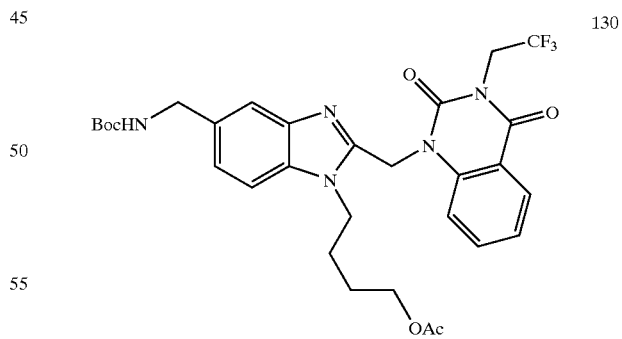

130

To a suspension of [2-[2,4-dioxo-3-(2,2,2-trifluoro-ethyl)-3,4-dihydro-2H-quinazolin-1-ylmethyl]-1-(4-hydroxy-butyl)-1H-benzoimidazol-5-ylmethyl]-carbamic acid tert-butyl ester (100 mg, 0.174 mmol), DIPEA (36 µL, 0.21 mmol), acetyl chloride (14 µL, 0.19 mmol) in dichloromethane (3 mL) was added DMAP (2 mg). The mixture was stirred overnight resulting in the formation of a clear solution. Extra acetyl chloride (5 µL) was added. After 1 hr the solution was quenched with satd. NH$_4$Cl and the aqueous phase extracted with dichloromethane (3×8 mL). The combined organic phases were dried (Na₂SO₄) and concentrated. The residue was purified by flash chromatography (eluens hexane-acetone 3:2) to give the title compound (98 mg, 91%) as a white solid:

hu 1H NMR (CDCl₃) δ 1.45 (s, 9H), 1.64–1.70 (m, 2H), 1.78–1.85 (m, 2H), 2.01 (s, 3H), 4.05 (t, J=6.3 Hz, 2H), 4.33 (t, J=7.4 Hz, 2H), 4.41 (d, J=5.2 Hz, 2H), 4.86 (q, J=8.5 Hz 2H), 4.90 (br s, 1H), 5.73 (s, 2H), 7.28–7.32 (m, 3H), 7.66 (s, 1H), 7.71 (t, J=8.2 Hz, 1H), 8.01 (d, J=8.4 Hz, 1H), 8.23 (d, J=7.7 Hz, 1H);

MS m/e 618 (MH⁺).

Acetic Acid 4-{5-aminomethyl-2-[2,4-dioxo-3-(2,2,2-trifluoro-ethyl)-3,4-dihydro-2H-quinazolin-1-ylmethyl]-benzoimidazol-1-yl}-butyl Ester; HCl Salt

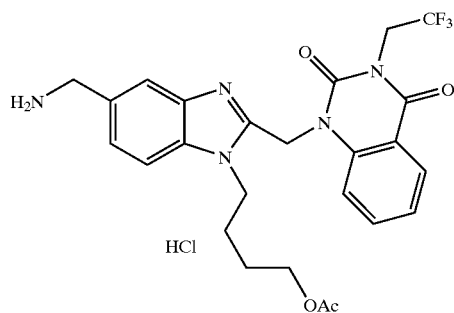

131

A solution of acetic acid 4-{5-(tert-butoxycarbonylaminomethyl)-2-[2,4-dioxo-3-(2,2,2-trifluoro-ethyl)-3,4-dihydro-2H-quinazolin-1-ylmethyl]-benzoimidazol-1-yl}-butyl ester (98 mg, 0.16 mmol) and TFA (244 µL, 3.17 mmol) in dichloromethane (3 mL) was stirred for 4 hrs at room temperature. The volatiles were removed in vacuo and the residue dissolved in dichloromethane. A solution of 4N HCl in dioxane (0.4 mL, 10 equiv.) was added, followed by concentration. The residue was triturated from diethyl ether and filtered to give acetic acid 4-{5-aminomethyl-2-[2,4-dioxo-3-(2,2,2-trifluoro-ethyl)-3,4-dihydro-2H-quinazolin-1-ylmethyl]-benzoimidazol-1-yl }-butyl ester; HCl salt (53 mg, 60%) as a white solid:

¹H NMR (CD₃OD) δ: 1.81–1.90 (m, 2H), 2.03 (s, 3H), 2.04–2.11 (m, 2H), 4.16 (t, J=6.4 Hz, 2H), 4.28 (s, 2H), 4.64 (t, J=7.0 Hz, 2H), 4.85 (hidden q, 2H), 4.90 (br s, 1H), 5.95 (s, 2H), 7.43 (t, J=7.9 Hz, 1H), 7.48 (d, J=8.5 Hz, 1H), 7.64 (d, J=8.3 Hz, 1H), 7.76 (s, 1H), 7.79 (t, J=8.0 Hz, 1H), 7.95 (d, J=8.3 Hz, 1H), 8.30 (d, J=7.9 Hz, 1H);

MS m/e 518.2 (MH⁺).

[2-[2,4-Dioxo-3-(2,2,2-trifluoro-ethyl)-3,4-dihydro-2H-quinazolin-1-ylmethyl]-1-(4-fluoro-butyl)-1H-benzoimidazol-5-ylmethyl]-carbamic Acid tert-butyl Ester

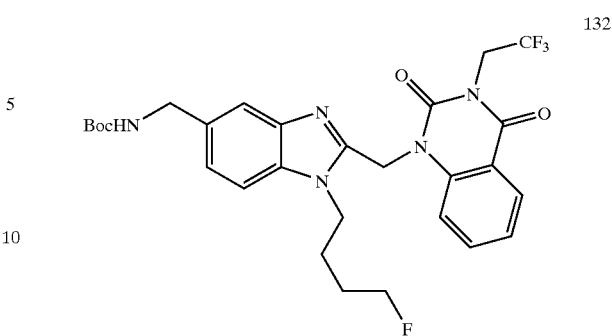

132

The procedure used to prepare [2-(3-cyclopropyl-2,4-dioxo-3,4-dihydro-2H-quinazolin-1-ylmethyl)-1-(4-fluoro-butyl)-1H-benzoimidazol-5-ylmethyl]-carbamic acid tert-butyl ester was followed starting from [2-[2,4-dioxo-3-(2,2,2-trifluoro-ethyl)-3,4-dihydro-2H-quinazolin-1-ylmethyl]-1-(4-hydroxy-butyl)-1H-benzoimidazol-5-ylmethyl]-carbamic acid tert-butyl ester (67 mg, 0.12 mmol). Purification by flash chromatography (eluent 2%, 4% methanol in DCM) afforded [2-[2,4-dioxo-3-(2,2,2-trifluoro-ethyl)-3,4-dihydro-2H-quinazolin-1-ylmethyl]-1-(4-fluoro-butyl)-1H-benzoimidazol-5-ylmethyl]-carbamic acid tert-butyl ester (51 mg, 76%) as a white solid:

¹H NMR (CDCl₃) δ: 1.46 (s, 9H), 1.70–1.80 (m, 2H), 1.85–1.91 (m, 2H), 4.36–4.52 (m, 4H), 4.87 (q, J=8.6, 2H), 4.94 (br s, 1H), 5.89 (s, 2H), 7.32 (t, J=7.6, 1H), 7.37 (br m, 2H), 7.74–7.77 (br m, 2H), 8.05 (d, J=8.5, 1H), 8.24 (d, J=7.6 1H);

MS m/e 578 (MH⁺).

1-[5-Aminomethyl-1-(4-fluoro-butyl)-1H-benzoimidazol-2-ylmethyl]-3-(2,2,2-trifluoro-ethyl)-1H-quinazoline-2,4-dione; HCl Salt

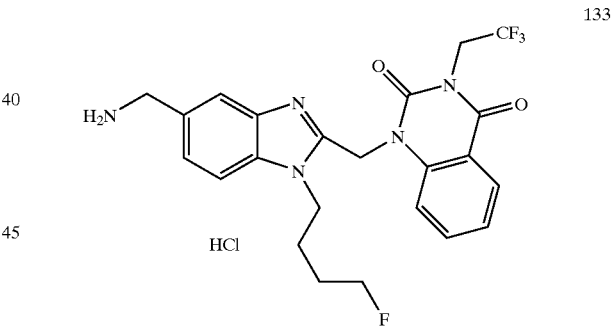

133

To a cooled (0° C.) solution of [2-[2,4-dioxo-3-(2,2,2-trifluoro-ethyl)-3,4-dihydro-2H-quinazolin-1-ylmethyl]-1-(4-fluoro-butyl)-1H-benzoimidazol-5-ylmethyl]-carbamic acid tert-butyl ester (51 mg, 0.088 mmol) in DCM (2 mL) was added TFA (204 µL, 2.65 mmol). The solution was allowed to reach room temperature and stirred for 6 hrs. The volatiles were removed in vacuo and the residue was stripped with methanol. The TFA salt was dissolved in methanol followed by the addition of acetyl cloride (63 µL, 0.88 mmol) and concentrated. This procedure was repeated once. The product was dissolve in methanol and DCM then concenrated (twice). The remaining solid was triturated in diethyl ether to give 1-[5-Aminomethyl-1-(4-fluoro-butyl)-1H-benzoimidazol-2-ylmethyl]-3-(2,2,2-trifluoro-ethyl)-1H-quinazoline-2,4-dione; HCl salt (45 mg, 100%) as a white solid.

¹H NMR (DMSO-d6) δ: 1.73–1.84 (m, 2H), 1.92–1.98 (m, 2H), 4.10 (br q, J=5.5 Hz, 2H), 4.51 (br t, J=7.3 Hz, 2H), 4.52 (dt, J=5.9 Hz, 47, 2H), 4.84 (q, J=8.9 Hz, 2H), 5.83 (s, 2H), 7.39 (t, J=7.3 Hz, 1H), 7.48 (br d, J=7.3 Hz, 1H), 7.54 (d, J=8.6 Hz, 1H), 7.70 (s, 1H), 7.78 (t, J=8.2 Hz, 1H), 7.82 (br d, J=8.2 Hz, 1H), 8.17 (d, J=7.9 Hz, 1H), 8.34 (br s, 3H);

MS m/e 478 (MH⁺).

2,2-Dimethyl-propionic Acid 4-[5-(tert-butoxycarbonylamino-methyl)-2-(4-methoxy-2-oxo-2H-quinolin-1-ylmethyl)-benzoimidazol-1-yl]-butyl Ester

134

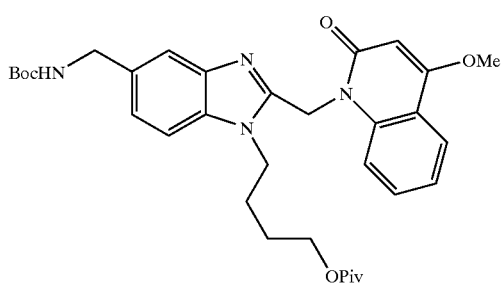

The procedure for the preparation of [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed starting from 4-methoxy-1H-quinolin-2-one (106 mg, 0.605 mmol) and 2,2-dimethyl-propionic acid 4-[5-(tert-butoxycarbonylamino-methyl)-2-chloromethyl-benzoimidazol-1-yl]-butyl ester; HCl salt (296 mg, 0.605 mmol). Purification by flash chromatography (eluent hexane-ethyl acetate 1:1, 1:2, 0:1) afforded 2,2-dimethyl-propionic acid 4-[5-(tert-butoxycarbonylamino-methyl)-2-(4-methoxy-2-oxo-2H-quinolin-1-ylmethyl)-benzoimidazol-1-yl]-butyl ester (240 mg, 67%) as a white solid:

¹H NMR (CDCl₃) δ: 1.12 (s, 9H), 1.44 (s, 9H), 1.46–1.53 (m, 2H), 1.57–1.63 (m, 2H), 3.94 (t, J=6.4 Hz, 2H), 3.97 (s, 3H), 4.30 (t, J=7.0 Hz, 2H), 4.40 (br d, J=5.8 Hz, 2H), 4.97 (br s, 1H), 5.86 (s, 2H), 6.08 (s, 1H), 7.17–7.24 (m, 2H), 7.52 (t, J=8.9 Hz, 1H), 7.66 (s, 1H), 7.92 (d, J=8.2 Hz, 1H), 8.11 (d, J=8.2 Hz, 1H),

MS m/e 591 (MH⁺).

[1-(4-Hydroxy-butyl)-2-(4-methoxy-2-oxo-2H-quinolin-1-ylmethyl)-1H-benzoimidazol-5-ylmethyl]-carbamic Acid tert-butyl Ester

135

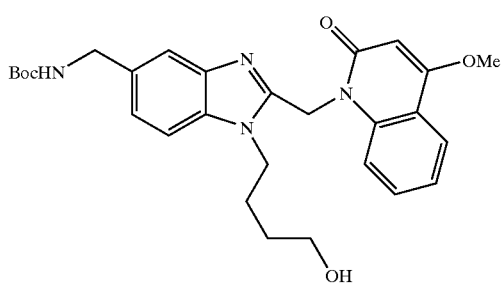

The procedure for the preparation of [2-(3-cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester was followed starting from 2,2-dimethyl-propionic acid 4-[5-(tert-butoxycarbonylamino-methyl)-2-(4-methoxy-2-oxo-2H-quinolin-1-ylmethyl)-benzoimidazol-1-yl]-butyl ester (280 mg, 0.474 mmol). After neutralization more water was added and the resulting white precipitate collected by filtration, which was washed with water (thrice) and diethyl ether (thrice) to yield 204 mg (85%) of [1-(4-hydroxy-butyl)-2-(4-methoxy-2-oxo-2H-quinolin-1-ylmethyl)-1H-benzoimidazol-5-ylmethyl]-carbamic acid tert-butyl ester as a white solid:

¹H NMR (DMSO-d6) δ: 1.37 (s, 9H), 1.46–1.51 (m, 2H), 1.67–1.73 (m, 2H), 3.40 (q, J=6.1 Hz, 2H), 4.00 (s, 3H), 4.15 (d, J=6.1 Hz, 2H), 4.35 (t, J=7.0 Hz, 2H), 4.47 (t, J=4.9 Hz, 1H), 5.75 (s, 2H), 6.14 (s, 1H), 7.25 (t, J=7.6 Hz, 1H), 7.30 (s, 1H), 7.33 (br t, J=6.1 Hz, 1H), 7.47 (d, J=8.2 Hz, 1H), 7.53–7.59 (m, 2H), 7.92 (d, J=7.9 Hz, 1H);

MS m/e 507 (MH⁺).

1-[5-Aminomethyl-1-(4-hydroxy-butyl)-1H-benzoimidazol-2-ylmethyl]-4-methoxy-1H-quinolin-2-one; HCl Salt

136

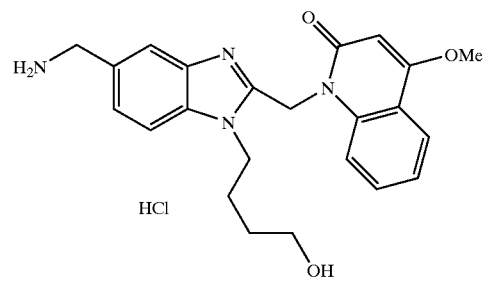

To a cooled (0° C.) suspension of [1-(4-hydroxy-butyl)-2-(4-methoxy-2-oxo-2H-quinolin-1-ylmethyl)-1H-benzoimidazol-5-ylmethyl]-carbamic acid tert-butyl ester (74 mg, 0.15 mmol) in DCM (3 mL) was added TFA (337 µL, 4.38 mmol). The solution was allowed to stir for 6 h at room temperature, followed by the removal of the volatiles in vacuo. The resulting trifluoroacetate was dissolved in methanol (3 mL) followed by the addition of acetyl cloride (104 µL, 1.46 mmol). After 10 minutes the solution was concentrated. This procedure was repeated allowing the reaction to run for 3 hrs. The solution was concentrated in vacuo and the residue stripped with methanol (twice) to yield 1-[5-Aminomethyl-1-(4-hydroxy-butyl)-1H-benzoimidazol-2-ylmethyl]-4-methoxy-1H-quinolin-2-one; HCl salt (65 mg, 100%) as an off white solid:

¹H NMR (DMSO-d6) δ: 1.49–1.55 (m, 2H), 1.79–1.85 (m, 2H), 3.44 (t, J=6.1 Hz, 2H), 4.02 (s, 3H), 4.12 (br q, J=5.5 Hz, 2H), 4.51 (t, J=7.3 Hz, 2H), 5.91 (s, 2H), 6.17 (s, 1H), 7.30 (t, J=6.7 Hz, 1H), 7.52 (br d, J=8.2 Hz, 1H), 7.57–7.61 (m, 2H), 7.72 (s, 1H), 7.85 (br d, J=8.2 Hz, 1H), 7.97 (d, J=7.9 Hz, 1H), 8.41 (br s, 3H);

MS m/e 407 (MH⁺).

[1-(4-Fluoro-butyl)-2-(4-methoxy-2-oxo-2H-quinolin-1-ylmethyl)-1H-benzoimidazol-5-ylmethyl]-carbamic Acid tert-butyl Ester

137

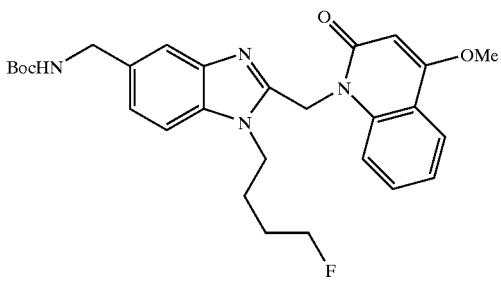

The procedure for the preparation of [2-(3-cyclopropyl-2,4-dioxo-3,4-dihydro-2H-quinazolin-1-ylmethyl)-1-(4-fluoro-butyl)-1H-benzoimidazol-5-ylmethyl]-carbamic acid tert-butyl ester was followed starting from [1-(4-hydroxy-butyl)-2-(4-methoxy-2-oxo-2H-quinolin-1-ylmethyl)-1H-benzoimidazol-5-ylmethyl]-carbamic acid tert-butyl ester (89 mg, 0.18 mmol). Purification by flash chromatography (eluent hexane-acetone 1:1, 1:2) afforded [1-(4-fluoro-butyl)-2-(4-methoxy-2-oxo-2H-quinolin-1-ylmethyl)-1H-benzoimidazol-5-ylmethyl]-carbamic acid tert-butyl ester, that was further purified by preparative HPLC (gradient 50–70% B, 15 min) to furnish the title compound (20 mg, 22%) as a colorless oil:

$^1$H NMR (CDCl$_3$) δ: 1.45 (s, 9H), 1.71–1.77 (m, 4H), 4.01 (s, 3H), 4.37–4.47 (m, 6H), 5.22 (br s, 1H), 6.15 (s, 1H), 6.17 (s, 2H), 7.30 (t, J=7.6, 1H), 7.44–7.50 (m, 2H), 7.63 (t, J=7.9 Hz, 1H), 7.73 (d, J=8.2 Hz, 1H), 7.82 (s, 1H), 8.03 (d, J=8.2 Hz, 1H);

MS m/e 509 (MH$^+$).

1-[5-Aminomethyl-1-(4-fluoro-butyl)-1H-benzoimidazol-2-ylmethyl]-4-methoxy-1H-quinolin-2-one; HCl Salt

138

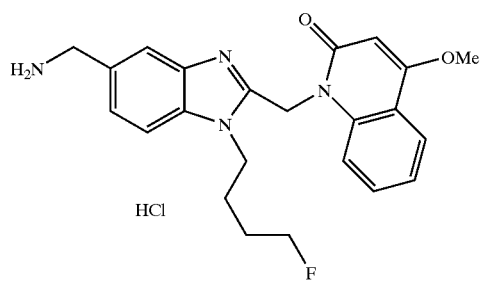

To a cooled (0° C.) solution of [1-(4-fluoro-butyl)-2-(4-methoxy-2-oxo-2H-quinolin-1-ylmethyl)-1H-benzoimidazol-5-ylmethyl]-carbamic acid tert-butyl ester (20 mg, 0.039 mmol) in DCM (1 mL) was added TFA (91 µL, 1.2 mmol). The solution was allowed to reach room temperature and stirred for 3 hrs. The volatiles were removed in vacuo and the residue was stripped with DCM and methanol. The TFA salt was dissolved in methanol followed by the addition of acetyl chloride (28 µL, 0.39 mmol) and concentrated. The product was dissolved in methanol and dichloromethane and concentrated (twice) then the resiude was triturated in diethyl ether to give 1-[5-aminomethyl-1-(4-fluoro-butyl)-1H-benzoimidazol-2-ylmethyl]-4-methoxy-1H-quinolin-2-one; HCl salt (11 mg, 65%) as an off white solid:

$^1$H NMR (DMSO-d6) δ: 1.73–1.82 (m, 2H), 1.85–1.90 (m, 2H), 4.01 (s, 3H), 4.12 (br q, J=4.6 Hz, 2H), 4.44–4.55 (m, 4H), 5.91 (s, 2H), 6.17 (s, 1H), 7.29–7.32 (m, 1H), 7.54 (br d, J=7.9 Hz, 1H), 7.60–7.61 (m, 2H), 7.74 (s, 1H), 7.87 (br d, J=7.3 Hz, 1H), 7.97 (d, J=8.2 Hz, 1H), 8.46 (br s, 3H);

MS m/e 409 (MH$^+$).

3-Vinyl-1H-indazole

139

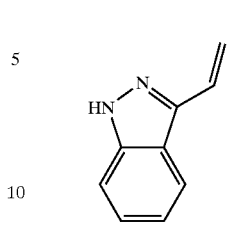

To a solution of 3-bromo-1H-indazole (300 mg, 1.52 mmol) in toluene (8 mL) under nitrogen were subsequently added Pd(PPh$_3$)$_4$ (176 mg, 0.152 mmol) and tributyl vinyltin (532 µL, 1.82 mmol). The reaction mixture was heated at reflux temperature for 1.5 hrs. After cooling to room temperature the black mixture was quenched with satd. NaHCO$_3$ and extracted with ethyl acetate (2×30 mL). The combined organic phases were washed with brine and dried (MgSO$_4$). The resulting orange oil was triturated from diethyl ether and filtered. The filtrate was concentrated in vacuo and purified by flash chromatography (eluent hexane-ethyl acetate 3:1) to yield the title compound (150 mg, 68%) as a pale yellow solid:

$^1$H NMR (DMSO-d6) δ: 5.46 (d, J=11.5 Hz, 1H), 6.08 (d, J=18.2 Hz, 1H), 7.03 (dd, J=11.5 Hz, 18.2 Hz, 1H), 7.17 (t, J=7.3 Hz, 1H), 7.37 (t, J=7.3 Hz, 1H), 7.53 (d, J=8.6 Hz, 1H), 8.00 (d, J=8.2 Hz, 1H), 13.1 (br s, 1H);

MS m/e 145 (MH$^+$).

2,2-Dimethyl-propionic Acid 4-[5-(tert-butoxycarbonylamino-methyl)-2-(3-vinyl-indazol-1-ylmethyl)-benzoimidazol-1-yl]-butyl Ester

140

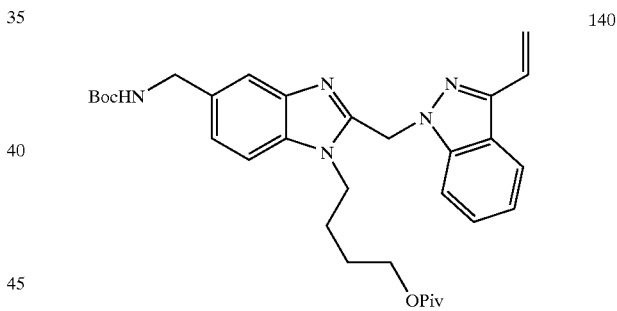

The procedure for the preparation of [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed starting with 3-vinyl-1H-indazole (140 mg, 0.970 mmol) and 2,2-dimethyl-propionic acid 4-[5-(tert-butoxycarbonylamino-methyl)-2-chloromethyl-benzoimidazol-1-yl]-butyl ester; HCl salt (474 mg, 0.614 mmol). After quenching with water, a gum formed. The water was decanted and the residue partitioned between diethyl ether and water. The layers were separated and the aqueous phase extracted with diethyl ether (2×40 mL). The combined organic phases were washed with water (twice), brine, and dried (MgSO$_4$). Purification by flash chromatography (eluent hexane-acetone 2:3) afforded 2,2-dimethyl-propionic acid 4-[5-(tert-butoxycarbonylamino-methyl)-2-(3-vinyl-indazol-1-ylmethyl)-benzoimidazol-1-yl]-butyl ester (386 mg, 71%) as a colorless foam:

$^1$H NMR (DMSO-d6) δ: 1.08 (s, 9H), 1.38 (s, 9H), 1.38 (m, 2H), 1.43–1.47 (m, 2H), 3.88 (t, J=6.1 Hz, 2H), 4.19 (d, J=5.8 Hz, 2H), 4.28 (t, J=7.3 Hz, 2H), 5.49 (d, J=11.5 Hz,

1H), 5.99 (s, 2H), 6.11 (d, J=18.0 Hz, 1H), 7.00 (dd, J=11.5 Hz, 18.0 Hz, 1H), 7.13 (d, J=7.9 Hz, 1H), 7.21 (t, J=7.3 Hz, 1H), 7.37 (br t, J=6.1 Hz, 1H), 7.42–7.48 (m, 3H), 7.75 (d, J=8.6 Hz, 1H), 8.03 (d, J=7.9 Hz, 1H);

MS m/e 560 (MH+).

[1-(4-Hydroxy-butyl)-2-(3-vinyl-indazol-1-ylmethyl)-1H-benzoimidazol-5-ylmethyl]-carbamic Acid tert-butyl Ester

141

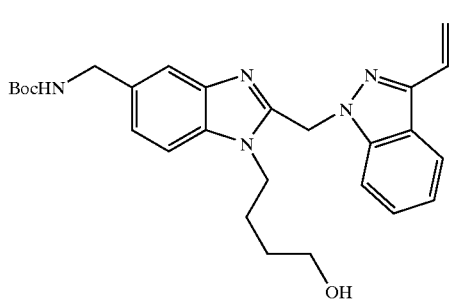

The procedure for the preparation of [2-(3-cyclopropyl-2,4-dioxo-3,4-dihydro-2H-quinazolin-1-ylmethyl)-1-(4-hydroxy-butyl)-1H-benzoimidazol-5-ylmethyl]-carbamic acid tert-butyl ester was followed (reaction time 3 hrs.) starting from 2,2-dimethyl-propionic acid 4-[5-(tert-butoxycarbonylamino-methyl)-2-(3-vinyl-indazol-1-ylmethyl)-benzoimidazol-1-yl]-butyl ester (215 mg, 0.384 mmol). Purification by flash chromatography (eluent 3%, 4% methanol in DCM) afforded [1-(4-hydroxy-butyl)-2-(3-vinyl-indazol-1-ylmethyl)-1H-benzoimidazol-5-ylmethyl]-carbamic acid tert-butyl ester (136 mg, 74%) as a white foam:

$^1$H NMR (DMSO-d6) δ: 1.38 (s, 9H), 1.27–1.38 (m, 4H), 3.26–3.29 (m, 2H), 4.19 (d, J=5.8 Hz, 2H), 4.25 (t, J=7.6 Hz, 2H), 4.39 (t, J=5.2 Hz, 1H), 5.50 (d, J=11.5 Hz, 1H), 5.98 (s, 2H), 6.11 (d, J=18.0 Hz, 1H), 7.00 (dd, J=11.5 Hz, 18.0 Hz, 1H), 7.13 (d, J=7.9 Hz, 1H), 7.22 (t, J=7.3 Hz, 1H), 7.37 (br t, J=6.1 Hz, 1H), 7.42–7.47 (m, 3H), 7.75 (d, J=8.5 Hz, 1H), 8.03 (d, J=8.2 Hz, 1H);

MS m/e 476 (MH+).

4-[5-Aminomethyl-2-(3-vinyl-indazol-1-ylmethyl)-benzoimidazol-1-yl]-butan-1-ol; HCl Salt

142

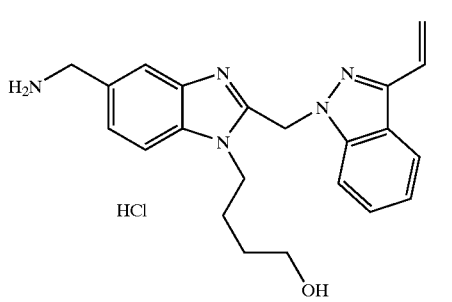

To a suspension of [1-(4-hydroxy-butyl)-2-(3-vinyl-indazol-1-ylmethyl)-1H-benzoimidazol-5-ylmethyl]-carbamic acid tert-butyl ester (17 mg, 0.036 mmol) in DCM (1 mL) was added TFA (82 µL, 1.1 mmol). The solution was allowed to stir for 2.5 hrs. followed by the removal of the volatiles in vacuo. The resulting trifluoroacetate was dissolved in methanol (3 mL) followed by the addition of acetyl cloride (26 µL, 0.36 mmol) and concentrated after 10 min. This procedure was repeated once allowing the reaction to run for 3 hrs. The solution was concentrated in vacuo and the residue stripped with DCM (thrice). The product was triturated in diethyl ether and the ether decanted to yield 4-[5-aminomethyl-2-(3-vinyl-indazol-1-ylmethyl)-benzoimidazol-1-yl]-butan-1-ol; HCl salt (10 mg, 67%) as an off white solid:

$^1$H NMR (DMSO-d6) δ: 1.31–1.37 (m, 2H), 1.45–1.51 (m, 2H), 3.30 (t, J=6.4 Hz, 2H), 4.13–4.16 (m, 2H), 4.43 (t, J=7.0 Hz, 2H), 5.53 (d, J=11.6 Hz, 1H), 6.13 (d, J=18.0 Hz, 1H), 6.19 (s, 2H), 7.01 (dd, J=11.6 Hz, 18.0 Hz, 1H), 7.26 (d, J=7.3 Hz, 1H), 7.49 (t, J=7.9 Hz, 1H), 7.54 (d, J=8.6 Hz, 1H), 7.81 (d, J=8.6 Hz, 1H), 7.86–7.87 (m, 2H), 8.07 (d, J=8.2 Hz, 1H), 8.44 (s, 3H);

MS m/e 376 (MH+).

[2-(3-Ethyl-indazol-1-ylmethyl)-1-(4-hydroxy-butyl)-1H-benzoimidazol-5-ylmethyl]-carbamic Acid tert-butyl Ester

143

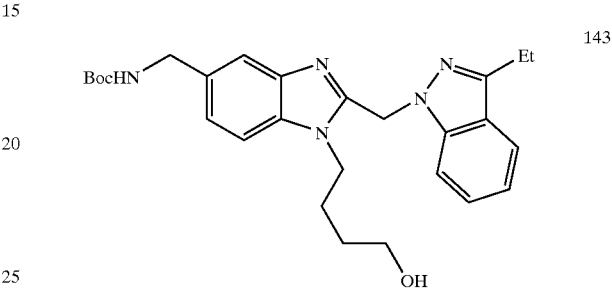

To a solution of [1-(4-hydroxy-butyl)-2-(3-vinyl-indazol-1-ylmethyl)-1H-benzoimidazol-5-ylmethyl]-carbamic acid tert-butyl ester (115 mg, 0.24 mmol) in methanol (35 mL) was added 10% Pd/C (12 mg) and this suspension was rocked in a Parr shaker under a hydrogen atmosphere (45 psi) for 2 hrs. The catalyst was removed by filtration and the filtrate concentrated in vacuo to yield [2-(3-ethyl-indazol-1-ylmethyl)-1-(4-hydroxy-butyl)-1H-benzoimidazol-5-ylmethyl]-carbamic acid tert-butyl ester (106 mg, 92%) as a white foam:

$^1$H NMR (DMSO-d6) δ: 1.24–1.35 (m, 4H), 1.30 (t, J=7.6, 3H), 1.39 (s, 9H), 2.92 (q, J=7.6 Hz, 2H), 3.24–3.27 (m, 2H), 4.19–4.23 (m, 4H), 4.38 (t, J=4.9 Hz, 2H), 5.89 (s, 2H), 7.10–7.14 (m, 2H), 7.35–7.38 (m, 2H), 7.44–7.45 (m, 2H), 7.66 (d, J=8.6 Hz, 1H), 7.75 (d, J=7.9 Hz, 1H);

MS m/e 478 (MH+).

4-[5-Aminomethyl-2-(3-ethyl-indazol-1-ylmethyl)-benzoimidazol-1-yl]-butan-1-ol; HCl Salt

144

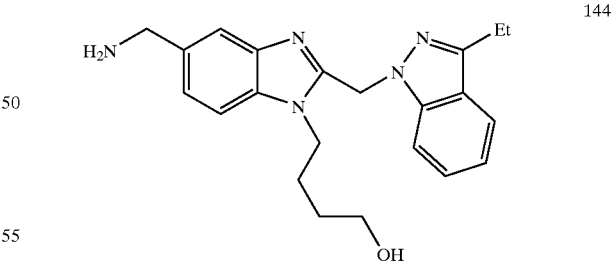

To a cooled (0° C.) suspension of [2-(3-ethyl-indazol-1-ylmethyl)-1-(4-hydroxy-butyl)-1H-benzoimidazol-5-ylmethyl]-carbamic acid tert-butyl ester (55 mg, 0.12 mmol) in DCM (2 mL) was added TFA (266 µL, 3.45 mmol). The solution was allowed to warm to room temperature and stirred for 2.5 hrs., followed by the removal of the volatiles in vacuo. The resulting trifluoroacetate was dissolved in methanol (3 mL) followed by the addition of acetyl cloride (82 µL, 1.2 mmol) and concentrated after 10 min. This procedure was repeated once allowing the reaction to run for 3 hrs. The solution was concentrated in vacuo and the residue stripped with DCM (thrice). The product was triturated in diethyl ether and the ether decanted to 4-[5-aminomethyl-2-(3-ethyl-indazol-1-ylmethyl)-benzoimidazol-1-yl]-butan-1-ol; HCl salt (47 mg, 97%) as an off white solid:

$^1$H NMR (DMSO-d6) δ: 1.30 (t, J=7.6 Hz, 3H), 1.27–1.34 (m, 2H), 1.43–1.49 (m, 2H), 2.93 (q, J=7.6 Hz, 2H), 3.28 (t, J=6.4 Hz, 2H), 4.16–4.19 (m, 2H), 4.44 (t, J=7.3 Hz, 2H), 6.16 (s, 2H), 7.18 (t, J=7.3 Hz, 1H), 7.45 (t, J=7.3 Hz, 1H), 7.61 (d, J=8.2 Hz, 1H), 7.82 (d, J=8.2 Hz, 2H), 7.88 (d, J=8.2 Hz, 1H), 7.94 (s, 1H), 8.53 (br s, 3H);

MS m/e 378 (MH$^+$).

2-Hydroxymethyl-1-(3-methyl-butyl)-1H-benzoimidazole-5-carboxylic Acid

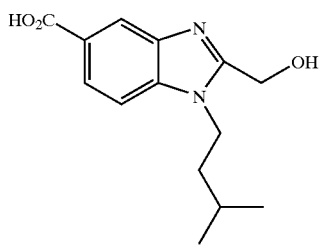

145

A mixture of 2-benzyloxymethyl-1-(3-methyl-butyl)-1H-benzoimidazole-5-carbonitrile (3.7 g, 11 mmol) in 6M HCl (50 mL) was heated at reflux temperature for 4 hrs. The solution was cooled to room temperature and neutralized with concentrated ammonia. A white precipitate formed that was collected by filtration and washed with water and diethyl ether 2-hydroxymethyl-1-(3-methyl-butyl)-1H-benzoimidazole-5-carboxylic acid was obtained as an off white solid (2.4 g, 83%) after drying in vacuo:

$^1$H NMR (DMSO-d6) δ: 0.96 (d, J=6.0 Hz, 6H), 1.65–1.68 (m, 3H), 4.31–4.34 (m, 2H), 4.75 (s, 2H), 5.70 (br s, 1H), 7.62 (d, J=8.5 Hz 1H), 7.87 (d, J=8.5 Hz, 1H), 8.18 (s, 1H), 12.70 (br s, 1H).

2-Hydroxymethyl-1-(3-methyl-butyl)-1H-benzoimidazole-5-carboxylic Acid Methyl Ester

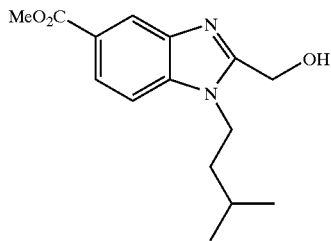

146

A mixture of 2-hydroxymethyl-1-(3-methyl-butyl)-1H-benzoimidazole-5-carboxylic acid (2.4 g, 9.1 mmol) and concentrated sulfuric acid (1.1 g, 10.9 mmol) in methanol (30 mL) was heated at reflux for 40 hrs. The solution was cooled to room temperature, the pH adjusted to 8–9 with concentrated ammonia, and water was added. A white precipitate formed that was collected by filtration and washed with water. The product was dried in vacuo to yield 2-hydroxymethyl-1-(3-methyl-butyl)-1H-benzoimidazole-5-carboxylic acid methyl ester (2.4 g, 96%) as a white solid.

$^1$H NMR (DMSO-d6) δ: 0.96 (d, J=6.0 Hz, 6H), 1.65–1.68 (m, 3H), 3.87 (s, 3H), 4.31–4.34 (m, 2H), 4.75 (d, J=5.4 Hz, 2H), 5.70 (br t, J=5.4 Hz, 1H), 7.65 (d, J=8.5 Hz, 1H), 7.89 (d, J=8.5 Hz, 1H), 8.20 (s, 1H);

MS m/e 277 (MH$^+$).

2-Chloromethyl-1-(3-methyl-butyl)-1H-benzoimidazole-5-carboxylic Acid Methyl Ester; HCl Salt

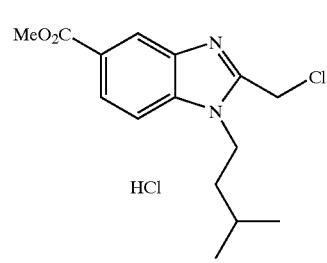

147

To a cooled (0° C.) solution of 2-hydroxymethyl-1-(3-methyl-butyl)-1H-benzoimidazole-5-carboxylic acid methyl ester (1.00 g, 3.62 mmol) in DCM (10 mL) was added thionyl chloride (396 μL, 5.43 mmol). The solution was stirred at 0° C. for 15 min. and concentrated in vacuo to give 2-chloromethyl-1-(3-methyl-butyl)-1H-benzoimidazole-5-carboxylic acid methyl ester; HCl salt (1.20 g, 100%) as a white solid, which was used without further purification:

$^1$H NMR (DMSO-d6) δ: 0.98 (d, J=6.0 Hz, 6H), 1.68–1.75 (m, 3H), 3.88 (s, 3H), 4.36–4.39 (m, 2H), 5.15 (s, 2H), 7.76 (d, J=8.5 Hz, 1H), 7.96 (d, J=8.5 Hz, 1H), 8.26 (s, 1H);

MS m/e 295 (MH$^+$).

2-(3-Cyclopropyl-2,4-dioxo-3,4-dihydro-2H-quinazolin-1-ylmethyl)-1-(3-methyl-butyl)-1H-benzoimidazole-5-carboxylic Acid Methyl Ester

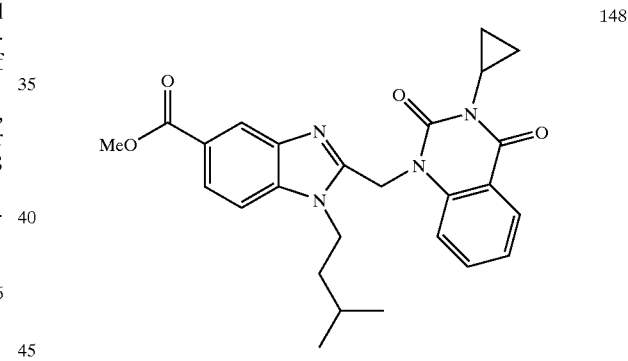

148

The procedure for the preparation of [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed starting from 3-cyclopropyl-1H-quinazoline-2,4-dione (309 mg, 1.53 mmol) and 2-chloromethyl-1-(3-methyl-butyl)-1H-benzoimidazole-5-carboxylic acid methyl ester; HCl salt (506 mg, 1.53 mmol). At the end of the reaction a precipitate had formed. The mixture was diluted with water, and the solid collected by filtration. After washing with water and diethyl ether and drying in vacuo, 2-(3-Cyclopropyl-2,4-dioxo-3,4-dihydro-2H-quinazolin-1-ylmethyl)-1-(3-methyl-butyl)-1H-benzoimidazole-5-carboxylic acid methyl ester (634 mg, 90%) was obtained as a white solid:

$^1$H NMR (DMSO-d6) δ: 0.73–0.76 (m, 2H), 1.00 (d, J=6.4 Hz, 6H), 1.03–1.07 (m, 2H), 1.65–1.75 (m, 3H), 2.75–2.78 (m, 1H), 3.83 (s, 3H), 4.40–4.43 (m, 2H), 5.66 (s, 2H), 7.29 (t, J=7.5 Hz, 1H), 7.50 (d, J=8.5 Hz, 1H), 7.67–7.70 (m, 2H), 7.88 (d, J=7.4 Hz, 1H), 8.07–8.09 (m, 2H);

MS m/e 461 (MH$^+$).

2-(3-Cyclopropyl-2,4-dioxo-3,4-dihydro-2H-quinazolin-1-ylmethyl)-1-(3-methyl-butyl)-1H-benzoimidazole-5-carboxylic Acid

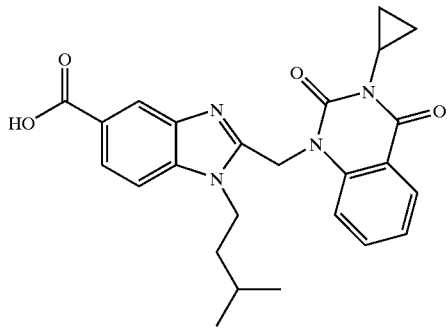

149

A mixture of 2-(3-cyclopropyl-2,4-dioxo-3,4-dihydro-2H-quinazolin-1-ylmethyl)-1-(3-methyl-butyl)-1H-benzoimidazole-5-carboxylic acid methyl ester (110 mg, 0.239 mmol) and 1N NaOH (0.5 mL) in THF (6 mL) and water (6 mL) was heated overnight at 65° C. The solution was cooled to room temperature and neutralized with 0.5 mL 1M HCl. THF was removed in vacuo which resulted in the formation of a white precipitate, that was collected by filtration and washed with water. After drying in vacuo 2-(3-cyclopropyl-2,4-dioxo-3,4-dihydro-2H-quinazolin-1-ylmethyl)-1-(3-methyl-butyl)-1H-benzoimidazole-5-carboxylic acid (77 mg, 72%) was obtained as an off white solid.

$^1$H NMR (DMSO$^{d6}$) δ 0.69 (m, 2H), 1.00 (d, J=6.0 Hz, 6H), 1.04–1.06 (m, 2H), 1.66–1.74 (m, 3H), 2.76 (br s, 1H), 4.39–4.42 (m, 2H), 5.66 (s, 2H), 7.29 (t, J=7.3 Hz, 1H), 7.50 (d, J=8.3 Hz, 1H), 7.64–7.70 (m, 2H), 7.86 (d, J=8.4 Hz, 1H), 8.06–8.08 (m, 2H), 12.65 (br s, 1H);

MS m/e 447 (MH$^+$).

3-Cyclopropyl-1-[5-hydroxymethyl-1-(3-methyl-butyl)-1H-benzoimidazol-2-ylmethyl]-1H-quinazoline-2,4-dione

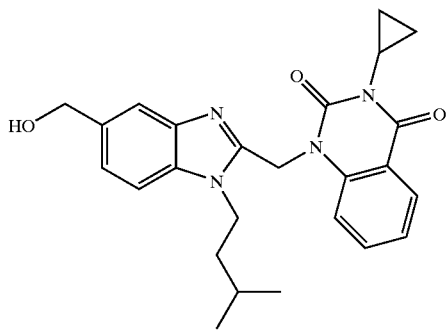

150

To a cooled (0° C.) solution of 2-(3-cyclopropyl-2,4-dioxo-3,4-dihydro-2H-quinazolin-1-ylmethyl)-1-(3-methyl-butyl)-1H-benzoimidazole-5-carboxylic acid (77 mg, 0.17 mmol) and N-methyl morpholine (23 µL, 0.21 mmol) in DCM (3 mL) was added isobutyl chloroformate (27 µL, 0.21 mmol. The mixture was allowed to warm to room temperature and stirred for 2 hrs. After concentration and trituration with ethyl acetate the solid was removed by filtration and the filtrate concentrated in vacuo. The residue containing the mixed anhydride was dissolved in THF (3 mL) and added to a stirred and cooled (0° C.) solution of sodium borohydride (65 mg, 1.7 mmol) in water. The mixture was allowed to warm to room temperature and stirred for 3 hrs., followed by quenching with satd. Na/K tartrate and stirring overnight. The mixture was extracted with ethyl acetate (3×10 mL), the combined organic phases washed with brine and dried (MgSO$_4$). Purification by flash chromatography (eluent 2%, 5% methanol in DCM) afforded 3-cyclopropyl-1-[5-hydroxymethyl-1-(3-methyl-butyl)-1H-benzoimidazol-2-ylmethyl]-1H-quinazoline-2,4-dione (39 mg, 52%) as a white solid.

$^1$H NMR (DMSO-d6) δ: 0.73–0.76 (m, 2H), 0.99 (d, J=6.3 Hz, 6H), 1.04–1.08 (m, 2H), 1.61–1.71 (m, 3H), 2.74–2.78 (m, 1H), 4.34 (t, J=7.6 Hz, 2H), 4.52 (d, J=5.7 Hz, 1H), 5.07 (t, J=5.7 Hz, 1H), 5.62 (s, 2H), 7.20 (d, J=8.1 Hz, 1H), 7.27 (t, J=7.3 Hz, 1H), 7.41 (s, 1H), 7.47 (d, J=8.2 Hz, 1H), 7.50 (d, J=8.5 Hz, 1H), 7.67 (t, J=7.8 Hz, 1H), 8.06 (d, J=7.4 Hz, 1H);

MS m/e 433 (MH$^+$).

N-Hydroxy-2-(3-isopropyl-2-oxo-2,3-dihydro-benzoimidazol-1-ylmethyl)-1-(3-methyl-butyl)-1H-benzoimidazole-5-carboxamidine

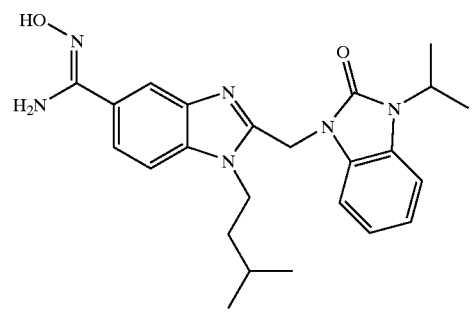

151

A mixture containing 2-(3-isopropyl-2-oxo-2,3-dihydro-benzoimidazol-1-ylmethyl)-1-(3-methyl-butyl)-1H-benzoimidazole-5-carbonitrile (152 mg, 0.379 mmol), hydroxylamine hydrochloride (95 mg, 1.36 mmole) and potassium carbonate (105 mg, 0.758 mmole) in ethanol (4 mL) and water (2 mL) in a sealed tube was placed in a microwave oven (Smith Creator, Personal Chemistry) and heated at 140° C. for 15 min, followed by 150° C. for 10 min while stirring. The solvents were removed in vacuo and the residue was triturated with water. The white precipitate was collected by filtration, washed with water and dried in vacuo to give N-hydroxy-2-(3-isopropyl-2-oxo-2,3-dihydro-benzoimidazol-1-ylmethyl)-1-(3-methyl-butyl)-1H-benzoimidazole-5-carboxamidine (140 mg, 85%) as a white solid:

$^1$H NMR (DMSO-d6) δ: 0.90 (d, J=6.6 Hz, 6H), 1.37–1.41 (m, 2H), 1.48 (d, J=6.9 Hz, 6H), 1.60–1.66 (m, 1H), 4.29–4.32 (m, 2H), 4.64–4.70 (m, 1H), 5.35 (s, 2H), 5.81 (br s, 2H), 7.00 (t, J=7.6 Hz, 1H), 7.04 (t, J=7.6 Hz, 1H), 7.24 (d, J=7.6 Hz, 1H), 7.34 (d, J=7.6 Hz, 1H), 7.47 (d, J=8.6 Hz, 1H), 7.62 (d, J=8.6 Hz, 1H), 7.92 (s, 1H), 9.53 (br s, 1H);

MS m/e 435 (MH$^+$).

1-Isopropyl-3-[1-(3-methyl-butyl)-5-[1,2,4]oxadiazol-3-yl-1H-benzoimidazol-2-ylmethyl]-1,3-dihydro-benzoimidazol-2-one

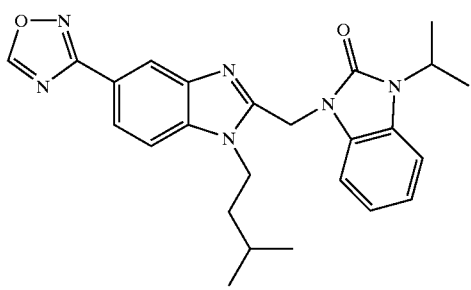

152

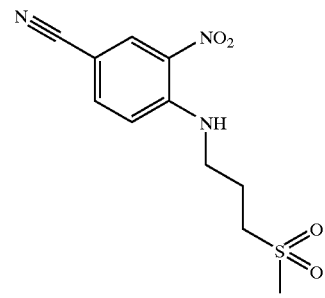

A solution of N-hydroxy-2-(3-isopropyl-2-oxo-2,3-dihydro-benzoimidazol-1-ylmethyl)-1-(3-methyl-butyl)-1H-benzoimidazole-5-carboxamidine (65 mg, 0.15 mmol) in trimethyl orthoformate (4 mL) in the presence of BF$_3$.OEt$_2$ (5 μL) in a sealed tube was placed in a microwave oven (Smith Creator, Personal Chemistry) and heated at 80° C. for 5 min while stirring. The solvent was removed in vacuo and purified by flash chromatography (eluent hexane-acetone 3:1) to give 1-isopropyl-3-[1-(3-methyl-butyl)-5-[1,2,4]oxadiazol-3-yl-1H-benzoimidazol-2-ylmethyl]-1,3-dihydro-benzoimidazol-2-one (35 mg, 53%) as a white solid:

$^1$H NMR (DMSO-d6) δ 0.91 (d, J=6. Hz, 6H), 1.41–1.45 (m, 2H), 1.49 (d, J=6.9 Hz, 6H), 1.63–1.68 (m, 1H), 4.34–4.37 (m, 2H), 4.65–4.70 (m, 1H), 5.40 (s, 2H), 7.01 (t, J=7.6 Hz, 1H), 7.05 (t, J=7.6 Hz, 1H), 7.25 (d, J=7.6 Hz, 1H), 7.35 (d, J=7.6 Hz, 1H), 7.72 (d, J=8.5 Hz, 1H), 7.95 (d, J=8.5 Hz, 1H), 8.26 (s, 1H), 9.67 (s, 2H);

MS m/e 445 (MH$^+$).

4-(3-Methylsulfanyl-propylamino)-3-nitro-benzonitrile

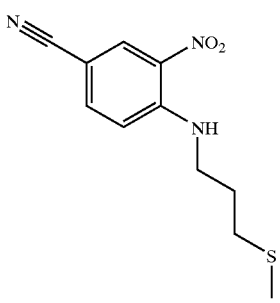

153

To a solution of 4-chloro-3-nitrobenzonitrile (17.3 g, 95 mmol) was added 3-thiomethylpropylamine (10.4 ml, 95.0 mmol) and K$_2$CO$_3$ (26.2 g, 190 mmol) and the mixutre stirred for 12 h. Additional 3-thiomethylpropylamine (1.0 g, 9.5 mmol) was added and the mixture heated to reflux for 4 h then cooled and concentrated to give 28 g (29%) of 4-(3-methylsulfanyl-propylamino)-3-nitro-benzonitrile as a yellow solid.

$^1$H NMR (CDCl$_3$) δ: 2.01–2.10 (m, 2H), 2.11 (s, 3H), 2.63–2.65 (m, 2H), 3.50–3.54 (m, 2H), 6.96–6.99 (m, 1H), 2.60–2.63 (m, 1H), 8.46–8.52 (m, 2H);

MS m/e 251 (MH$^+$).

4-(3-Methanesulfonyl-propylamino)-3-nitro-benzonitrile

154

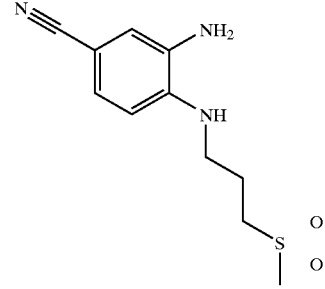

4-(3-Methylsulfanyl-propylamino)-3-nitro-benzonitrile (28 g, 111.5 mmol) was dissolved in DMF (500 mL) and cooled to 0° C. and treated with magnesium monoperoxyphthalic acid (100 g, 223 mmol) and stirred for 12 h. The DMF was removed the solid triturated with EtOAc then filtered. The filter cake was washed with saturated NaHCO$_3$ then water. 4-(3-Methanesulfonyl-propylamino)-3-nitro-benzonitrile was obtained as a yellow solid 18.4 g, (58%).

$^1$H NMR (DMSO-d6) δ: 1.99–2.02 (m, 2H), 2.98 (s, 3H), 3.21 (t, J=7.7 Hz, 2H), 3.55–3.59 (m, 2H), 7.24 (d, J=9.15 Hz, 1H), 7.84 (dd, J=1.8, 9.0 Hz, 1H), 8.51 (d, J=2 Hz, 1H), 8.66–8.90 (m, 1H);

MS m/e 283 (MH$^+$);

Calcd for C$_{11}$H$_{13}$N$_3$O$_4$S; % C, 46.63; % H, 4.62; % N, 14.83;

Found % C, 46.67; % H, 4.61, % N, 6.64.

4-(3-Methanesulfonyl-propylamino)-3-amino-benzonitrile

155

A solution of 4-(3-methanesulfonyl-propylamino)-3-nitro-benzonitrile (3.0 g, 10.6 mmol) in MeOH/DMF (60 ml, 1/1) was hydrogenated on a PARR hydrogenator at 50 psi for 4 h. The solution was filtered and concentrated. The residue was triturated with EtOAc to give 4-(3-methanesulfonyl-propylamino)-3-amino-benzonitrile 1.55 g (58%) as a tan solid.

$^1$H NMR (DMSO-d6) δ: 1.96–2.02 (m, 2H), 2.98 (s, 3H), 3.22–3.26 (m, 2H), 3.35–3.40 (m, 2H), 4.98(br s, 2H), 5.46–5.48 (m, 1H), 6.49 (d, J=8.2 Hz, 1H), 6.78 (s, 1H), 6.93 (d, J=8.2 Hz, 1H);

MS m/e 253 (MH$^-$).

[2-Hydroxymethyl-1-(3-methanesulfonyl-propyl)-1H-benzoimidazol-5-ylmethyl]-carbamic Acid tert-butyl Ester

156

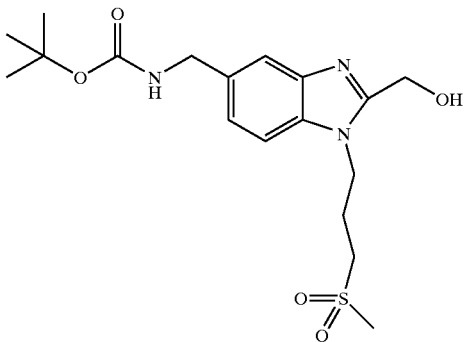

To a slurry of 4-(3-methanesulfonyl-propylamino)-3-amino-benzonitrile (1.55 g, 6.12 mmol) in $CH_2Cl_2$ (100 ml) was added $Et_3N$ (0.13 ml, 0.91 mmol). The mixture is cooled to −78° C. and stirred for 10 minutes. Acetoxyacetylchloride (0.84 ml, 7.9 mmol) was added and the mixture stirred for 12 h at 23° C. The reaction mixture was washed with 1N HCl, dried over $MgSO_4$ and concentrated. The residue was dissolved in AcOH (50 ml) and heated to reflux for 2 h. The solvent was removed to give [2-hydroxymethyl-1-(3-methanesulfonyl-propyl)-1H-benzoimidazol-5-ylmethyl]-carbamic acid tert-butyl ester 2.3 g (89%) as a tan solid. The solid was dissolved in DMF (50 ml) and cooled to 0° C. and treated with $Boc_2O$ (2.15 g, 9.86 mmol) and stirred for 12 h. The solvent is removed and the residue purified by chromatography to give 0.93 g (19%) of [2-hydroxymethyl-1-(3-methanesulfonyl-propyl)-1H-benzoimidazol-5-ylmethyl]-carbamic acid tert-butyl ester.

$^1$H NMR (DMSO-d6) δ: 2.20–2.28 (m, 2H), 2.99 (s, 3H), 3.31 (t, J=7.6 Hz, 2H), 4.57 (t, J=7.2 Hz, 2H), 5.00 (s, 2H), 7.73 (d, J=8.4 Hz, 1H), 7.99 (s, 1H), 8.03 (d, J=8.4 Hz, 1H), 8.80–8.90 (br s, 2H);

MS m/e 297 (MH$^+$).

[2-[2,4-Dioxo-3-(2,2,2-trifluoro-ethyl)-3,4-dihydro-2H-quinazolin-1-ylmethyl]-1-(3-methanesulfonyl-propyl)-1H-benzoimidazol-5-ylmethyl]-carbamic Acid tert-butyl Ester

157

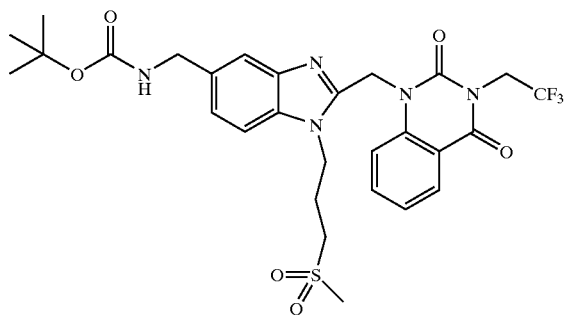

To a solution of [2-hydroxymethyl-1-(3-methanesulfonyl-propyl)-1H-benzoimidazol-5-ylmethyl]-carbamic acid tert-butyl ester (0.34 g, 0.86 mmol) in $CH_2Cl_2$ (50 ml) at 0° C. was added $SOCl_2$ (0.094 ml, 1.29 mmol) and the mixture stirred at 0° C. for 15 minutes then concentrated. The residue, 300 mg (89%), was a 9:1 mixture of the desired [2-chloromethyl-1-(3-methanesulfonyl-propyl)-1H-benzoimidazol-5-ylmethyl]-carbamic acid tert-butyl ester and a small of amount of C-[2-Chloromethyl-1-(3-methanesulfonyl-propyl)-1H-benzoimidazol-5-yl]-methylamine respectively. The solid was used without further purification.

A slurry of 3-(2,2,2-trifluoro-ethyl)-1H-quinazoline-2,4-dione (88 mg, 0.36 mmol) in THF (20 ml) was treated with BTPP (0.33 ml, 1.08 mmol) and stirred for 15 min at 23° C. [2-Chloromethyl-1-(3-methanesulfonyl-propyl)-1H-benzoimidazol-5-ylmethyl]-carbamic acid tert-butyl ester (150 mg, 0.36 mmol) was added and the mixture stirred at 23° C. for 12 h. The solvent was removed and the residue triturated with water. The residue was chromatographed to give 40 mg (18%) of [2-[2,4-dioxo-3-(2,2,2-trifluoro-ethyl)-3,4-dihydro-2H-quinazolin-1-ylmethyl]-1-(3-methanesulfonyl-propyl)-1H-benzoimidazol-5-ylmethyl]-carbamic acid tert-butyl ester as a white solid.

$^1$H NMR (DMSO-d6) δ: 1.36 (s, 9H), 2.24–2.28 (m, 2H), 3.03 (s, 3H), 3.27–3.32 (m, 2H), 4.15 (d, J=6.05 Hz, 2H), 4.50 (t, J=7.4 Hz, 2H), 4.83 (q, J=8.8 Hz, 2H), 5.70 (s, 2H), 7.15 (d, J=7.6 Hz, 1H), 7.32–7.39 (m, 3H), 7.58 (t, J=8.6 Hz, 1H), 7.76 (t, J=7.9 Hz, 1H), 8.15 (d, J=7.9 Hz, 1H);

MS m/e 623 (MH$^+$).

1-[5-Aminomethyl-1-(3-methanesulfonyl-propyl)-1H-benzoimidazol-2-ylmethyl]-3-(2,2,2-trifluoro-ethyl)-1H-quinazoline-2,4-dione

158

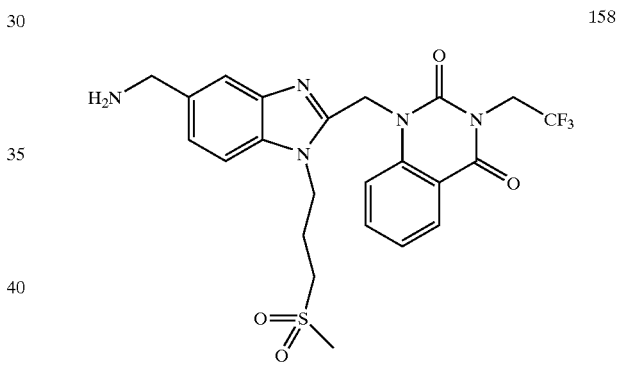

To a solution of [2-[2,4-dioxo-3-(2,2,2-trifluoro-ethyl)-3,4-dihydro-2H-quinazolin-1-ylmethyl]-1-(3-methanesulfonyl-propyl)-1H-benzoimidazol-5-ylmethyl]-carbamic acid tert-butyl ester (40 mg, 0.064 mmol) was added HCl (5 ml, 4.0 M in dioxane) and the mixture stirred for 12 h. The solvent was removed to give a white solid. The solid was purified by preparative HPLC to give 16.6 mg (40%) of 1-[5-aminomethyl-1-(3-methanesulfonyl-propyl)-1H-benzoimidazol-2-ylmethyl]-3-(2,2,2-trifluoro-ethyl)-1H-quinazoline-2,4-dione as a white powder.

$^1$H NMR (DMSO-d6) δ: 2.25–2.37 (m, 2H), 3.03 (s, 3H), 3.29 (t, J=7.5 Hz, 2H), 4.07 (d, J=5.6 Hz, 2H), 4.53 (t, J=7.4 Hz, 2H), 4.84 (q, J=9.0 Hz, 2H), 5.73 (s, 2H), 7.35–7.39 (m, 2H), 7.56 (d, J=8.6 Hz, 1H), 7.60 (s, 1H), 7.71 (d, J=8.3 Hz, 1H), 7.77 (t, J=7.8 Hz, 1H), 8.00–8.10 (br s, 2H), 8.16 (d, J=7.9 Hz, 1H);

MS m/e 523 (MH$^+$).

4-(4-Fluoro-butylamino)-3-nitro-benzonitrile

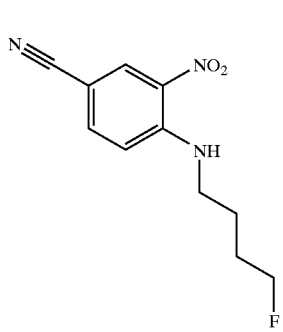

159

A mixture of 3-nitro-4-aminocarbonitrile (6.0 g, 36.8 mmol), $K_2CO_3$ (9.9 g, 72 mmol) and 4-bromo-1-fluorobutane (5.7 g, 36.8 mmol) was stirred in DMF (50 ml) at 100° C. for 12 h. The mixture was cooled and concentrated. The solid residue was washed with EtOAc and filtered. The organic layer was dried over $MgSO_4$ and concentrated. The organic residue was purified by column chromatography to give 2.2 g, (25%) of 4-(4-fluoro-butylamino)-3-nitro-benzonitrile as a yelow solid.

$^1$H NMR ($CDCl_3$) δ: 1.82–1.85 (m, 1H), 1.89–1.93 (m, 3H), 3.44 (q, J=6.7 Hz, 2H), 4.89 (t, J=5.6 Hz 1H), 4.58 (t, J=5.4 Hz, 1H), 6.92 (d, J=9.0 Hz, 1H), 7.61 (dd, J=1.6 Hz, 7.5 Hz, 1H), 8.40–8.51 (br s, 1H), 8.51 (d, J=2.0 Hz, 1H);

MS m/e 237 (MH$^+$);

Anal. Calcd for $C_{11}H_{12}FN_3O_2$: % C, 55.69; % H, 5.09; % N, 17.71; Found: % C, 55.56; % H, 5.03; % N, 17.65.

3-Amino-4-(4-fluoro-butylamino)-benzonitrile

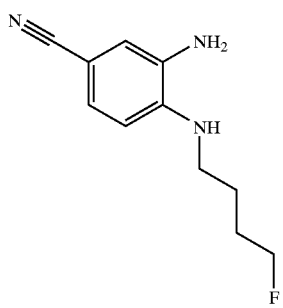

160

A solution of 4-(4-fluoro-butylamino)-3-nitro-benzonitrile (2.2 g, 9.3 mmol) in EtOH (50 ml) was hydrogenated at 50 psi with 10% Pd/C for 2 h then filtered and concentrated. 3-Amino-4-(4-fluoro-butylamino)-benzonitrile 1.9 g (99%) was used without further purification.

$^1$H NMR ($CDCl_3$) δ: 1.81–1.95 (m, 4H), 3.23 (t, J=6.5 Hz, 2H), 4.47 (t, J=5.5 Hz, 1H), 4.56 (t, J=5.5 Hz, 1H), 6.58 (d, J=8.3 Hz, 1H), 6.94 (s, 1H), 7.16 (dd, J=1.8, 8.2 Hz, 1H);

MS m/e 207 (MH$^+$).

Acetic Acid [5-cyano-2-(4-fluoro-butylamino)-phenylcarbamoyl]-methyl Ester

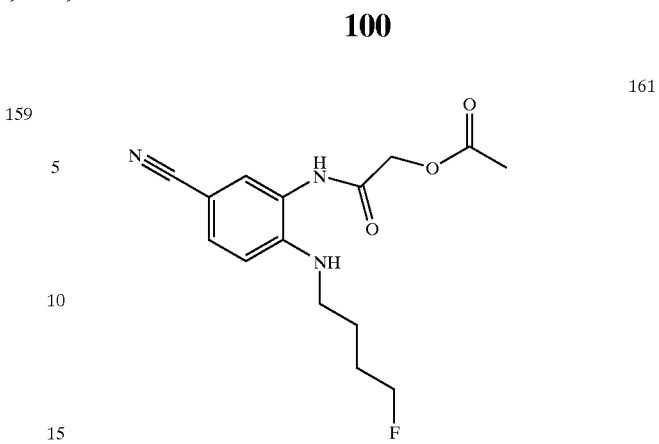

161

To a solution of 3-amino-4-(4-fluoro-butylamino)-benzonitrile (1.9 g, 9.23 mmol) in $CH_2Cl_2$ (50 mL) at −78° C. was added acetoxyacetylchloride (0.99 ml, 9.23 mmol) and $Et_3N$ (1.67 ml, 12.0 mmol). The mixture was allowed to warm to 23° C. and stirred for 12 h. The reaction mixture is washed with 1 N HCl, dried over $MgSO_4$ and concentrated. Acetic acid [5-cyano-2-(4-fluoro-butylamino)-phenylcarbamoyl]-methyl ester 2.5 g (88%) was used without further purification.

$^1$H NMR ($CDCl_3$) δ: 1.38–1.60 (m, 2H), 1.61–1.78 (m, 2H), 2.24 (s, 3H), 3.23 (t, J=6.6 Hz, 2H), 4.50 (dt, J=5.4, 47 Hz, 2H), 4.71 (s, 2H), 6.69 (d, J=8.6 Hz, 1H), 7.39 (s, 1H), 7.44 (dd, J=1.7, 7.4 Hz, 1H);

MS m/e 307 (MH$^+$).

Acetic Acid 5-cyano-1-(4-fluoro-butyl)-1H-benzoimidazol-2-ylmethyl Ester

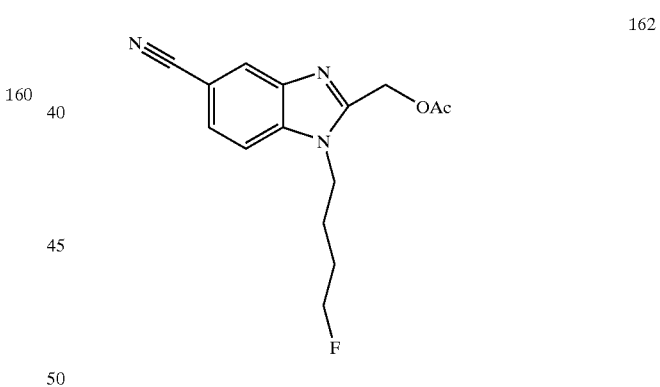

162

Acetic acid [5-cyano-2-(4-fluoro-butylamino)-phenylcarbamoyl]-methyl ester (2.5 g, 8.14 mmol)was dissolved in AcOH (20 mL) and heated to reflux for 2 h. The reaction mixture was concentrated and the residue dissolved in EtOAc and washed with saturated $NaHCO_3$. The organic layer is dried over $MgSO_4$ and concentrated to give 1.3 g (55%) of acetic acid 5-cyano-1-(4-fluoro-butyl)-1H-benzoimidazol-2-ylmethyl ester as a dark solid.

$^1$H NMR ($CDCl_3$) δ: 1.74–1.82 (m, 2H), 1.99–2.04 (m, 2H), 2.16 (s, 3H), 4.29 (t, J=7.6 Hz, 2H), 4.50 (dt, J=5.6, 47.1 Hz, 2H), 5.39 (s, 2H), 7.45 (d, J=8.5 Hz, 1H), 7.58 (dd, J=1.3, 8.5 Hz, 1H), 8.11 (d, J=1.3 Hz, 1H);

MS m/e 289 (MH$^+$).

[5-Aminomethyl-1-(4-fluoro-butyl)-1H-benzoimidazol-2-yl]-methanol

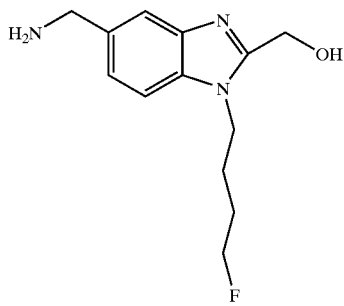

To a solution of acetic acid 5-cyano-1-(4-fluoro-butyl)-1H-benzoimidazol-2-ylmethyl ester (1.3 g, 4.5 mmol) in MeOH (50 ml), EtOH (10 ml), concentrated HCl (10 ml) and 10% Pd/C (100 mg) was hydrogenated for 2 h. The solution was filtered and concentrated. The residue was dissolved in EtOAc and washed with aq NaHCO₃. The product remains in the aqueous layer. The water was removed and the residue washed with hot EtOAc. The EtOAc extracts are concentrated to give 0.32 g (18%) of [5-aminomethyl-1-(4-fluoro-butyl)-1H-benzoimidazol-2-yl]-methanol as a white solid.

¹H NMR (DMSO-d6) δ: 1.64–1.72 (m, 2H), 1.83–1.89 (m, 2H), 2.10–2.40 (br s, 1H), 3.20–3.41 (br s, 1H), 3.80 (s, 2H), 4.29 (t, J=7.3 Hz, 2H), 4.45 (dt, J=6.0, 47.4 Hz, 2H), 4.70 (s, 2H), 5.55–5.68 (br s, 1H), 7.20 (dd, J=1.4, 8.3 Hz, 1H), 7.47 (d, J=8.3 Hz, 1H), 7.53 (s, 1H);

MS m/e 251 (MH⁺).

[1-(4-Fluoro-butyl)-2-hydroxymethyl-1H-benzoimidazol-5-ylmethyl]-carbamic Acid tert-butyl Ester

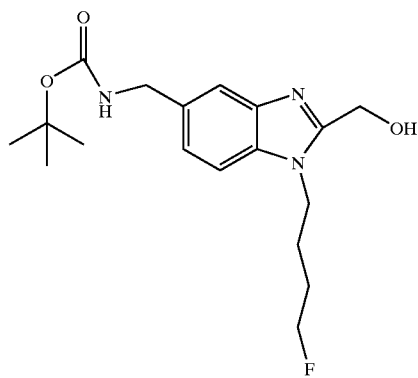

[5-Aminomethyl-1-(4-fluoro-butyl)-1H-benzoimidazol-2-yl]-methanol (321 mg, 1.28 mmol) was dissolved in DMF (20 ml) at 0° C. and treated with t-butylpyrocarbonate (0.28 g, 1.2 mmol) and the mixture stirred for 12 h. Additional t-butylpyrocarbonate (0.28 g, 1.28 mmol) was added and stirring continued for 4 h. The solvent is removed and the residue purified by column chromatography with 10% MeOH/CH₂Cl₂ as eluant to give 370 mg (82%) of the product as a yellow oil.

¹H NMR (CDCl₃) δ: 1.47 (s, 9H), 1.51–1.65 (br s, 1H), 1.66–1.81 (m, 2H), 1.95–2.05 (m, 2H), 3.49 (s, 2H), 4.26 (t, J=7.3 Hz, 2H), 4.40–4.45 (m, 2H), 4.50 (t, J=7.3 Hz, 1H), 4.88 (s, 2H), 7.20–7.29 (m, 2H), 7.59 (s, 1H);

MS m/e 351 (MH⁺).

1-[5-Aminomethyl-1-(4-fluoro-butyl)-1H-benzoimidazol-2-ylmethyl]-3-methyl-1H-cinnolin-4-one

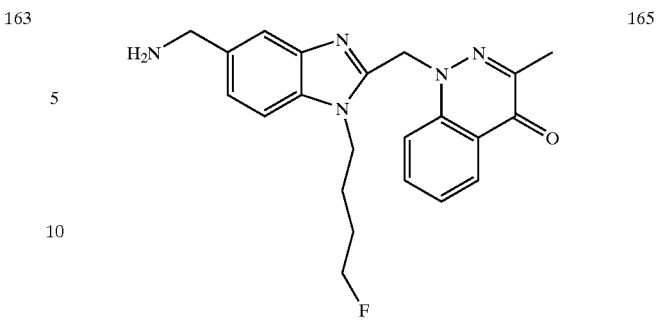

[1-(4-Fluoro-butyl)-2-hydroxymethyl-1H-benzoimidazol-5-ylmethyl]-carbamic acid tert-butyl ester (120 mg, 0.24 mmol) was dissolved in 4N HCl (in dioxane, 5 ml) and stirred at 23° C. for 12 h. The solvent was evaporated and the residue purified by preparative HPLC (gradient 40% to 65% B) to give 15 mg (16%) of 1-[5-aminomethyl-1-(4-fluoro-butyl)-1H-benzoimidazol-2-ylmethyl]-3-methyl-1H-cinnolin-4-one as a TFA salt.

¹H NMR (DMSO-d6) δ: 1.66–1.73 (m, 4H), 2.30 (s, 3H), 4.08–4.09 (d, J=5.5 Hz, 2H), 4.39–4.44 (m, 3H), 4.50 (s, 1H), 6.06 (s, 2H), 7.35 (d, J=7.8 Hz, 1H), 7.43 (t, J=7.4 Hz, 1H), 7.65–7.69 (m, 2H), 7.76 (t, J=7.2 Hz, 1H), 7.87 (d, J=8.7 Hz, 1H), 8.10–8.15 (m, 3H);

MS m/e 393 (MH⁺).

2,3-Diamino-benzoic Acid Methyl Ester

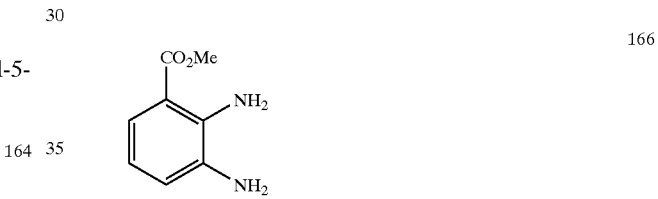

A mixture of 2-amino-3-nitro-benzoic acid methyl ester (8.0 g, 40.8 mmol) with 10% Pd/C (800 mg) in THF (60 mL) and methanol (60 mL) was rocked under a hydrogen atmosphere (45 psi) for 45 min. Fitration and concentration afforded 2,3-diamino-benzoic acid methyl ester as a tan solid, that was used without further purification.

2-Acetoxymethyl-1H-benzoimidazole-4-carboxylic Acid Methyl Ester

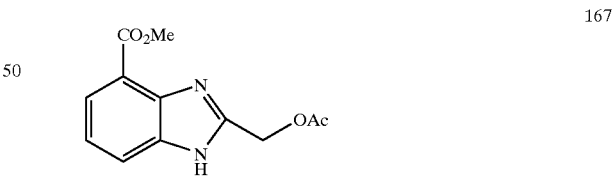

To a mixture of 2,3-diamino-benzoic acid methyl ester (40.8 mmol) and diisopropylethyl amine (8.5 mL, 49.0 mmol) in dichloromethane (80 mL) at −30° C. was added dropwise a solution of acetoxy acetyl chloride (4.8 mL, 44.9 mmol) in DCM (15 mL). The mixture was allowed to warm to room temperature and stirred overnight. The mixture was quenched with satd. ammonium chloride (50 mL), the layers separated and the aqueous phase extracted with DCM (60 mL). The combined organic layers were washed with brine and dried (MgSO₄). The residue after concentration was dissolved in acetic acid (50 mL) and heated at 100° C. for 30 min. The solution was concentrated and purified by flash chromatography (eluent DCM-ethyl acetate 3:1, 2:1, 1:1) to give 2-acetoxymethyl-1H-benzoimidazole-4-carboxylic acid methyl ester (7.3 g, 72% yield over 2 steps) as an off-white solid.

$^1$H NMR (DMSO-d6) δ: 2.11 (s, 3H), 3.96 (s, 3H), 5.31 (s, 2H), 7.32 (t, J=7.9 Hz, 1H), 7.85 (d, J=7.6 Hz, 1H), 7.93 (d, J=7.9 Hz, 1H);

MS m/e 249 (MH$^+$).

2-Hydroxymethyl-1-(3-methyl-butyl)-1H-benzoimidazole-4-carboxylic Acid Methyl Ester

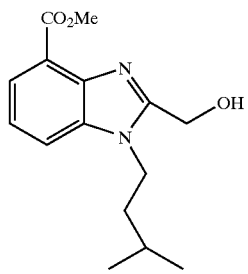

168

To a mixture of 2-acetoxymethyl-1H-benzoimidazole-4-carboxylic acid methyl ester (2.09 g, 8.42 mmol) and cesium carbonate (4.1 g, 12.6 mmol) in DMF (15 mL) at ambient temperature was added isoamyl iodide (1.34 mL, 10.1 mmol). The mixture was stirred overnight and DMF was removed in vacuo. The residue was suspended in water and extracted with ethyl acetate (twice), the combined organic phases were washed with brine, dried (MgSO$_4$) and concentrated. The residue (2-acetoxymethyl-1-(3-methyl-butyl)-1H-benzoimidazole-4-carboxylic acid methyl ester) was dissolved in methanol (20 mL) and cooled to 0° C., followed by the addition of acetyl chloride (6.0 mL, 84 mmol) and slowly allowed to reach room temperature. After stirring for 3 hrs the volatiles were removed in vacuo and the residue triturated in ethyl acetate to afford 2-hydroxymethyl-1-(3-methyl-butyl)-1H-benzoimidazole-4-carboxylic acid methyl ester after filtration (1.98 g, 85% over 2 steps) as a white solid. $^1$H NMR Analysis of the crude acetate indicated that the desired N-1 regioisomer was contaminated with the N-3 isomer (ca. 15%), which was efficiently eliminated by the ethyl acetate wash (<2%). The $^1$H NMR spectral data of the regioisomeric impurity 2-acetoxymethyl-3-(3-methyl-butyl)-3H-benzoimidazole-4-carboxylic acid methyl ester matched those of an authentic sample prepared via an independent route.

$^1$H NMR (DMSO-d6) δ:0.98 (d, J=6. Hz, 6H), 1.74–1.77 (m, 3H), 4.02 (s, 3H), 4.57–4.60 (m, 2H), 5.10 (s, 2H), 6.50 (br s, 1H), 7.75 (t, J=8.1 Hz, 1H), 8.15 (d, J=7.5 Hz, 1H), 8.29 (d, J=8.3 Hz, 1H);

MS m/e 277 (MH$^+$).

2-Chloromethyl-1-(3-methyl-butyl)-1H-benzoimidazole-4-carboxylic Acid Methyl Ester, HCl Salt:

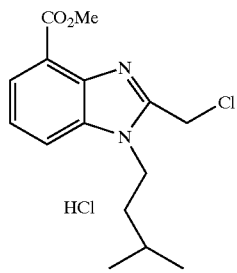

169

To a cooled (0° C.) suspension of 2-hydroxymethyl-1-(3-methyl-butyl)-1H-benzoimidazole-4-carboxylic acid methyl ester (1.98 g, 7.17 mmol) in DCM (15 mL) was added thionyl chloride (0.78 mL, 10.7 mmol). The solution was stirred at 0° C. for 15 min., allowed to warm to room temperature and stirred for 1 hr. The solution was concentrated in vacuo and the gummy residue triturated from diethyl ether and filtered to afford 2-chloromethyl-1-(3-methyl-butyl)-1H-benzoimidazole-4-carboxylic acid methyl ester, HCl salt: (2.09 g, 88%) as a white solid.

$^1$H NMR (DMSO-d6) δ: 1.00 (d, J=6.3, 6H), 1.72–1.80 (m, 3H), 3.98 (s, 3H), 4.49–4.52 (m, 2H), 5.35 (s, 2H), 7.65 (t, J=7.9, 1H), 8.04 (d, J=7.5, 1H), 8.15 (d, J=8.2, 1H);

MS m/e 295 (MH$^+$).

2-(3-Isopropyl-2-oxo-2,3-dihydro-benzoimidazol-1-ylmethyl)-1-(3-methyl-butyl)-1H-benzoimidazole-4-carboxylic Acid Methyl Ester

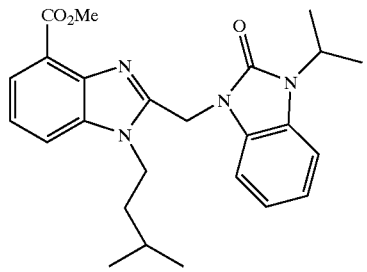

170

The procedure for the preparation of [2-(3-cyclopropyl-2,4-dioxo-3,4-dihydro-2H-quinazolin-1-ylmethyl)-1-(3-methyl-butyl)-1H-benzoimidazol-5-ylmethyl]-carbamic acid tert-butyl ester was followed starting from 2-chloromethyl-1-(3-methyl-butyl)-1H-benzoimidazole-4-carboxylic acid methyl ester, HCl salt (2.09 g, 6.31 mmol) and 1-isopropyl-1,3-dihydro-benzoimidazol-2-one (1.11 g, 6.31 mmol). The reaction time was 1.5 hrs. The suspension obatained after quenching with water was extracted with diethyl ether (2×40 mL) and the combined organic phases washed with water (4×40 mL) and brine. After drying (MgSO$_4$) and concentration the residue was purified by flash chromatography (eluent hexane-acetone 2:1) to afford 2-(3-isopropyl-2-oxo-2,3-dihydro-benzoimidazol-1-ylmethyl)-1-(3-methyl-butyl)-1H-benzoimidazole-4-carboxylic acid methyl ester (2.36 g, 86%) as a white foam:

$^1$H NMR (DMSO-d6) δ: 0.85 (d, J=6.7 Hz, 6H), 1.27–1.31 (m, 2H), 1.48 (d, J=7.0 Hz, 6H), 1.57–1.63 (m, 1H), 3.90 (s, 3H), 4.31 (t, J=8.1 Hz, 2H), 4.67 (hept., J=7.0 Hz, 1H), 5.40 (s, 2H), 7.00 (t, J=7.8 Hz, 1H), 7.04 (t, J=7.8 Hz, 1H), 7.29 (d, J=8.0 Hz, 1H), 7.34 (d, J=8.0 Hz, 1H), 7.35 (t, J=7.9 Hz, 1H), 7.77 (d, J=7.6 Hz, 1H), 7.78 (d, J=8.1 Hz, 1H);

MS m/e 435 (MH$^+$).

1-[4-Hydroxymethyl-1-(3-methyl-butyl)-1H-benzoimidazol-2-ylmethyl]-3-isopropyl-1,3-dihydro-benzoimidazol-2-one

171

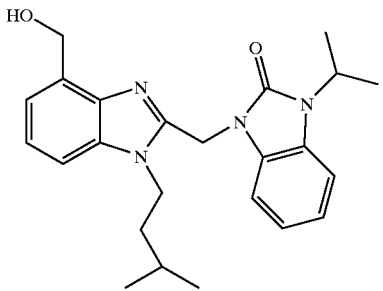

To a cooled (0° C.) solution of 2-(3-isopropyl-2-oxo-2,3-dihydro-benzoimidazol-1-ylmethyl)-1-(3-methyl-butyl)-1H-benzoimidazole-4-carboxylic acid methyl ester (2.36 g, 5.44 mmol) in THF (33 mL) was slowly added 1M LiAlH$_4$ in THF (5.46 mL, 5.46 mmol) under nitrogen. The mixture turned bright yellow and was stirred for 10 min at the same temperature. The mixture was quenched with satd. Na/K tartrate (15 mL) and extracted with ethyl acetate (2×30 mL). The combined organic layers were washed with brine and dried with MgSO$_4$. The residue after concentration was purified by flash chromatography (eluent dichloromethane: acetone 4:1, 3:1, 5:2, 2:1) to give 1-[4-Hydroxymethyl-1-(3-methyl-butyl)-1H-benzoimidazol-2-ylmethyl]-3-isopropyl-1,3-dihydro-benzoimidazol-2-one (1.21 g, 55%) as a white foam:

$^1$H NMR (DMSO-d6) δ: 0.86 (d, J=6.7 Hz, 6H), 1.27–1.31 (m, 2H), 1.48 (d, J=7.0 Hz, 6H), 1.54–1.63 (m, 1H), 4.24–4.27 (m, 2H), 4.67 (hept., J=7.0 Hz, 1H), 4.91 (s, 2H), 5.13 (br s, 1H), 5.35 (s, 2H), 6.98 (t, J=7.7 Hz, 1H), 7.03 (t, J=7.7 Hz, 1H), 7.21–7.27 (m, 3H), 7.33 (d, J=7.2 Hz, 1H), 7.35 (d, J=5.9 Hz, 1H);

MS m/e 407 (MH$^+$).

1-[4-Chloromethyl-1-(3-methyl-butyl)-1H-benzoimidazol-2-ylmethyl]-3-isopropyl-1,3-dihydro-benzoimidazol-2-one; HCl Salt

172

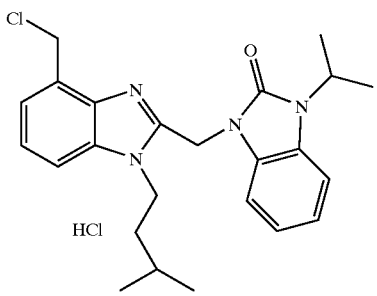

To a cooled (0° C.) solution of 1-[4-hydroxymethyl-1-(3-methyl-butyl)-1H-benzoimidazol-2-ylmethyl]-3-isopropyl-1,3-dihydro-benzoimidazol-2-one (710 mg, 1.75 mmol) in dichloromethane (9 mL) was added thionyl chloride (191 μL, 2.62 mmol). The solution was stirred at 0° C. for 15 min., warmed to ambient temperature and stirred for another 20 min. The solvent was concentrated in vacuo to give the title compound in quantitative yield 1-[4-Chloromethyl-1-(3-methyl-butyl)-1H-benzoimidazol-2-ylmethyl]-3-isopropyl-1,3-dihydro-benzoimidazol-2-one; HCl salt as a white foam, which was used without further purification.

$^1$H NMR (DMSO-d6) δ 0.83 (d, J=6.7 Hz, 6H), 1.30–1.35 (m, 2H), 1.47 (d, J=6.9 Hz, 6H), 1.55–1.63 (m, 1H), 4.34–4.37 (m, 2H), 4.66 (hept., J=7.0 Hz, 1H), 5.16 (s, 2H), 5.54 (s, 2H), 7.03 (t, J=7.4 Hz, 1H), 7.08 (t, J=7.0 Hz, 1H), 7.37–7.40 (m, 2H), 7.44 (t, J=7.9 Hz, 1H), 7.50 (d, J=7.3 Hz, 1H), 7.70 (d, J=7.9 Hz, 1H);

MS m/e 425 (MH$^+$).

1-[4-Azidomethyl-1-(3-methyl-butyl)-1H-benzoimidazol-2-ylmethyl]-3-isopropyl-1,3-dihydro-benzoimidazol-2-one

173

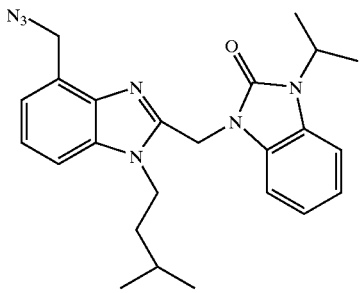

To a solution of 1-[4-chloromethyl-1-(3-methyl-butyl)-1H-benzoimidazol-2-ylmethyl]-3-isopropyl-1,3-dihydro-benzoimidazol-2-one; HCl salt (122 mg, 0.264 mmol) and diisopropylethyl amine (51 μL, 0.291 mmol) in DMF (4 mL) was added sodium azide (26 mg, 0.397 mmol) and the mixture was heated at 65° C. for 50 min. The solvent was removed in vacuo, and water was added to the residue. The product was extracted into ethyl acetate (3×10 mL), the combined organic phases were washed with water, brine and dried (MgSO$_4$) 1-[4-azidomethyl-1-(3-methyl-butyl)-1H-benzoimidazol-2-ylmethyl]-3-isopropyl-1,3-dihydro-benzoimidazol-2-one was obtained after concentration (108 mg, 95%) was used without purification.

$^1$H NMR (CDCl$_3$) δ: 0.95 (d, J=6.7 Hz, 6H), 1.40–1.45 (m, 2H), 1.56 (d, J=7.0 Hz, 6H), 1.67–1.76 (m, 1H), 4.35–4.38 (m, 2H), 4.77 (hept., J=7.0 Hz, 1H), 4.90 (br s, 2H), 5.49 (br s, 2H), 7.02–7.07 (m, 2H), 7.12 (d, J=6.6 Hz, 1H), 7.32 (br m, 3H), 7.58 (br s, 1H);

MS m/e 432 (MH$^+$).

1-[4-Aminomethyl-1-(3-methyl-butyl)-1H-benzoimidazol-2-ylmethyl]-3-isopropyl-1,3-dihydro-benzoimidazol-2-one; HCl Salt and 1-Isopropyl-3-[4-methoxymethyl-1-(3-methyl-butyl)-1H-benzoimidazol-2-ylmethyl]-1,3-dihydro-benzoimidazol-2-one

174

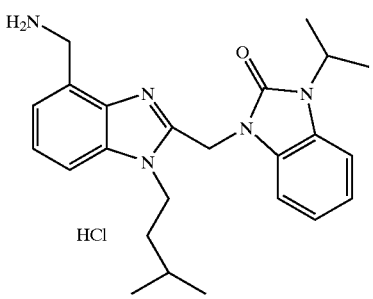

175

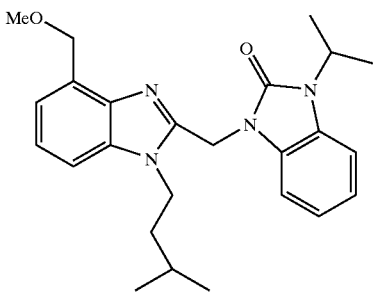

A mixture of 1-[4-azidomethyl-1-(3-methyl-butyl)-1H-benzoimidazol-2-ylmethyl]-3-isopropyl-1,3-dihydro-benzoimidazol-2-one (108 mg, 0.250 mmol) and palladium black (10 mg) in methanol (20 mL) was rocked under a hydrogen atmosphere (50 psi) for 3 hrs. The residue obtained after filtration and concentration was purified by preparative HPLC (50–70% B 20 min) to give 1-[4-aminomethyl-1-(3-methyl-butyl)-1H-benzoimidazol-2-ylmethyl]-3-isopropyl-1,3-dihydro-benzoimidazol-2-one; HCl salt as an off white solid after conversion into the hydrochloric acid salt (49 mg, 44%) along with 1-isopropyl-3-[4-methoxymethyl-1-(3-methyl-butyl)-1H-benzoimidazol-2-ylmethyl]-1,3-dihydro-benzoimidazol-2-one (4 mg, 3%) as a white solid:

1-[4-aminomethyl-1-(3-methyl-butyl)-1H-benzoimidazol-2-ylmethyl]-3-isopropyl-1,3-dihydro-benzoimidazol-2-one; HCl salt: $^1$H NMR (DMSO-d6) δ: 0.84 (d, J=6.6 Hz, 6H), 1.27–1.31 (m, 2H), 1.48 (d, J=6.9 Hz, 6H), 1.56–1.61 (m, 1H), 4.33–4.36 (m, 2H), 4.44 (q, J=5.7 Hz, 2H), 4.67 (hept., J=6.9 Hz, 1H), 5.48 (s, 2H), 7.01 (t, J=7.7 Hz, 1H), 7.07 (t, J=7.7 Hz, 1H), 7.34 (d, J=7.7 Hz, 1H), 7.36 (d, J=7.9 Hz, 1H), 7.41 (t, J=7.8 Hz, 1H), 7.46 (d, J=7.3 Hz, 1H), 7.64 (d, J=8.0 Hz, 1H), 8.54 (br s, 3H);

MS m/e 406 (MH$^+$).

1-Isopropyl-3-[4-methoxymethyl-1-(3-methyl-butyl)-1H-benzoimidazol-2-ylmethyl]-1,3-dihydro-benzoimidazol-2-one: $^1$H NMR (CD$_3$OD) δ: 0.83 (d, J=6.6 Hz, 6H), 1.39–1.42 (m, 2H), 1.55 (d +m, J=7.0 Hz, 7H), 3.45 (s, 3H), 4.41–4.44 (m, 2H), 4.70 (hept., J=7.0 Hz, 1H), 5.66 (s, 2H), 7.16 (t, J=7.7 Hz, 1H), 7.20 (t, J=7.7 Hz, 1H), 7.29 (d, J=7.6 Hz, 1H), 7.39 (d, J=7.5 Hz, 1H), 7.56 (d, J=6.9 Hz, 1H), 7.60 (t, J=8.0 Hz, 1H), 7.74 (d, J=8.2 Hz, 1H);

MS m/e 421 (MH$^+$).

[2-(3-Isopropyl-2-oxo-2,3-dihydro-benzoimidazol-1-ylmethyl)-1-(3-methyl-butyl)-1H-benzoimidazol-4-yl]-acetonitrile

176

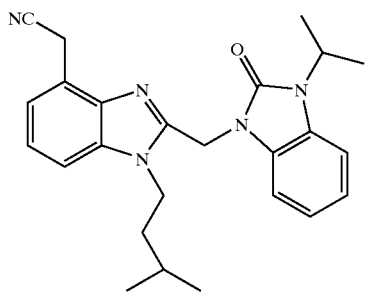

A solution containing 1-[4-chloromethyl-1-(3-methyl-butyl)-1H-benzoimidazol-2-ylmethyl]-3-isopropyl-1,3-dihydro-benzoimidazol-2-one; HCl salt (69 mg, 0.15 mmol) and sodium cyanide (30 mg, 0.62 mmol) in DMSO (1.5 mL) was stirred at room temperature for 1.5 h. The mixture was quenched with water (15 mL) and 1M NaOH (0.5 mL). The aqueous suspension was extracted with diethyl ether (2×10 mL) and the combined organic extracts washed with water, brine and dried (MgSO$_4$). [2-(3-Isopropyl-2-oxo-2,3-dihydro-benzoimidazol-1-ylmethyl)-1-(3-methyl-butyl)-1H-benzoimidazol-4-yl]-acetonitrile was obtained after concentration as a white solid (55 mg, 89%) and was used in the next step without purification:

$^1$H NMR (DMSO-d6) δ: 0.86 (d, J=6.6 Hz, 6H), 1.27–1.32 (m, 2H), 1.48 (d, J=6.9 Hz, 6H), 1.57–1.63 (m, 1H), 4.27 (s, 2H), 4.27–4.30 (m, 2H), 4.67 (hept., J=6.9 Hz 1H), 5.38 (s, 2H), 6.96 (t, J=7.9 Hz, 1H), 7.03 (t, J=7.8 Hz, 1H), 7.23 (d, J=7.1 Hz, 1H), 7.28 (t, J=7.7 Hz, 1H),7.33 (d, J=7.6 Hz, 1H), 7.35 (d, J=7.2 Hz, 1H), 7.49 (d, J=7.7 Hz, 1H).

1-[4-(2-Amino-ethyl)-1-(3-methyl-butyl)-1H-benzoimidazol-2-ylmethyl]-3-isopropyl-1,3-dihydro-benzoimidazol-2-one; HCl Salt

177

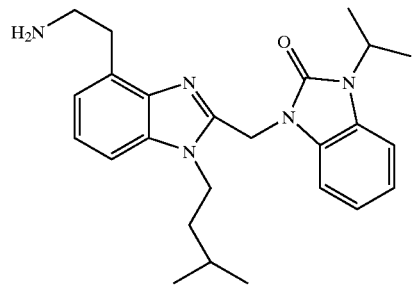

A mixture of [2-(3-isopropyl-2-oxo-2,3-dihydro-benzoimidazol-1-ylmethyl)-1-(3-methyl-butyl)-1H-benzoimidazol-4-yl]-acetonitrile (51 mg, 0.12 mmol) and 10% Pd/C (9 mg) in methanol (20 mL) was rocked in a Parr shaker under a hydrogen atmosphere (40 psi) for 15 hrs. The catalyst was removed by filtration and the filtrate concentrated. The residue was purified by preparative HPLC (30–100% B) to give 1-[4-(2-amino-ethyl)-1-(3-methyl-butyl)-1H-benzoimidazol-2-ylmethyl]-3-isopropyl-1,3-dihydro-benzoimidazol-2-one; HCl salt as the TFA salt, that was converted into the HCl salt by treatment with excess acetyl chloride in methanol, followed by removal of the volatiles in vacuo: 5 mg, 9% as a white solid.

$^1$H NMR (CD$_3$OD) δ: 0.83 (d, J=6.6 Hz, 6H), 1.39–1.44 (m, 2H), 1.55 (d+m, J=7.0 Hz, 7H), 3.36–3.43 (m, 4H), 4.43–4.46 (m, 2H), 4.69 (hept., J=6.9 Hz, 1H), 5.70 (s, 2H), 7.16–7.22 (m, 2H), 7.39–7.44 (m, 2H), 7.51 (d, J=6.8 Hz, 1H), 7.61 (t, J=8.1 Hz, 1H), 7.74 (d, J=8.1 Hz, 1H);

MS m/e 420 (MH$^+$).

2-(3-Isopropyl-2-oxo-2,3-dihydro-benzoimidazol-1-ylmethyl)-1-(3-methyl-butyl)-1H-benzoimidazole-4-carbaldehyde

178

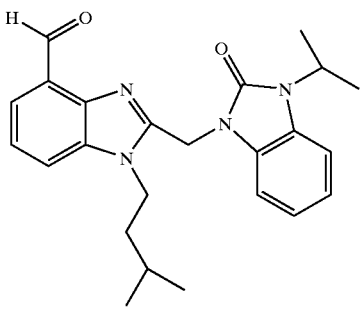

To a cooled (−45° C.) solution of oxalyl chloride (0.4 mL 2M in dichloromethane, 0.8 mmol) in DCM (5 mL) was added DMSO (115 μL, 1.62 mmol) under a nitrogen atmosphere. After stirring for 3 min. a solution of 1-[4-hydroxymethyl-1-(3-methyl-butyl)-1H-benzoimidazol-2-ylmethyl]-3-isopropyl-1,3-dihydro-benzoimidazol-2-one (300 mg, 0.738 mmol) in DCM (4 mL) was cannulated and stirring was continued for 15 min. at the same temperature. Then diisopropylethyl amine (643 μL, 3.69 mmol) was added, and the mixture was allowed to warm to room temperature after 5 min. Stirring was continued for 4 hrs, the mixture was quenched with satd. ammonium chloride and the layers separated. The aqueous phase was extracted with DCM, and the combined organic phases washed with water, brine and dried (MgSO$_4$) to afford 2-(3-Isopropyl-2-oxo-2,3-dihydro-benzoimidazol-1-ylmethyl)-1-(3-methyl-butyl)-1H-benzoimidazole-4-carbaldehyde as a pale yellow solid (quantitative recovery), that was sufficiently pure for the next steps:

$^1$H NMR (CDCl$_3$) δ: 0.97 (d, J=6.6 Hz, 6H), 1.43–1.48 (m, 2H), 1.56 (d+m, J=7.0 Hz, 7H), 4.40–4.43 (m, 2H), 4.77 (hept., J=7.0 Hz, 1H), 5.53 (s, 2H), 7.04–7.08 (m, 2H), 7.1–7.3 (hidden d, 1H), 7.43 (t, J=7.7 Hz, 1H), 7.55–7.59 (m, 2H), 7.88 (d, J=7.5 Hz, 1H), 10.91 (s, 1H);

MS m/e 405 (MH$^+$). ps 3-[2-(3-Isopropyl-2-oxo-2,3-dihydro-benzoimidazol-1-ylmethyl)-1-(3-methyl-butyl)-1H-benzoimidazol-4-yl]-acrylonitrile

179

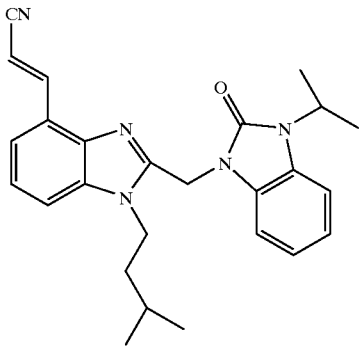

A mixture of 2-(3-isopropyl-2-oxo-2,3-dihydro-benzoimidazol-1-ylmethyl)-1-(3-methyl-butyl)-1H-benzoimidazole-4-carbaldehyde (237 mg, 0.586 mmol) and powdered KOH (33 mg, 0.59 mmol) in acetonitrile (10 mL) was heated at 70° C. for 1.5 hr. After cooling to ambient temperature saturated ammonium chloride was added followed by the removal of acetonitrile at reduced pressure. The residue was extracted with ethyl acetate (2×15 mL) and the combined organic phases washed with water, brine and dried (MgSO$_4$). Purification by flash chromatography (eluent hexane:ethyl acetate 2:1) afforded 3-[2-(3-Isopropyl-2-oxo-2,3-dihydro-benzoimidazol-1-ylmethyl)-1-(3-methyl-butyl)-1H-benzoimidazol-4-yl]-acrylonitrile (120 mg, 48%) as an off white foam:

$^1$H NMR (DMSO-d6) δ: 0.90 (d, J=6.6 Hz, 6H), 1.39–1.44 (m, 2H), 1.49 (d, J=7.0 Hz, 6H), 1.61–1.66 (m, 1H), 4.34–4.37 (m, 2H), 4.68 (hept., J=7.0 Hz, 1H), 5.42 (s, 2H), 7.00–7.07 (m, 2H), 7.17 (d, J=16.4 Hz, 1H), 7.29 (d, J=7.3 Hz, 1H), 7.31 (t, J=7.9, 1H), 7.35 (d, J=7.8 Hz, 1H), 7.41 (d, J=7.3 Hz, 1H), 7.65 (d, J=7.8 Hz, 1H), 7.80 (d, J=16.4 Hz, 1H);

MS m/e 428 (MH$^+$).

3-[2-(3-Isopropyl-2-oxo-2,3-dihydro-benzoimidazol-1-ylmethyl)-1-(3-methyl-butyl)-1H-benzoimidazol-4-yl]-propionitrile

180

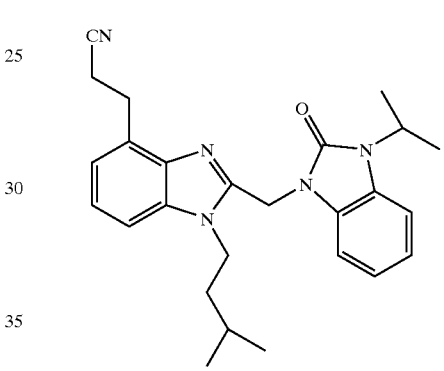

A mixture of 3-[2-(3-isopropyl-2-oxo-2,3-dihydro-benzoimidazol-1-ylmethyl)-1-(3-methyl-butyl)-1H-benzoimidazol-4-yl]-acrylonitrile (100 mg, 0.234 mmol) and 10% Pd-C (10 mg) in THF (2 mL) and methanol (25 mL) was rocked in a Parr shaker under a hydrogen atmosphere (50 psi) for 15 hrs. The catalyst was removed by filtration and the filtrate purified by flash chromatography (eluent hexane:ethyl acetate 1:1) to afford 3-[2-(3-Isopropyl-2-oxo-2,3-dihydro-benzoimidazol-1-ylmethyl)-1-(3-methyl-butyl)-1H-benzoimidazol-4-yl]-propionitrile (74 mg, 74%) as a white solid:

$^1$H NMR (DMSO-d6) δ: 0.87 (d, J=6.7 Hz, 6H), 1.28–1.32 (m, 2H), 1.48 (d, J=7.0 Hz, 6H), 1.58–1.64 (m, 1H), 3.02 (t, J=7.2 Hz, 2H), 3.24 (t, J=7.2 Hz, 2H), 4.25–4.28 (m, 2H), 4.68 (hept., J=7.0 Hz, 1H), 5.37 (s, 2H), 6.97 (t, J=7.7 Hz, 1H), 7.03 (t, J=7.7 Hz, 1H), 7.12 (d, J=7.2 Hz, 1H), 7.21 (t, J=7.4 Hz, 1H), 7.29 (d, J=7.2 Hz, 1H), 7.33 (d, J=7.7 Hz, 1H), 7.39 (d, J=7.9 Hz, 1H);

MS m/e 430 (MH$^+$).

1-[4-(3-Amino-propyl)-1-(3-methyl-butyl)-1H-benzoimidazol-2-ylmethyl]-3-isopropyl-1,3-dihydro-benzoimidazol-2-one; HCl Salt

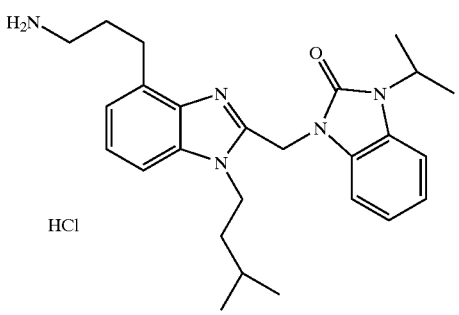

181

A mixture of 3-[2-(3-isopropyl-2-oxo-2,3-dihydro-benzoimidazol-1-ylmethyl)-1-(3-methyl-butyl)-1H-benzoimidazol-4-yl]-propionitrile (30 mg, 0.070 mmol) and 10% Pd-C (10 mg) methanol (20 mL) and concentrated HCl (1 mL) was placed in a Parr shaker and rocked under a hydrogen atmosphere (50 psi) for 15 hrs. The catalyst was removed by filtration and the filtrate purified by preparative HPLC (gradient 30–80% B). The title compound was dissolved in dichloromethane and converted into the HCl salt by addition of excess 4N HCl in dioxane. After concentration 1-[4-(3-amino-propyl)-1-(3-methyl-butyl)-1H-benzoimidazol-2-ylmethyl]-3-isopropyl-1,3-dihydro-benzoimidazol-2-one; HCl salt (16 mg, 49%) was obtained as a sticky colorless oil:

$^1$H NMR (CD$_3$OD) δ: 0.80 (d, J=6.6 Hz, 6H), 1.36–1.41 (m, 2H), 1.55 (d+m, J=7.0 Hz, 7H), 2.09–2.15 (m, 2H), 3.05 (t, J=7.5 Hz, 2H), 3.16 (t, J=7.77 Hz, 2H), 4.41–4.44 (m, 2H), 4.69 (hept., J=7.0 Hz, 1H), 5.71 (s, 2H), 7.17–7.23 (m, 2H), 7.39–7.42 (m, 2H), 7.50 (d, J=7.4 Hz, 1H), 7.60 (t, J=7.5 Hz, 1H), 7.69 (d, J=8.3 Hz, 1H);

MS m/e 434 (MH$^+$).

2-(3-Isopropyl-2-oxo-2,3-dihydro-benzoimidazol-1-ylmethyl)-1-(3-methyl-butyl)-1H-benzoimidazole-4-carboxylic Acid

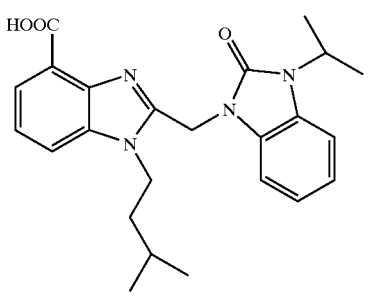

182

A mixture of 2-(3-Isopropyl-2-oxo-2,3-dihydro-benzoimidazol-1-ylmethyl)-1-(3-methyl-butyl)-1H-benzoimidazole-4-carbaldehyde (37 mg, 0.091 mmol) and sodium chlorite (12 mg, 0.11 mmol) in water (1 mL) and acetonitrile (1 mL) was stirred at room temperature for 8 hrs. An additional amount of sodium chlorite (12 mg) was added and stirring was continued overnight. 1M NaOH was added and the mixture was extracted with ethyl acetate (twice). The aqueous phase was acidified with 1M HCl until pH 4. The resulting suspension was extracted with ethyl acetate (2×10 mL) and the combined organic phases washed with water, brine, and dried (MgSO$_4$). The pure title compound (8 mg, 21%) was obtained as a white solid:

$^1$H NMR (CDCl$_3$) δ: 0.99 (d, J=6.6 Hz, 6H), 1.50–1.56 (m, 2H), 1.56 (d, J=7.0 Hz, 6H), 1.70–1.76 (m, 1H), 4.43–4.47 (m, 2H), 4.76 (hept., J=7.0 Hz, 1H), 5.46 (s, 2H), 7.06–7.11 (m, 2H), 7.14–7.16 (m, 1H), 7.36–7.37 (m, 1H), 7.44 (t, J=7.7, 1H), 7.56 (d, J=8.2 Hz, 1H), 8.09 (d, J=7.5 Hz, 1H);

MS m/e 421 (MH$^+$).

Biological Activity

The antiviral activity of these compounds against respiratory syncytial virus (RSV) was examined in a cell protection assay to determine compound ability to protect cells from RSV-induced cytopathic effects (CPE) or in a viral replication assay to determine compound capacity to directly inhibit RSV replication as measured by the reduction of RSV protein expression.

For cell protection assays, HEp-2 (ATCC CCL 23) cells were seeded in 96 well microtiter plates at 1.5×10$^4$ cells/100 μL/well in DMEM (Dulbecco's Modified Eagle's Medium) supplemented with penicillin, streptomycin, glutamine, and 10% fetal bovine serum. After overnight incubation at 37° C., the culture medium was removed and cells were infected with respiratory syncytial virus Long strain at 5000 plaque forming units (PFU)/mL in a 100 μL volume of medium containing 2% fetal bovine serum. The compounds, 100 μL at appropriate dilution, were added to the cells one hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 μL/well of acidified isopropanol (per liter: 900 mL isopropanol, 100 mL Triton X100, and 4 mL conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells containing compound with uninfected cells in the absence of compound provide a measure of cellular toxicity. The control compound in this assay is Ribavirin, which exhibits 100% cell protection at 2.5 μg/mL (corresponding to 10.2 μM).

The antiviral activity of compounds, designated as EC$_{50}$, is presented as a concentration that produces 50% cell protection in the assay. The compounds disclosed in this application show antiviral activity with EC$_{50}$'s between 50 μM and 0.001 μM. Ribavirin has an EC$_{50}$ of 3 μM in this assay.

Direct compound inhibition of RSV replication was assessed by measuring the reduction of viral protein expression. Assays entail the quantitation of [$^{35}$S]-methionine labeled viral proteins synthesized in RSV infected cells. Near confluent Hep2 cells (80%) in 35 mm dishes were infected with RSV at a multiplicity of infection (MOI) of 2 RSV PFU/cell in the presence or absence of compound in DMEM supplemented with 2% FBS, pen/strep and glutamine. Eighteen hours post infection, the media was removed and the infected cells were "starved" in 1 ml of DMEM minus methionine for 30 minutes. The media was then replaced with 200 ul of DMEM minus methionine containing 20 uCi [$^{35}$S]-methionine. After 90 minutes at 37° C. the labeling media was removed and the monolayers were carefully washed with 2 mls of PBS. The cells were lysed in 200 ul of radioimmunoprecipitation assay buffer (RIPA: 50 mM Tris pH 8.0, 150 mM NaCl, 1% NP40, 0.5% sodium dexoycholate and 0.1% SDS). The cell lysates were spun in an epppendorf centrifuge for 5 minutes at 14,000 rpm. 5 ug of Goat anti-RSV polyclonal IgG (Fitzgerald Industries, Concord, Mass.) was added to 150 ul of the supernatant.

After 1 hour at room temperature, a 25 ul suspension of Protein-G sepharose in PBS was added and incubation with gentle rocking continued for another hour. The Protein-G sepharose beads were washed 4 times with 1 ml of RIPA buffer and resuspended in 30 ul of SDS PAGE sample buffer, heated to 95° C. for 2 minutes and electrophoresed on 12% acrylamide SDS PAGE Gels. Gels were fixed in 10% acetic acid/30% methanol and radiolabeled proteins were detected by autoradiography of the dried gel. RSV protein bands were quantitated by scanning autoradiographs with a Molecular Dynamics Personal Densitometer SI with ImageQuaNT software (Sunnyvale, Calif.). Compound antiviral activity is designated by an $EC_{50pro}$ value, representing the concentration required to inhibit RSV protein expression by 50%.

The antiviral activity of compounds, designated as $EC_{50pro}$, is presented as a concentration that produces 50% cell protection in the assay. The compounds disclosed in this application show antiviral activity with $EC_{50pro}$'s between 50 μM and 0.001 μM. Ribavirin has an $EC_{50}$ of 3 μM in this assay.

What is claimed is:

1. A compound having the Formula I, and pharmaceutically acceptable salts thereof,

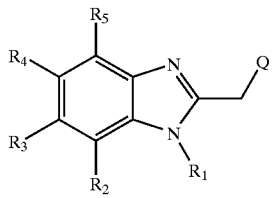

Formula I wherein:

$R_1$ is —$(CR^aR^b)_n$—X;

$R^a$ and $R^b$ are each independently selected from the group consisting of H and $C_{1-6}$ alkyl; said $C_{1-6}$ alkyl being optionally substituted with one to six same or different halogen;

X is H or $C_{1-6}$ alkyl; said $C_{1-6}$ alkyl being optionally substituted with halogen, $OR^c$ or $S(O)_mR^d$;

$R^c$ is H or $COR^d$;

$R^d$ is $C_{1-6}$ alkyl;

n is 1–6;

m is 0–2;

$R_2$ is H;

$R_3$ is hydrogen, $CONR^hR^i$, $CO_2R^d$ or $C_{1-6}$ alkyl; said $C_{1-6}$ alkyl can be optionally substituted with $OR^e$ or $NR^fR^g$;

$R^e$ is H or $C_{1-6}$ alkyl;

$R^f$ and $R^g$ are each independently H, $C_{1-6}$ alkyl, $SO_2R^d$, $CO_2R^d$ or $COR^d$;

$R^h$ and $R^i$ are each independently H or $C_{1-6}$ alkyl;

$R_4$ is selected from the group consisting of hydrogen, amino, $CONR^hR^i$, heteroaryl selected from the group consisting of oxadiazole, oxazole, and oxadiazolinone, $C_{2-6}$ alkenyl, $CO_2R^d$, N=$CPh_2$, C(=NOH)$NH_2$, C(=NH)$NH_2$ and $C_{1-6}$ alkyl; said $C_{1-6}$ alkyl optionally substituted with a member selected from the group consisting of halogen, CN, $NR^lR^m$, $OSO_2R^d$ and $OR^e$;

$R^l$ and $R^m$ are each independently selected from the group consisting of H, $C_{1-6}$ alkyl, $C_{3-6}$ cycloalkyl, $CO_2R^d$, $COR^d$ and $SO_2R^d$;

$R_5$ is selected from the group consisting of (1) hydrogen; (2) $CO_2R^j$; (3) $C_{1-6}$ alkyl optionally substituted with CN, $OR^e$ or $NR^fR^g$; and (4) $C_{2-6}$ alkenyl substituted with CN;

$R^j$ is H or $C_{1-6}$ alkyl;

provided that $R_3$, $R_4$, and $R_5$ are not all hydrogen;

Q is a member selected from the group consisting of

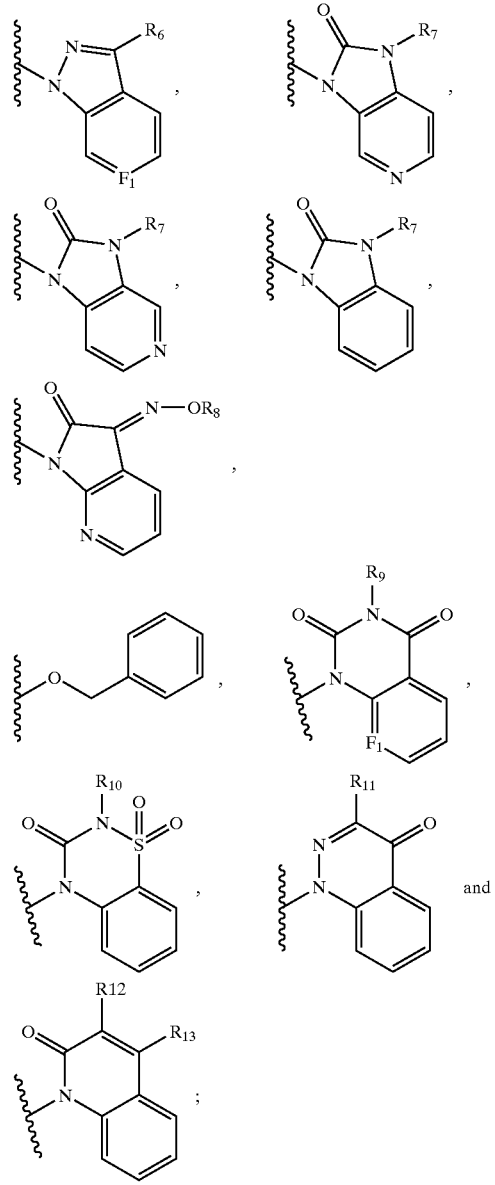

$F_1$ is CH or N;

$R_6$ is H, halogen, $C_{1-6}$ alkyl or $C_{2-6}$ alkenyl;

$R_7$ is H, $C_{1-6}$ alkyl, $C_{2-6}$ alkenyl, $CO_2R^d$ or $C_{3-6}$ cycloalkyl;

$R_8$ is H or $C_{1-6}$ alkyl; said $C_{1-6}$ alkyl optionally substituted with one to three halogen;

$R_9$ is $C_{1-6}$ alkyl or $C_{3-6}$ cycloalkyl; said $C_{1-6}$ alkyl optionally substituted with one to three halogen;

$R_{10}$ is $C_{1-6}$ alkyl or $C_{3-6}$ cycloalkyl; said $C_{1-6}$ alkyl optionally substituted with one to three halogen;

$R_{11}$ is H or $C_{1-2}$ alkyl;

$R_{12}$ is H; and $R_{13}$ is H or $OR^j$.

2. A compound of claim 1 wherein:

$R^a$ and $R^b$ are hydrogen.

3. A compound of claim 1 wherein:

$R_1$ is 3-methyl-butyl or —$(CH_2)_n$—X; wherein n is 2–6; and X is a member selected from the group consisting of F, $SO_2R^d$ and $OR^c$.

4. A compound of claim 1 wherein heteroaryl is selected from the group consisting of 1,2,3-oxadiazolyl, 1,2,4-oxadiazolyl and 1,2,4-oxadiazol-5-one.

5. A method for treating mammals infected with RSV, and in need thereof, which comprises administering to said mammal a therapeutically effective amount of one or more of the aforementioned compounds as claimed in any one of claims 1–4.

6. A pharmaceutical composition which comprises a therapeutically effective amount of one or more of the aforementioned anti-RSV compounds as claimed in any one of claims 1–4 and a pharmaceutically acceptable carrier.

* * * * *